United States Patent
Lee et al.

(10) Patent No.: US 10,270,042 B2
(45) Date of Patent: Apr. 23, 2019

(54) COMPOUND FOR ORGANIC OPTOELECTRIC DEVICE AND ORGANIC OPTOELECTRIC DEVICE AND DISPLAY DEVICE

(71) Applicant: SAMSUNG SDI CO., LTD., Yongin-si, Gyeonggi-do (KR)

(72) Inventors: Hanill Lee, Suwon-si (KR); Dongkyu Ryu, Suwon-si (KR); Dong Min Kang, Suwon-si (KR); Eun Sun Yu, Suwon-si (KR); Byoungkwan Lee, Suwon-si (KR); Sung-Hyun Jung, Suwon-si (KR); Sujin Han, Suwon-si (KR)

(73) Assignee: Samsung SDI Co., Ltd., Yongin-Si, Gyeonggi-do (KR)

( * ) Notice: Subject to any disclaimer, the term of this patent is extended or adjusted under 35 U.S.C. 154(b) by 180 days.

(21) Appl. No.: 15/461,620

(22) Filed: Mar. 17, 2017

(65) Prior Publication Data

US 2017/0346019 A1    Nov. 30, 2017

(30) Foreign Application Priority Data

May 31, 2016    (KR) .................. 10-2016-0067440

(51) Int. Cl.
| | | |
|---|---|---|
| *C09K 11/02* | (2006.01) | |
| *C09K 11/06* | (2006.01) | |
| *H01L 51/00* | (2006.01) | |
| *H01L 51/50* | (2006.01) | |
| *C07D 487/04* | (2006.01) | |
| *C07D 487/14* | (2006.01) | |

(52) U.S. Cl.
CPC ........ *H01L 51/0072* (2013.01); *C07D 487/04* (2013.01); *C07D 487/14* (2013.01); *C09K 11/025* (2013.01); *C09K 11/06* (2013.01); *H01L 51/0067* (2013.01); *H01L 51/5016* (2013.01)

(58) Field of Classification Search
CPC .. C07D 487/04; C07D 487/14; C09K 11/025; C09K 11/06; H01L 51/0067; H01L 51/0072; H01L 51/5016
See application file for complete search history.

(56) References Cited

U.S. PATENT DOCUMENTS

| | | |
|---|---|---|
| 2010/0109514 A1 | 5/2010 | Schafer et al. |
| 2013/0048975 A1 | 2/2013 | Hong et al. |
| 2015/0349269 A1 | 12/2015 | Lee et al. |
| 2016/0141512 A1 | 5/2016 | Jung |

FOREIGN PATENT DOCUMENTS

| | | |
|---|---|---|
| CN | 102482222 A | 5/2012 |
| CN | 106029831 A | 10/2016 |
| CN | 106104838 A | 11/2016 |
| JP | 2001-02377 | 1/2001 |
| JP | 2003-040873 | 2/2003 |
| KR | 10-2011-0042004 | 4/2011 |
| KR | 10-1196093 | 10/2012 |

(Continued)

OTHER PUBLICATIONS

Chinese Office Action dated Dec. 29, 2018.

*Primary Examiner* — Dawn L Garrett
(74) *Attorney, Agent, or Firm* — Lee & Morse, P.C.

(57) ABSTRACT

A compound for an organic optoelectric device represented by Chemical Formula I, an organic optoelectric device including the same, and a display device are disclosed. Details of Chemical Formula I are defined in the specification.

11 Claims, 1 Drawing Sheet

(56) References Cited

FOREIGN PATENT DOCUMENTS

| | | |
|---|---|---|
| KR | 10-2014-0135524 | 11/2014 |
| KR | 10-1486096 | 1/2015 |
| WO | WO 2016/024675 A1 | 2/2016 |
| WO | WO 2016/060332 A1 | 4/2016 |
| WO | WO 2016/204375 A1 | 12/2016 |

COMPOUND FOR ORGANIC OPTOELECTRIC DEVICE AND ORGANIC OPTOELECTRIC DEVICE AND DISPLAY DEVICE

CROSS-REFERENCE TO RELATED APPLICATION

This application claims priority to and the benefit of Korean Patent Application No. 10-2016-0067440 filed in the Korean Intellectual Property Office on May 31, 2016, the entire contents of which are incorporated herein by reference.

BACKGROUND OF THE INVENTION

(a) Field of the Invention

A compound for an organic optoelectric device, an organic optoelectric device, and a display device are disclosed.

(b) Description of the Related Art

An organic optoelectric device (organic optoelectric diode) is a device that converts electrical energy into photoenergy, and vice versa.

An organic optoelectric device may be classified as follows in accordance with its driving principles. One is a photoelectric device where excitons are generated by photoenergy, separated into electrons and holes, and are transferred to different electrodes to generate electrical energy, and the other is a light emitting device where a voltage or a current is supplied to an electrode to generate photoenergy from electrical energy.

Examples of the organic optoelectric device may be an organic photoelectric device, an organic light emitting diode, an organic solar cell, and an organic photo conductor drum.

Of these, an organic light emitting diode (OLED) has recently drawn attention due to an increase in demand for flat panel displays. The organic light emitting diode converts electrical energy into light by applying current to an organic light emitting material and has a structure in which an organic layer is disposed between an anode and a cathode. Herein, the organic layer may include a light-emitting layer and optionally an auxiliary layer, and the auxiliary layer may be, for example at least one selected from a hole injection layer, a hole transport layer, an electron blocking layer, an electron transport layer, an electron injection layer, and a hole blocking layer for improving efficiency and stability of an organic light emitting diode.

Performance of an organic light emitting diode may be affected by characteristics of the organic layer, and among them, may be mainly affected by characteristics of an organic material of the organic layer.

Particularly, development for an organic material being capable of increasing hole and electron mobility and simultaneously increasing electrochemical stability is needed so that the organic light emitting diode may be applied to a large-size flat panel display.

SUMMARY OF THE INVENTION

An embodiment provides a compound for an organic optoelectric device capable of realizing an organic optoelectric device having high efficiency and a long life-span.

Another embodiment provides an organic optoelectric device including the compound for an organic optoelectric device.

Yet another embodiment provides a display device including the organic optoelectric device.

According to an embodiment, a compound for an organic optoelectric device represented by Chemical Formula I is provided.

[Chemical Formula I]

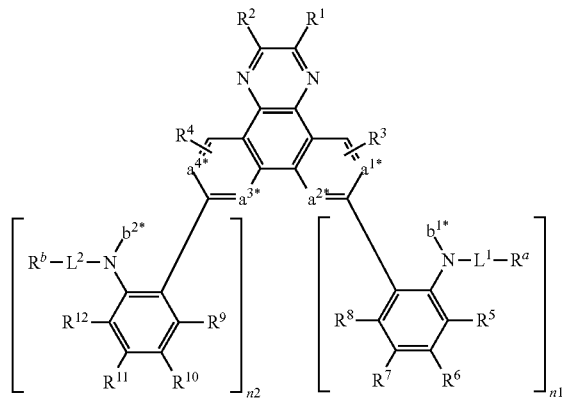

In Chemical Formula I,
$a^{1*}$ to $a^{4*}$ are independently C or $CR^c$,
$a^{1*}$ or $a^{2*}$ is linked with $b^{1*}$,
$a^{3*}$ or $a^{4*}$ is linked with $b^{2*}$,
$R^1$ to $R^{12}$ and $R^c$ are independently hydrogen, deuterium, a substituted or unsubstituted C1 to C10 alkyl group, a substituted or unsubstituted C6 to C20 aryl group, a substituted or unsubstituted C2 to C30 heteroaryl group, or a combination thereof,
$R^5$ to $R^{12}$ are independently present or $R^5$ and $R^6$, $R^6$ and $R^7$, $R^7$ and $R^8$, $R^9$ and $R^{10}$, $R^{10}$ and $R^{11}$, and $R^{11}$ and $R^{12}$ are optionally fused to form a ring,
$L^1$ and $L^2$ are independently a single bond, a substituted or unsubstituted C6 to C30 arylene group, or a substituted or unsubstituted C2 to C30 heteroarylene group,
$R^a$ and $R^b$ are independently a substituted or unsubstituted C6 to C30 aryl group, a substituted or unsubstituted C2 to C30 heteroaryl group, or a combination thereof,
n1 and n2 are independently an integer of 0 or 1, and
$1 \leq n1+n2 \leq 2$.

The "substituted" refers to replacement of at least one hydrogen by deuterium, a C1 to C30 alkyl group, a C6 to C30 aryl group, or C2 to C30 heteroaryl group.

According to another embodiment, an organic optoelectric device includes an anode and a cathode facing each other and at least one organic layer disposed between the anode and the cathode, wherein the organic layer includes the compound for an organic optoelectric device.

According to another embodiment, a display device including the organic optoelectric device is provided.

An organic optoelectric device having high efficiency and a long life-span may be realized.

DETAILED DESCRIPTION

Figure 1:
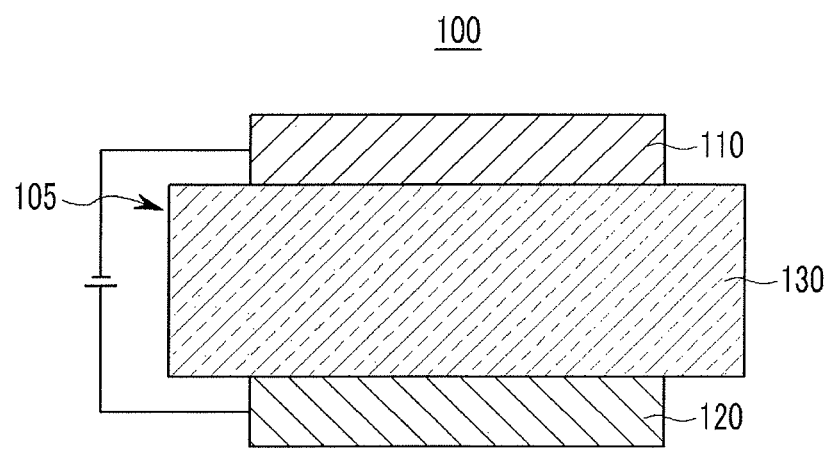
FIGS. 1 and 2 are cross-sectional views showing organic light emitting diodes according to embodiments.

Hereinafter, embodiments of the present disclosure are described in detail. However, these embodiments are exemplary, the present invention is not limited thereto and the present invention is defined by the scope of claims.

As used herein, when a definition is not otherwise provided, "substituted" refers to replacement of at least one hydrogen of a substituent or a compound by deuterium, a halogen, a hydroxyl group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C6 to C30 arylsilyl group, a C3 to C30 cycloalkyl group, a C3 to C30 heterocycloalkyl group, a C6 to C30 aryl group, a C6 to C30 heteroaryl group, a C1 to C20 alkoxy group, a fluoro group, a C1 to C10 trifluoroalkyl group, or a cyano group.

In the present specification, when specific definition is not otherwise provided, "hetero" refers to one including one to three heteroatoms selected from N, O, S, P, and Si, and remaining carbons in one functional group.

In the present specification, when a definition is not otherwise provided, "alkyl group" refers to an aliphatic hydrocarbon group. The alkyl group may be "a saturated alkyl group" without any double bond or triple bond.

The alkyl group may be a C1 to C30 alkyl group. More specifically, the alkyl group may be a C1 to C20 alkyl group or a C1 to C10 alkyl group. For example, a C1 to C4 alkyl group may have 1 to 4 carbon atoms in alkyl chain which may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, "aryl group" refers to a group including at least one hydrocarbon aromatic moiety, and all the elements of the hydrocarbon aromatic moiety have p-orbitals which form conjugation, for example a phenyl group, a naphthyl group, and the like, two or more hydrocarbon aromatic moieties may be linked by a sigma bond and may be, for example a biphenyl group, a terphenyl group, a quarterphenyl group, and the like, and two or more hydrocarbon aromatic moieties are fused directly or indirectly to provide a non-aromatic fused ring. For example, it may be a fluorenyl group.

The aryl group may include a monocyclic, polycyclic or fused ring polycyclic (i.e., rings sharing adjacent pairs of carbon atoms) functional group.

In the present specification, a "heteroaryl group" may refer to an aryl group including one to three heteroatoms selected from N, O, S, P, and Si and remaining carbon. Two or more heteroaryl groups are linked by a sigma bond directly, or when the heteroaryl group includes two or more rings, the two or more rings may be fused. When the heteroaryl group is a fused ring, each ring may include one to three heteroatoms.

Specific examples of the heteroaryl group may be a pyridinyl group, a pyrimidinyl group, a pyrazinyl group, a pyridazinyl group, a triazinyl group, a quinolinyl group, an isoquinolinyl group, and the like.

More specifically, the substituted or unsubstituted C6 to C30 aryl group and/or the substituted or unsubstituted C2 to C30 heteroaryl group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted fluorenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted dibenzofuranyl group, or a substituted or unsubstituted dibenzothiophenyl group, or a combination thereof, but are not limited thereto.

In the present specification, hole characteristics refer to an ability to donate an electron to form a hole when an electric field is applied, and that a hole formed in the anode may be easily injected into a light-emitting layer, and a hole formed in a light-emitting layer may be easily transported into an anode and transported in a light-emitting layer due to conductive characteristics according to a highest occupied molecular orbital (HOMO) level.

In addition, electron characteristics refer to an ability to accept an electron when an electric field is applied, and that an electron formed in a cathode may be easily injected into a light-emitting layer, and an electron formed in a light-emitting layer may be easily transported into a cathode and transported in a light-emitting layer due to conductive characteristics according to a lowest unoccupied molecular orbital (LUMO) level.

Hereinafter, a compound for an organic optoelectric device according to an embodiment is described.

A compound for an organic optoelectric device according to one embodiment is represented by Chemical Formula I.

[Chemical Formula I]

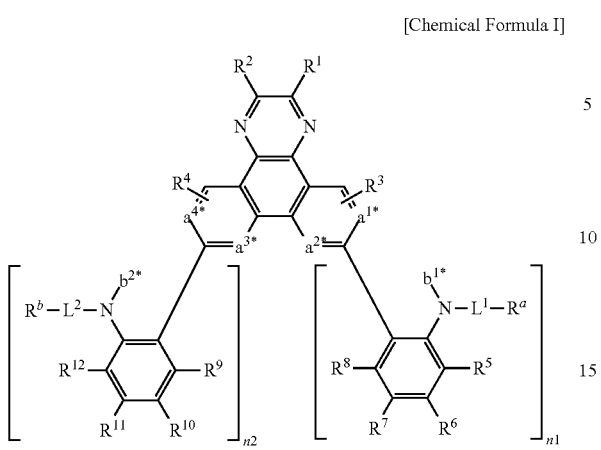

In Chemical Formula I,
a$^1$* to a$^4$* are independently C or CR$^c$,
a$^1$* or a$^2$* is linked with b$^1$*,
a$^3$* or a$^4$* is linked with b$^2$*,
R$^1$ to R$^{12}$ and R$^c$ are independently hydrogen, deuterium, a substituted or unsubstituted C1 to C10 alkyl group, a substituted or unsubstituted C6 to C20 aryl group, a substituted or unsubstituted C2 to C30 heteroaryl group, or a combination thereof.

R$^5$ to R$^{12}$ are independently present or R$^5$ and R$^6$, R$^6$ and R$^7$, R$^7$ and R$^8$, R$^9$ and R$^{10}$, R$^{10}$ and R$^{11}$, and R$^{11}$ and R$^{12}$ are optionally fused to form a ring, L$^1$ and L$^2$ are independently a single bond, a substituted or unsubstituted C6 to C30 arylene group, or a substituted or unsubstituted C2 to C30 heteroarylene group, R$^a$ and R$^b$ are independently a substituted or unsubstituted C6 to C30 aryl group, a substituted or unsubstituted C2 to C30 heteroaryl group, or a combination thereof, n1 and n2 are independently an integer of 0 or 1, and 1≤n+n2≤2.

The "substituted" refers to replacement of at least one hydrogen by deuterium, a C1 to C30 alkyl group, a C6 to C30 aryl group, or a C2 to C30 heteroaryl group.

The compound for an organic optoelectric device represented by Chemical Formula I forms an asymmetric steric structure where an azatriphenylene including a "nitrogen (N)" unit is fused with carbazole.

In the present specification, "linked with b$^1$*" or "linked with b$^2$*" refers to linking with "N" through "b$^1$*" or "b$^2$*" and herein b$^1$* and b$^2$* are single bonds and a$^1$* to a$^4$* linked with b$^1$* or b$^2$* may be C.

On the other hand, a$^1$* to a$^4$* that are not linked with b$^1$* and b$^2$* may be CR$^c$ wherein a definition of R$^c$ is the same as described above.

The "nitrogen(N)" unit of the compound for an organic optoelectric device represented by Chemical Formula I has polarity and interacts with an electrode, and charges may be easily injected and mobility increases, and thereby a driving voltage may be reduced.

In addition, an intermolecular interaction may be small due to the steric structure of molecules, crystallization of molecules may be suppressed and thereby yield improvement and long life-span of an organic light emitting diode may be expected.

The asymmetric structure may make deposition at a low temperature possible, and thus decomposition during deposition may be suppressed and a long life-span may be obtained.

The compound for an organic optoelectric device may be, for example represented by one of Chemical Formula I-A, I-B, I-C, I-D, and I-E according to a fused position of the carbazole and additional fusion of the carbazole.

[Chemical Formula I-A]

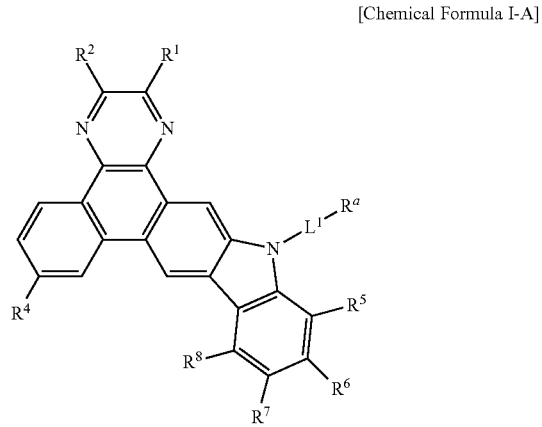

[Chemical Formula I-B]

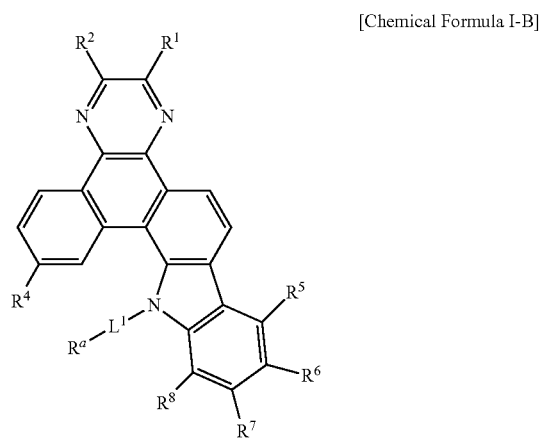

[Chemical Formula I-C]

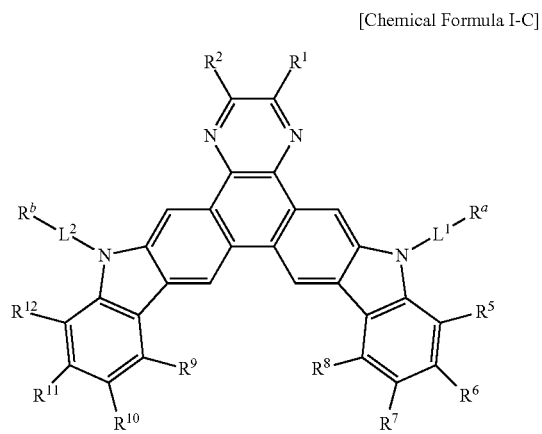

-continued

[Chemical Formula I-D]

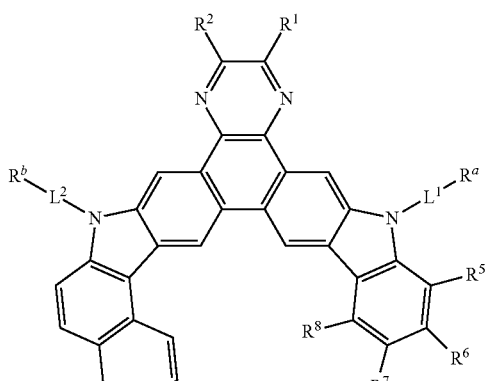

[Chemical Formula I-E]

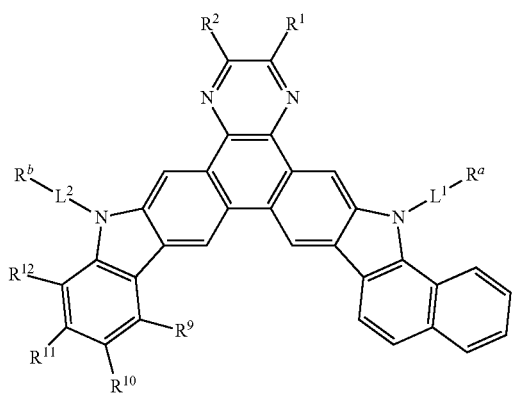

[Group 1]

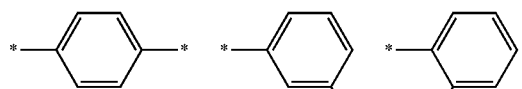

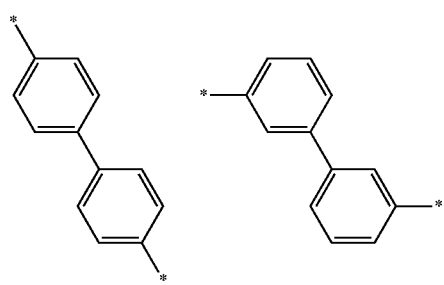

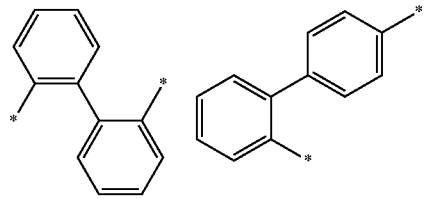

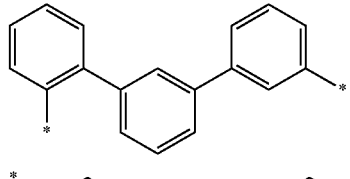

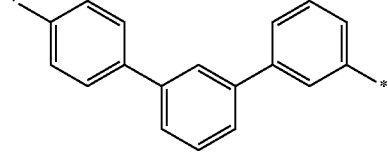

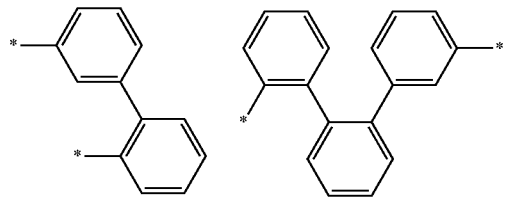

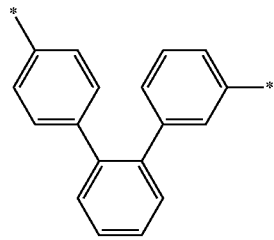

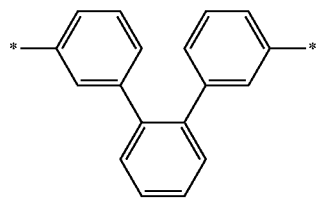

In Chemical Formulae I-A to I-E, $R^1$, $R^2$, and $R^4$ to $R^{12}$ are independently hydrogen, deuterium, a substituted or unsubstituted C to C10 alkyl group, a substituted or unsubstituted C6 to C20 aryl group, a substituted or unsubstituted C2 to C30 heteroaryl group, or a combination thereof, $L^1$ and $L^2$ are independently a single bond, a substituted or unsubstituted C6 to C30 arylene group, or a substituted or unsubstituted C2 to C30 heteroarylene group, $R^a$ and $R^b$ are independently a substituted or unsubstituted C6 to C30 aryl group, a substituted or unsubstituted C2 to C30 heteroaryl group, or a combination thereof, and the "substituted" refers to replacement of at least one hydrogen by deuterium, a C1 to C30 alkyl group, a C6 to C30 aryl group, or a C2 to C30 heteroaryl group.

According to an embodiment, $L^1$ and $L^2$ of Chemical Formula I may independently be a single bond, a substituted or unsubstituted C6 to C30 arylene group, or a substituted or unsubstituted C2 to C30 heteroarylene group, and specifically a single bond, or a substituted or unsubstituted C6 to C30 arylene group.

When $L^1$ and $L^2$ are a substituted or unsubstituted C6 to C30 arylene group, for example, one to four phenyl groups may be linked.

That is, $L^1$ and $L^2$ may be a single bond, a phenylene group, a biphenylene group, a terphenylene group, a quaterphenylene group, or a combination thereof, and specific examples thereof may be selected from linking groups of Group 1.

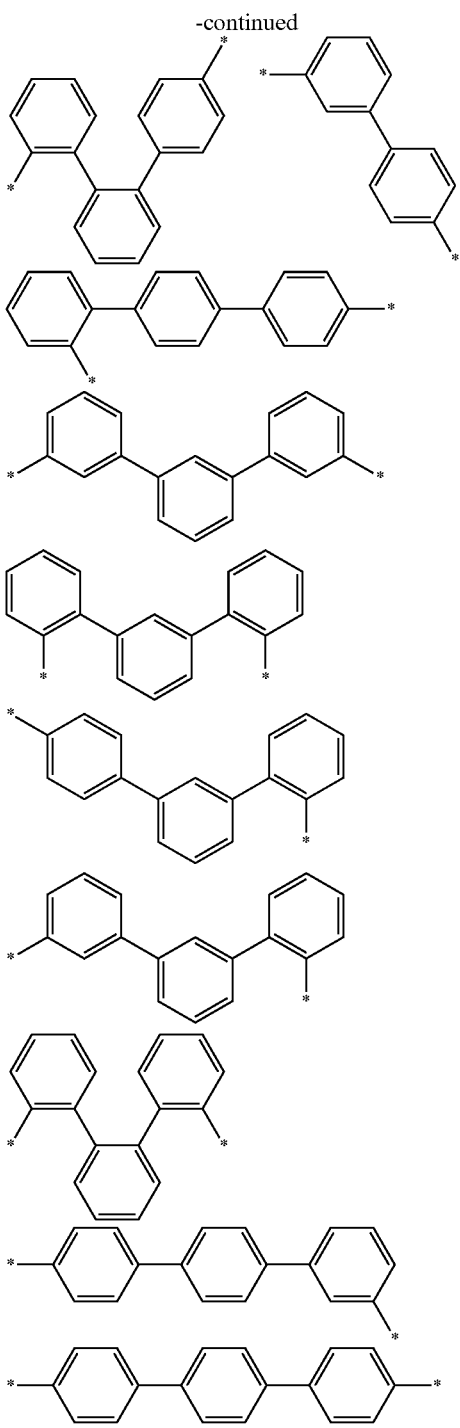

In Group 1, * is a linking site with an adjacent atom.

According to an embodiment, $R^a$ and $R^b$ of Chemical Formula I may independently be a substituted or unsubstituted C6 to C30 aryl group, a substituted or unsubstituted C2 to C30 heteroaryl group, or a combination thereof, specifically a substituted or unsubstituted phenyl group, a substituted or unsubstituted biphenyl group, a substituted or unsubstituted terphenyl group, a substituted or unsubstituted quaterphenyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted indolyl group, a substituted or unsubstituted azaindolyl group, a substituted or unsubstituted benzoxazolyl group, a substituted or unsubstituted benzthiazolyl group, a substituted or unsubstituted azatriphenylenyl group, a substituted or unsubstituted azaphenanthrenyl group, a substituted or unsubstituted quinazolinyl group, or a combination thereof, and specific examples thereof may be linking groups of Group 2.

[Group 2]

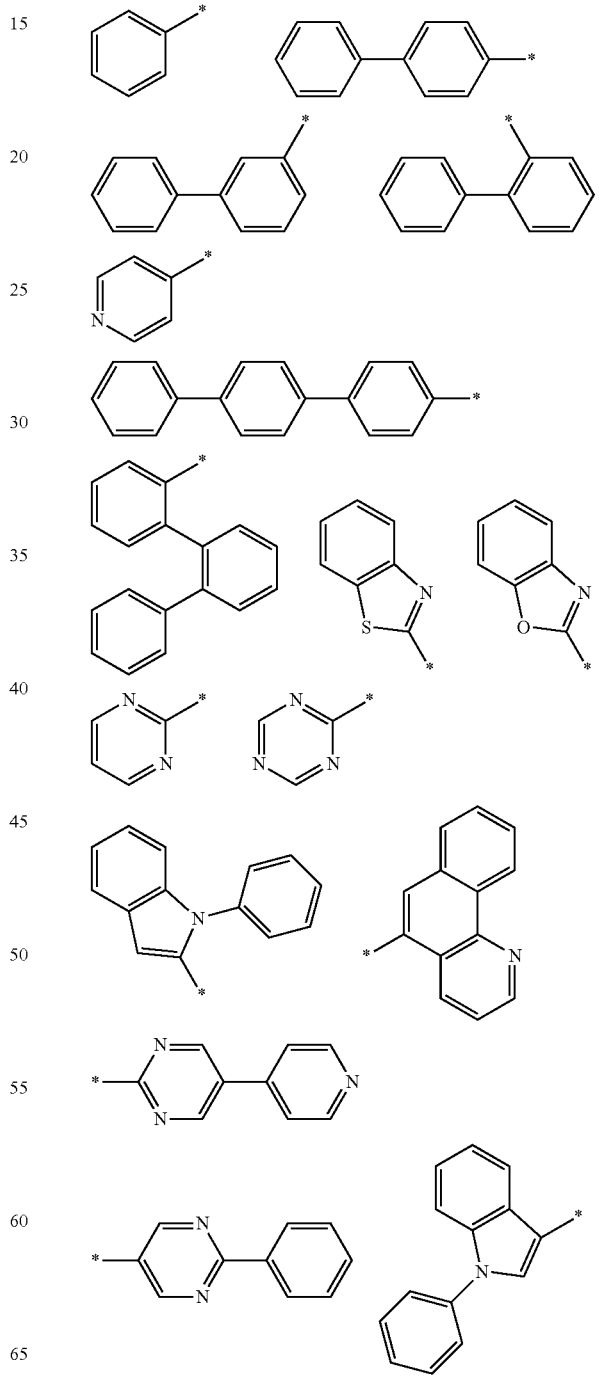

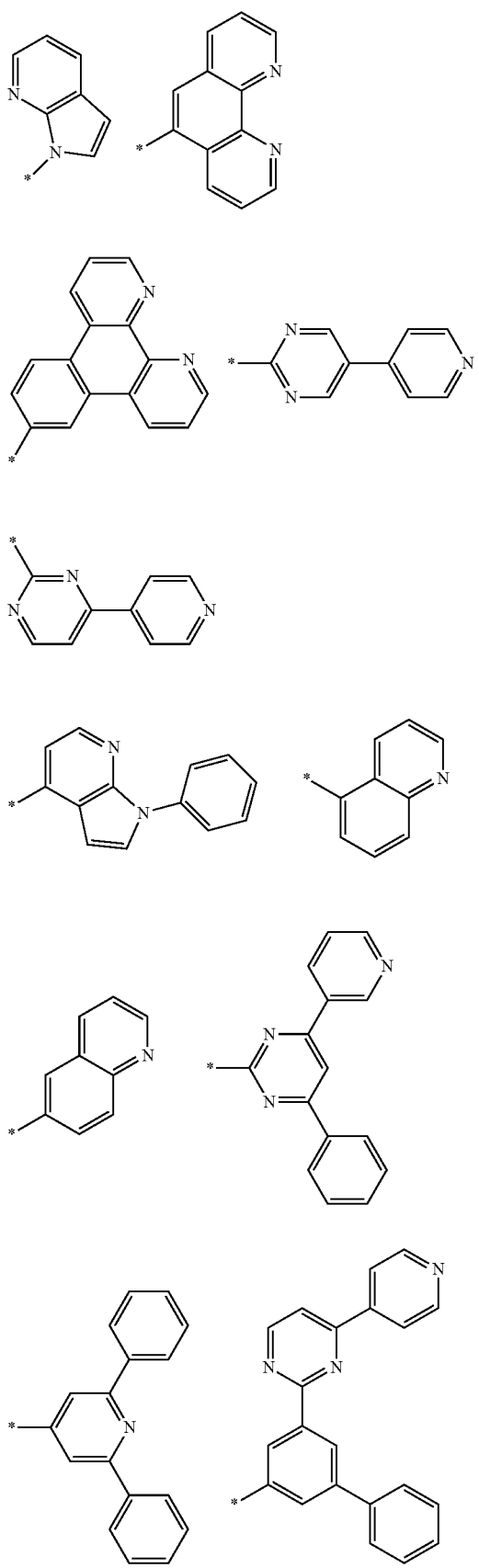
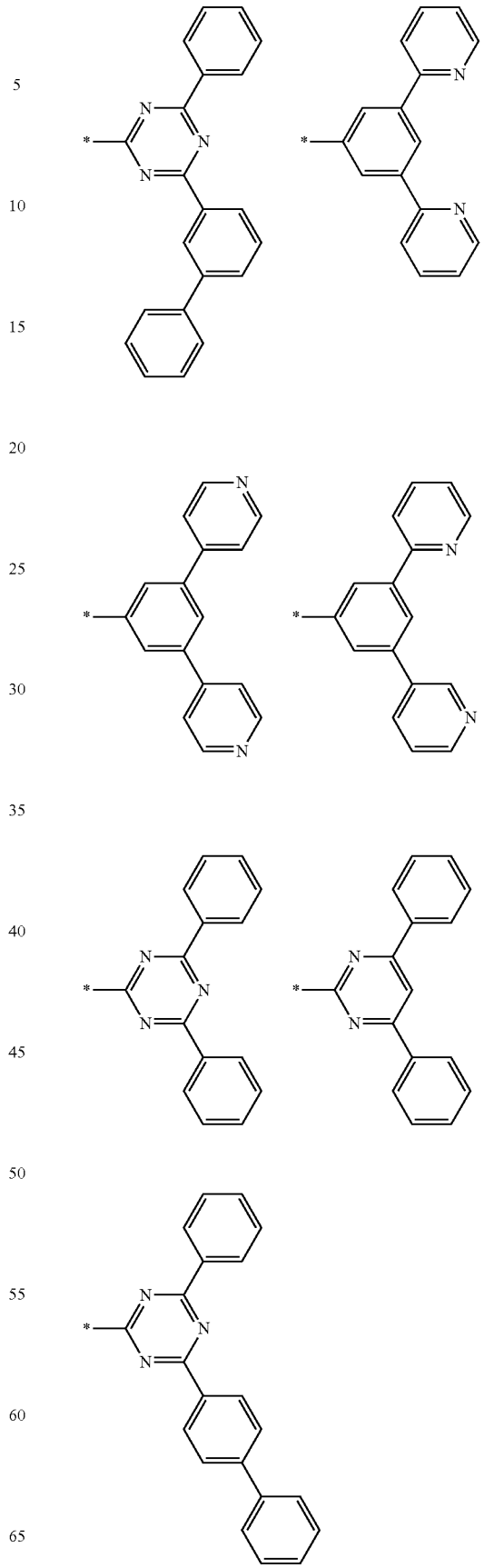

-continued

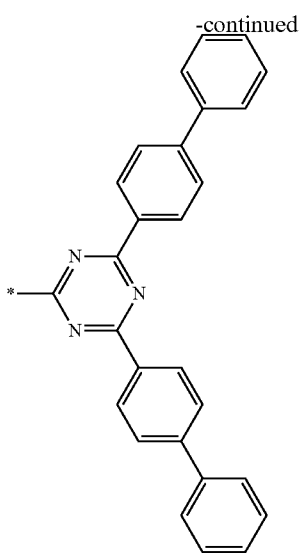

In Group 2, * is a linking site with an adjacent atom.

According to an embodiment, $R^1$ to $R^{12}$ of Chemical Formula I may independently be hydrogen, deuterium, a substituted or unsubstituted C1 to C10 alkyl group, a substituted or unsubstituted C6 to C20 aryl group, a substituted or unsubstituted C2 to C30 heteroaryl group, or a combination thereof, and specifically hydrogen, deuterium, or a substituted or unsubstituted C6 to C30 aryl group.

According to an embodiment, $R^1$ to $R^{12}$ of Chemical Formula I may independently be hydrogen, deuterium, a substituted or unsubstituted phenyl group, a substituted or unsubstituted naphthyl group, a substituted or unsubstituted biphenyl group, a substituted or unsubstituted terphenyl group, or a substituted or unsubstituted triphenylene group.

For example, $R^1$, $R^2$, and $R^5$ to $R^{12}$ may be all hydrogen, $R^3$ and $R^4$ may independently be hydrogen, a phenyl group, a biphenyl group, or a terphenyl group.

The compound for an organic optoelectric device may be, for example selected from compounds of Group 3, but is not limited thereto.

[Group 3]

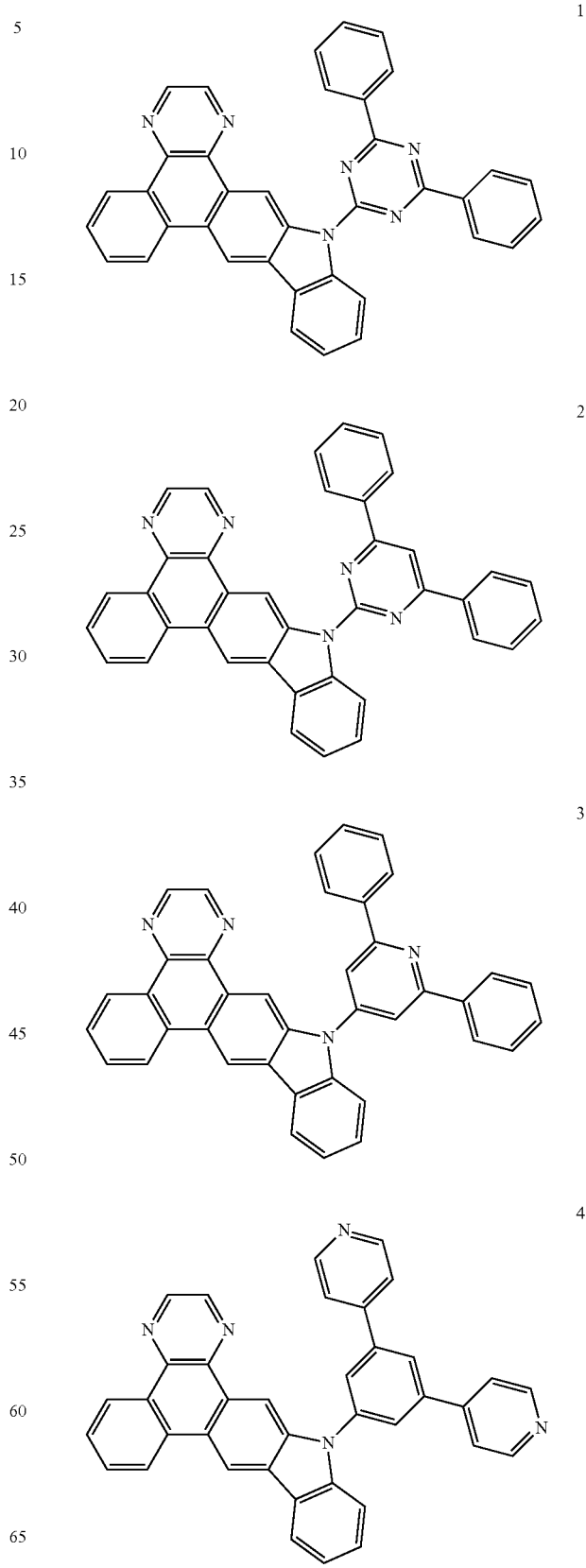

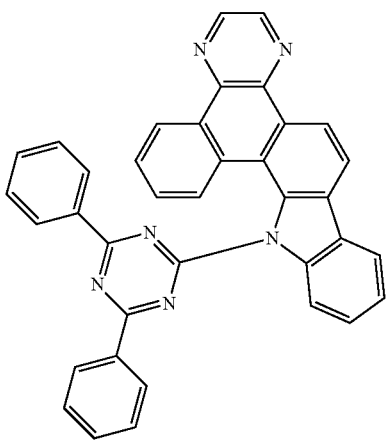
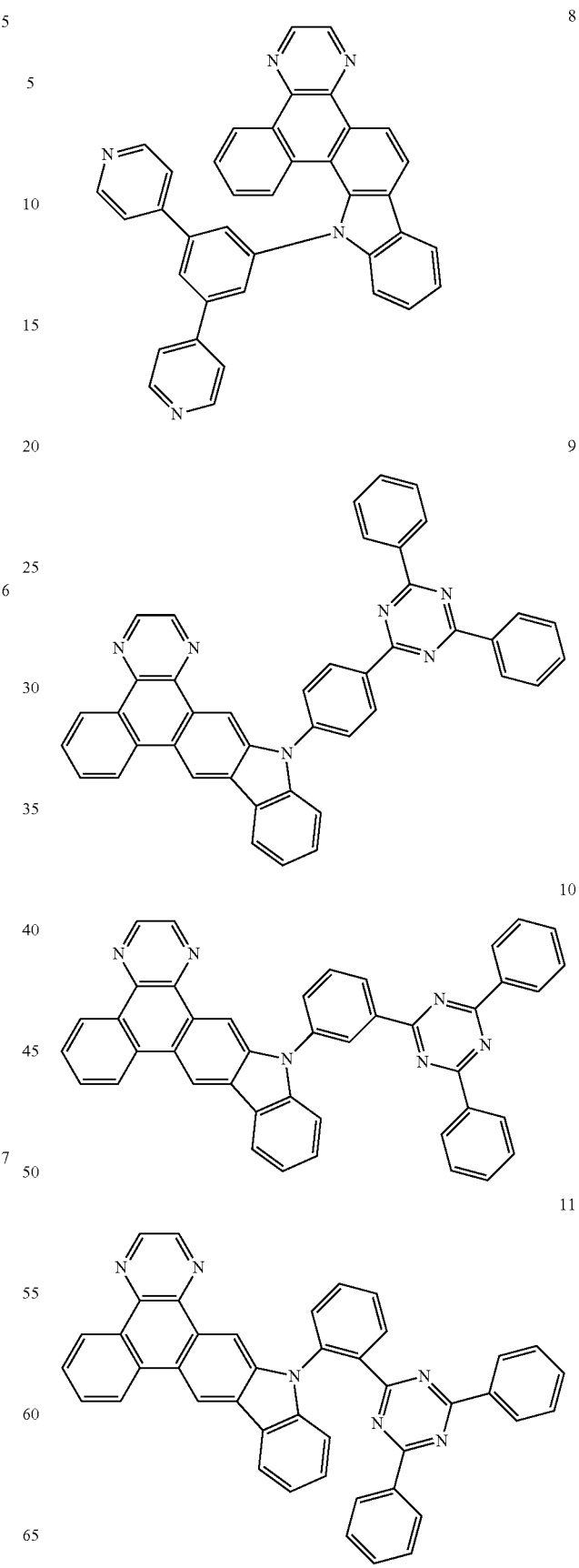

12
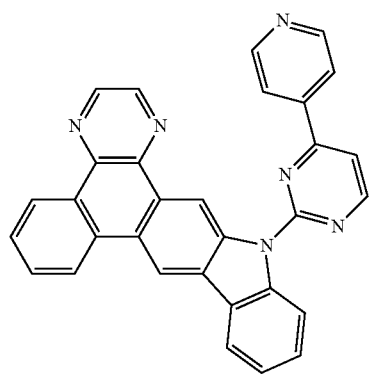
13
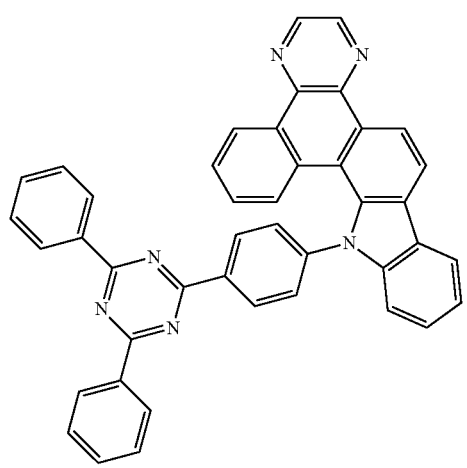
14
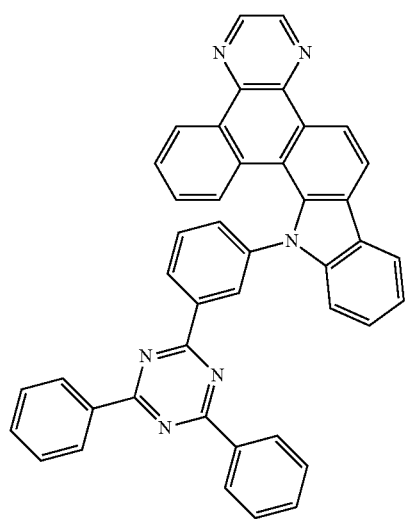
15
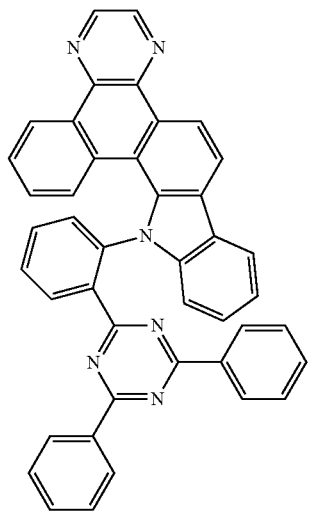
16
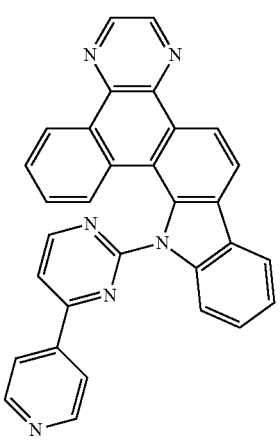
17
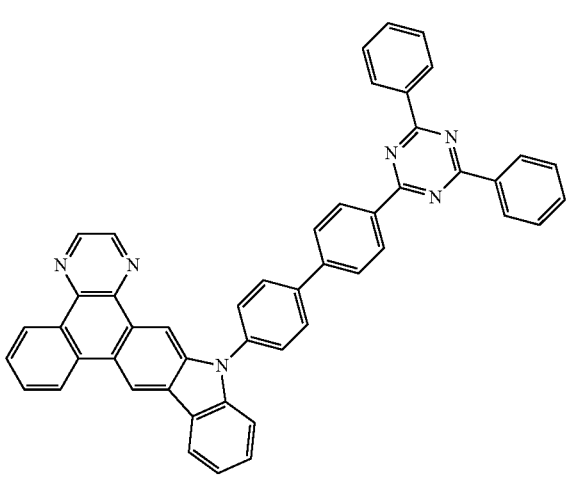

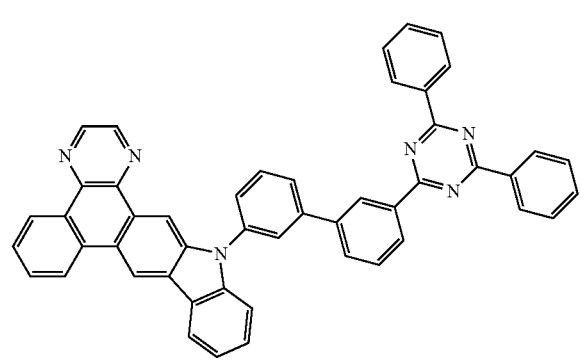
18
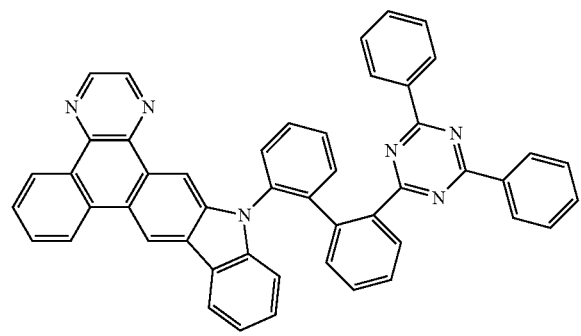
19
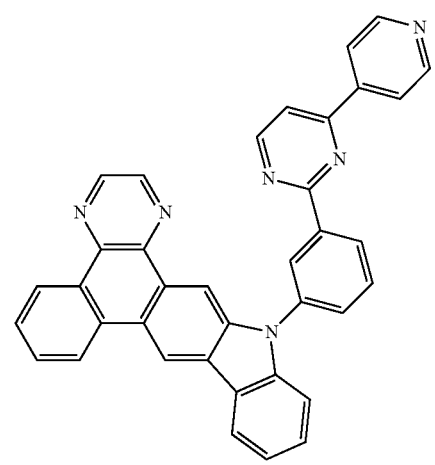
20
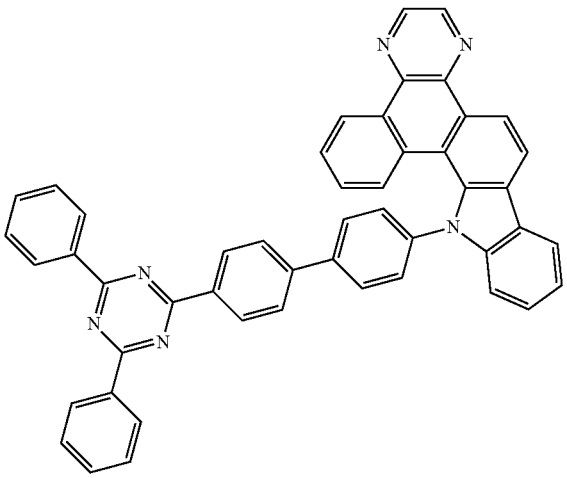
21
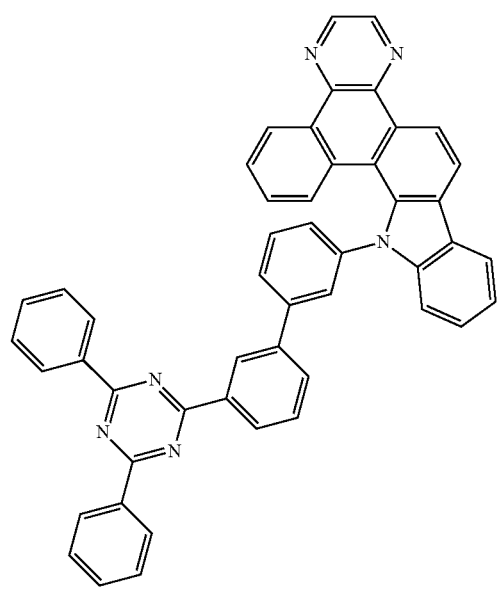
22
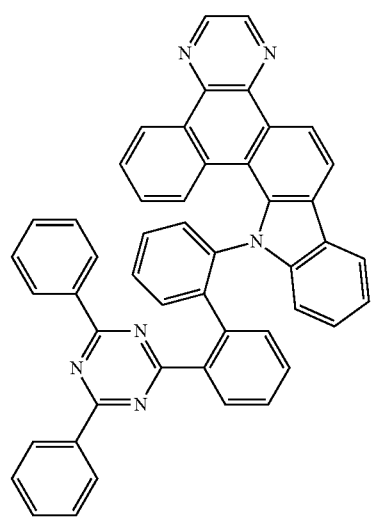
23

24
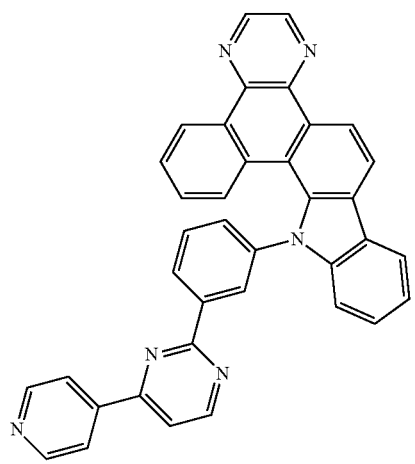
27
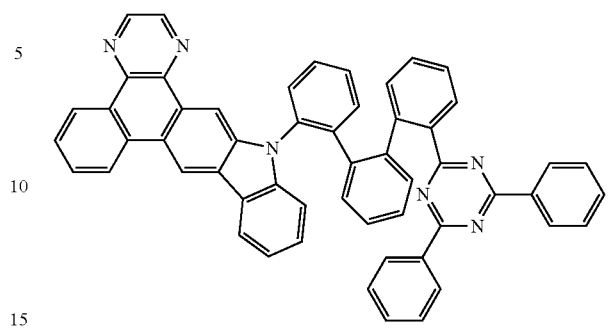
25
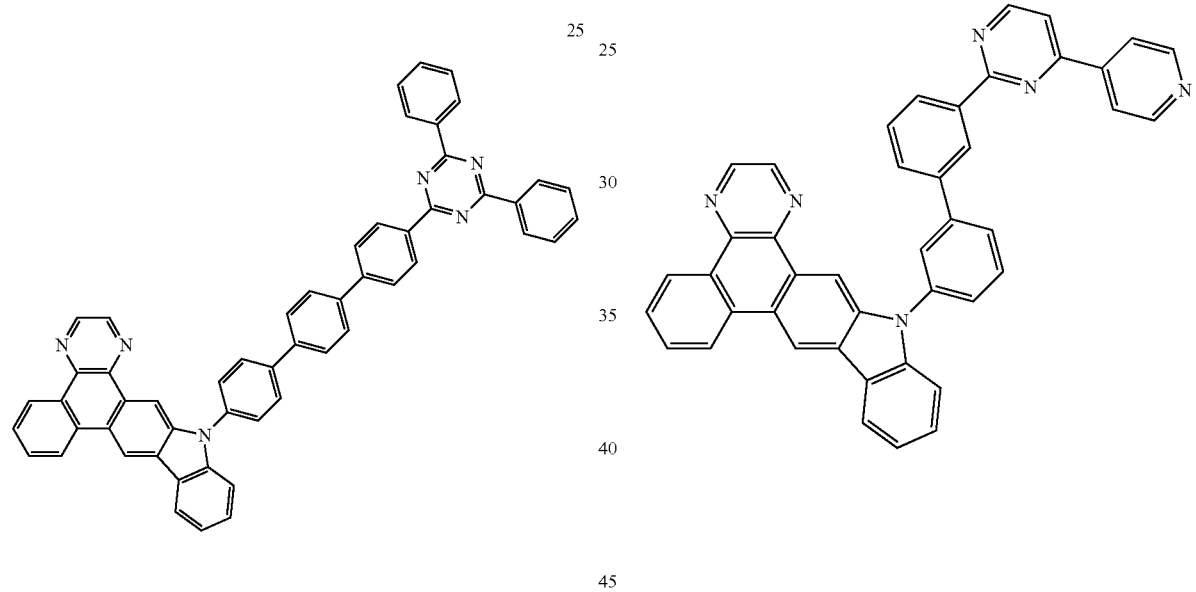
28
26
29
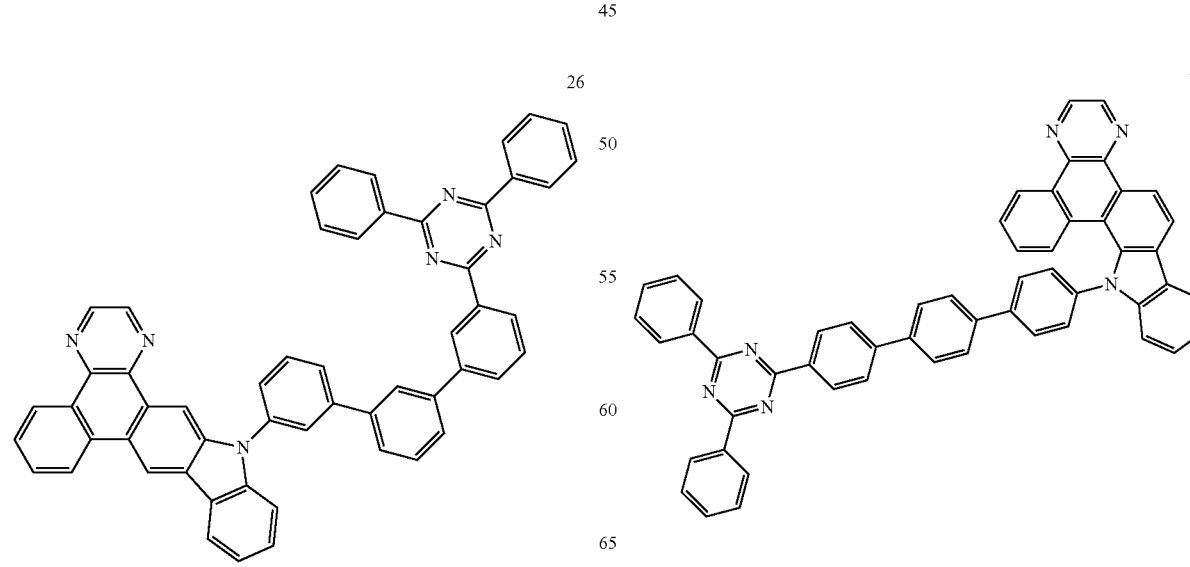

30
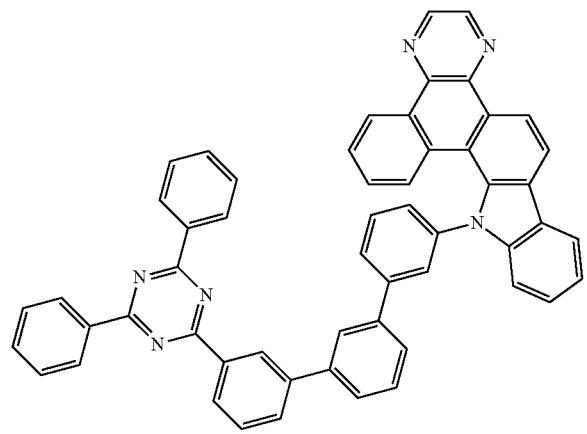
31
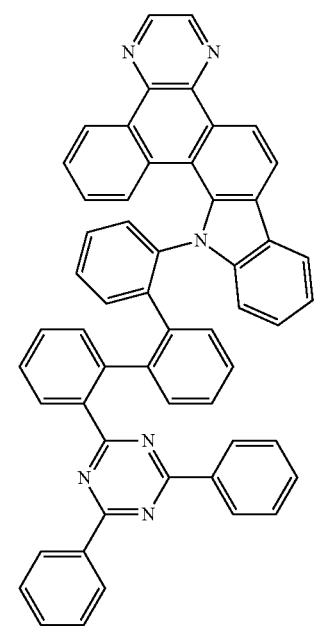
32
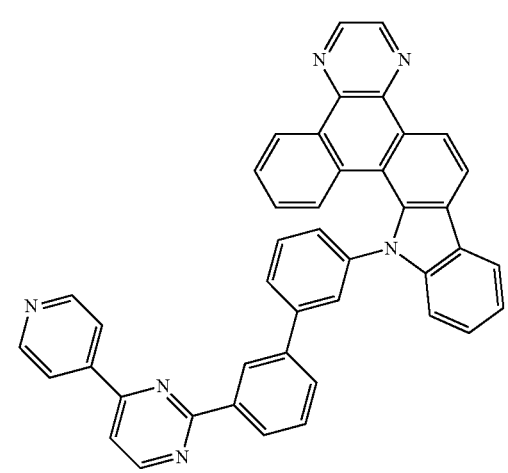
33
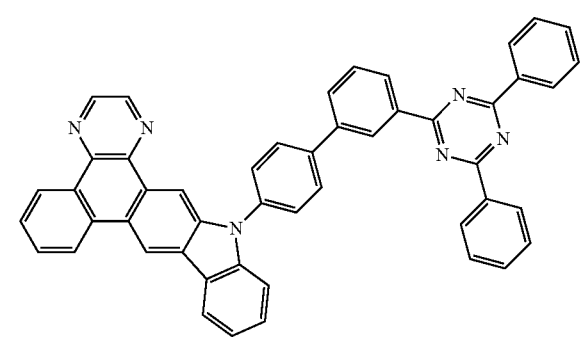
34
35
36
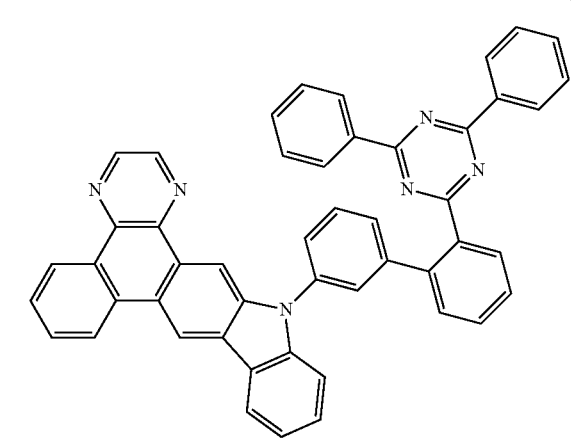

37
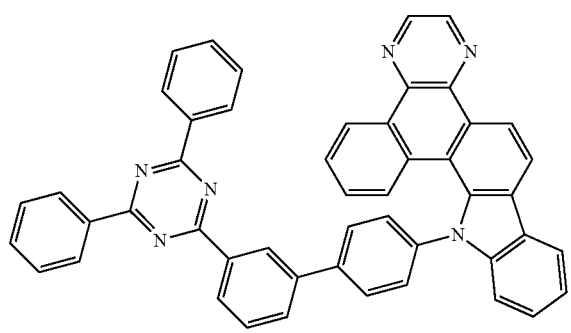
38
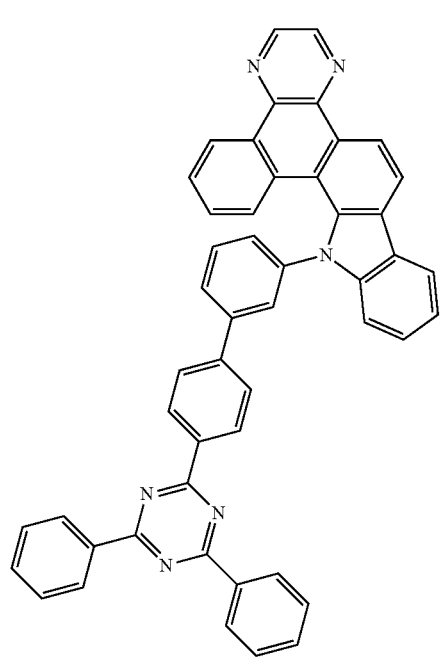
39
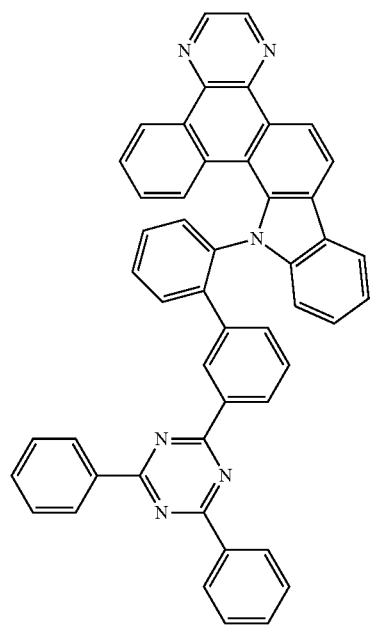
40
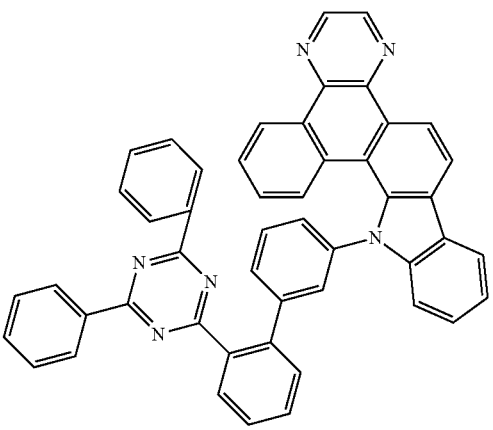
41
42
43
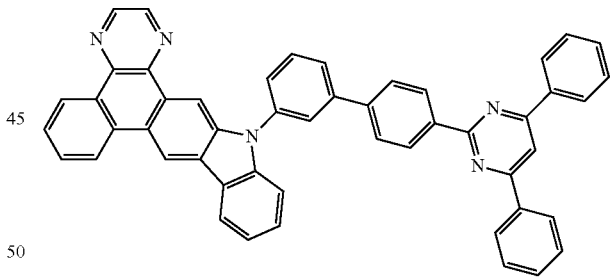
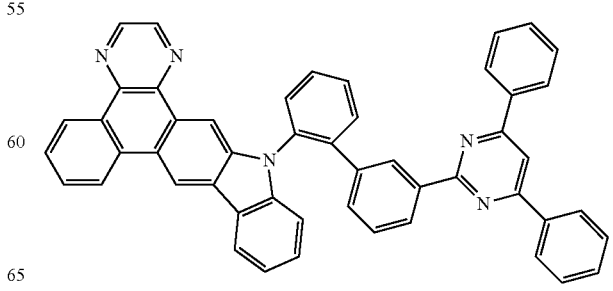

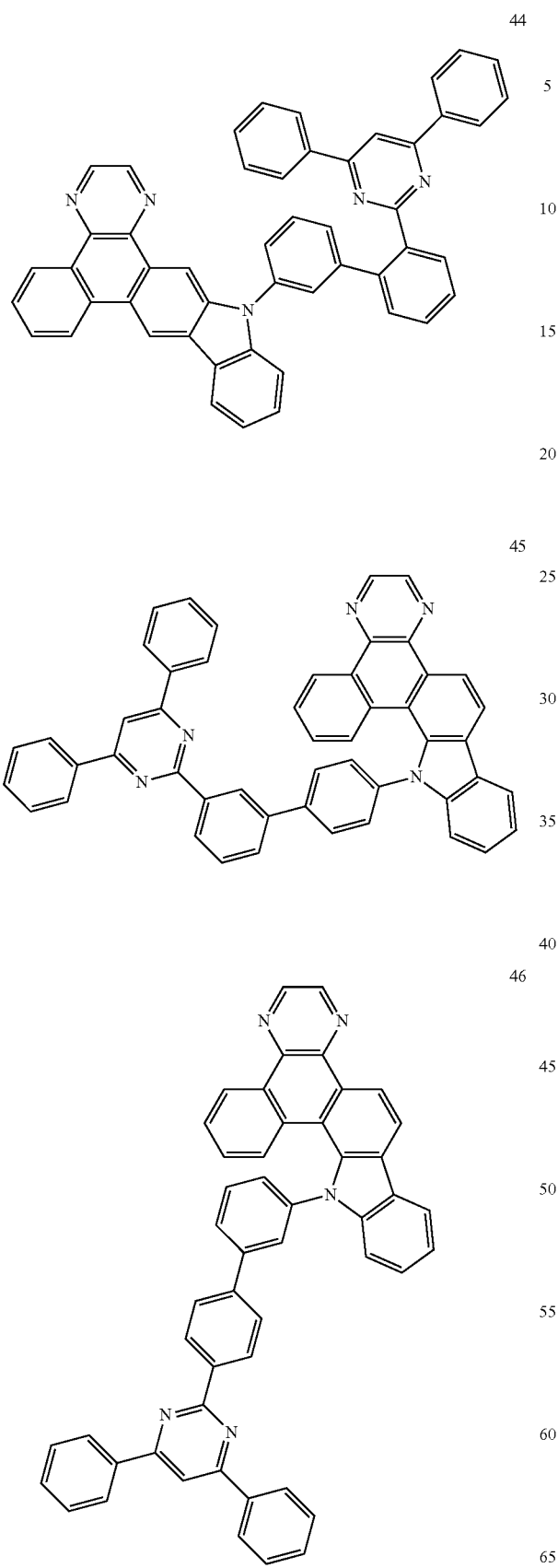
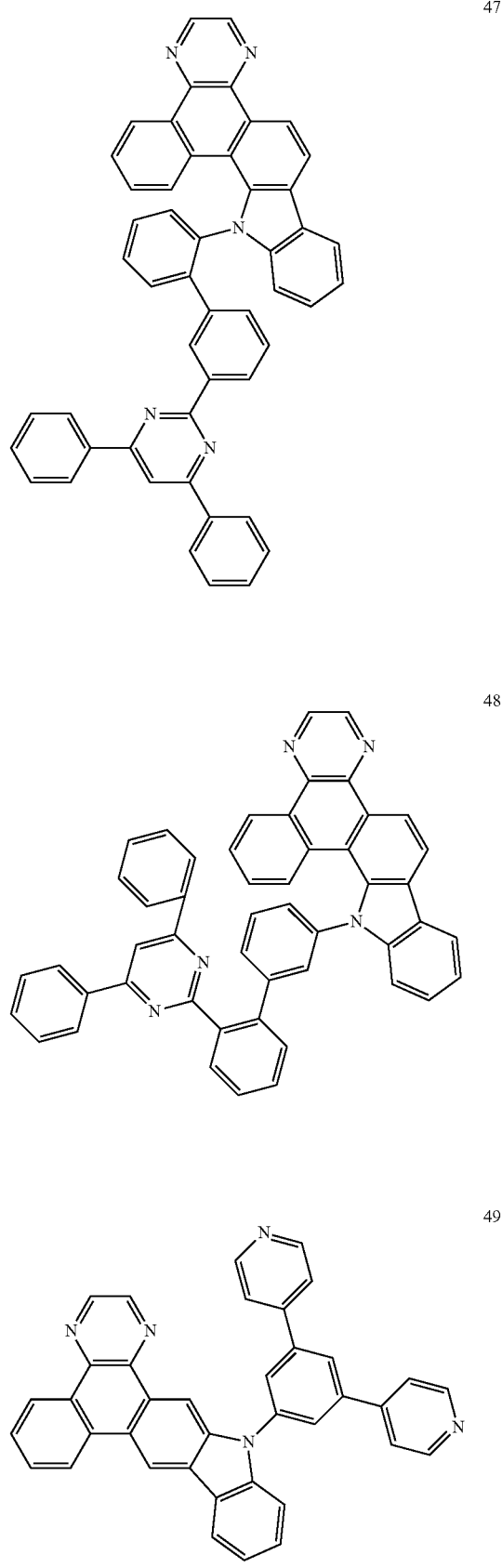

-continued
50
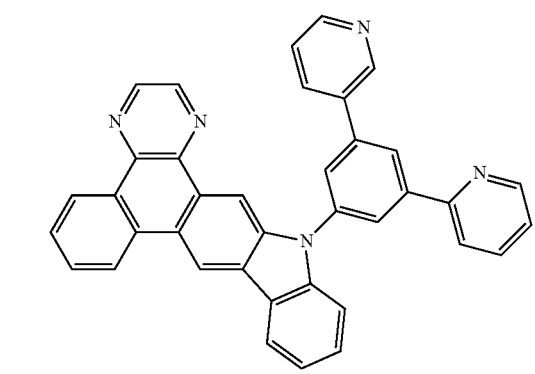
51
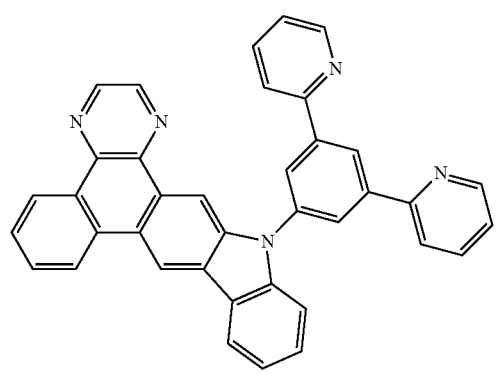
52
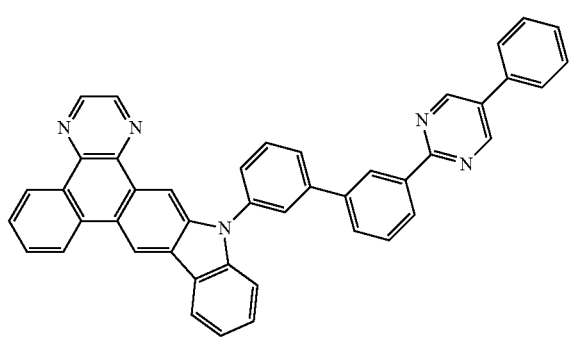
53
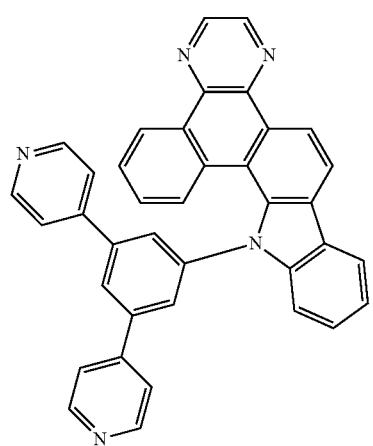
-continued
54
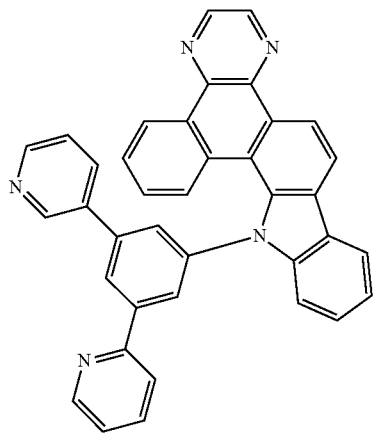
55
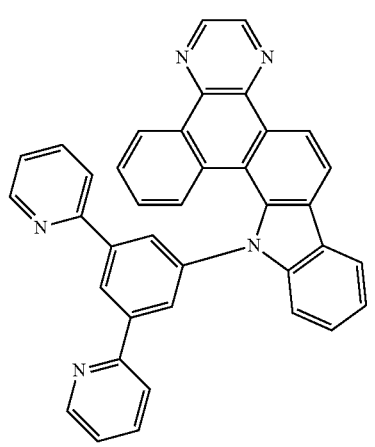
56
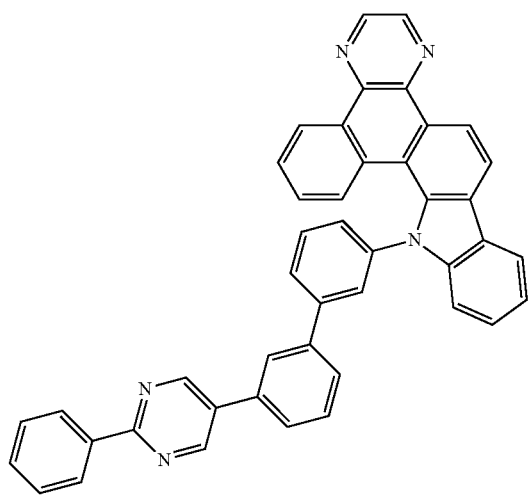

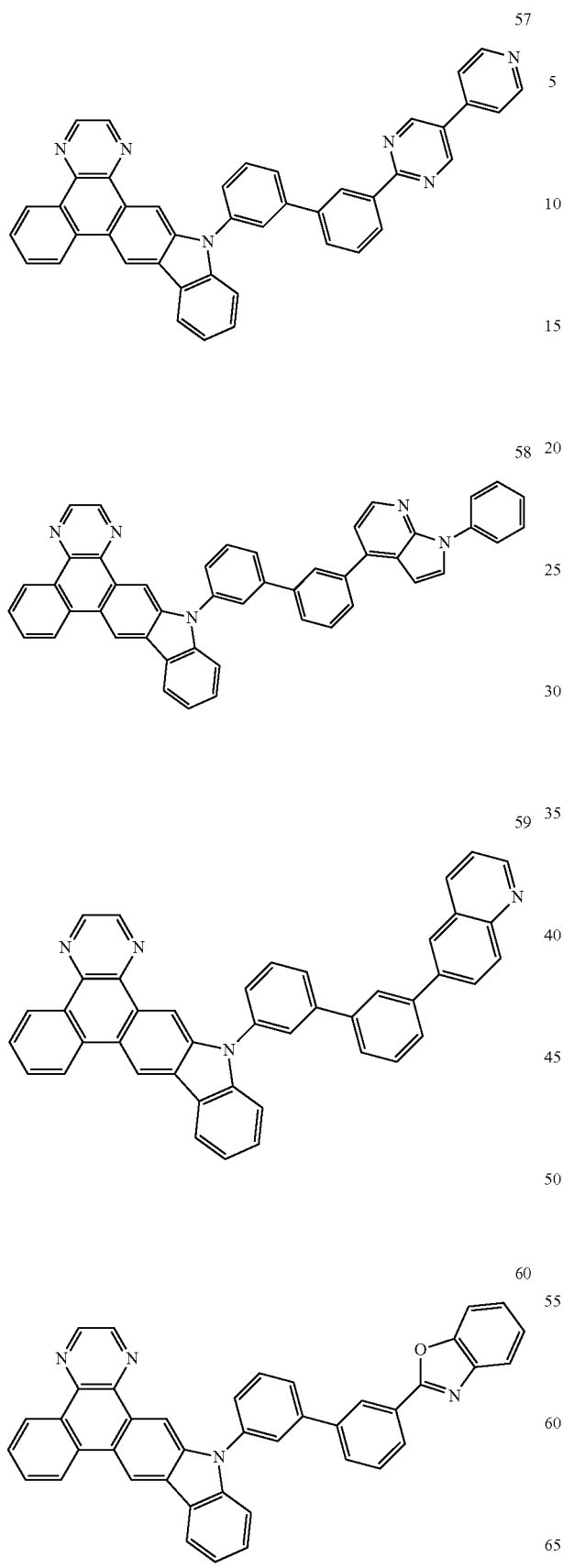
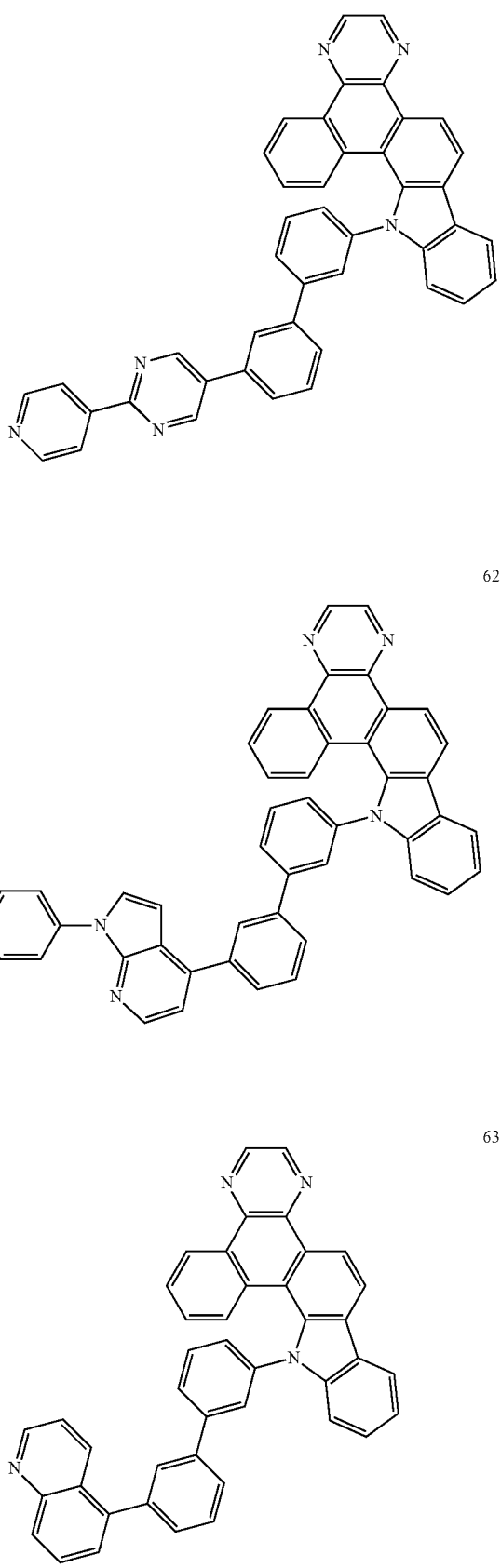

-continued
64
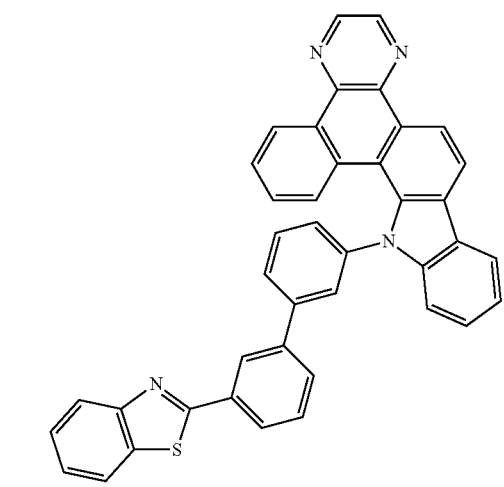
65
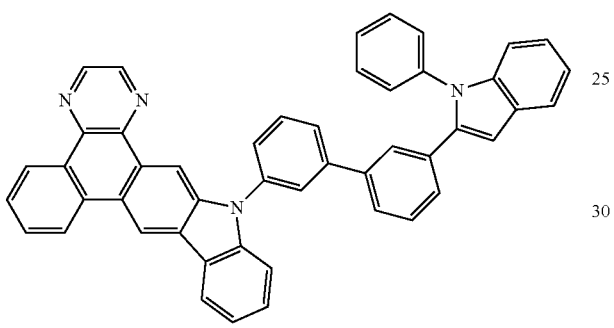
66
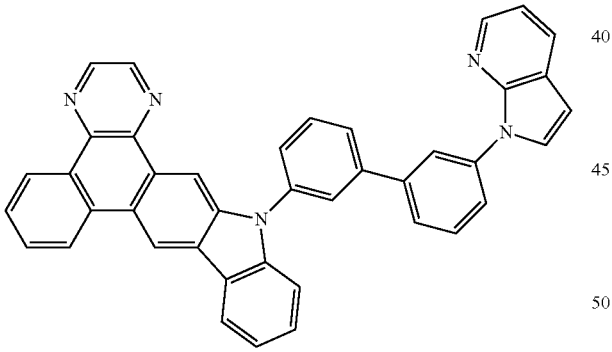
67
-continued
68
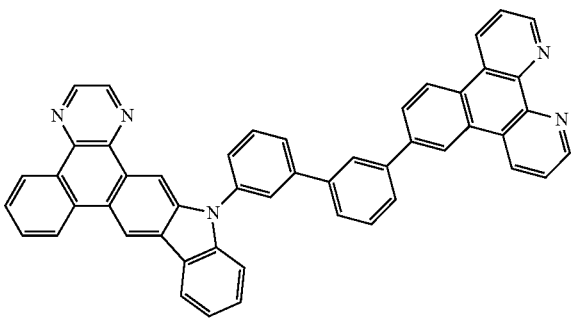
69
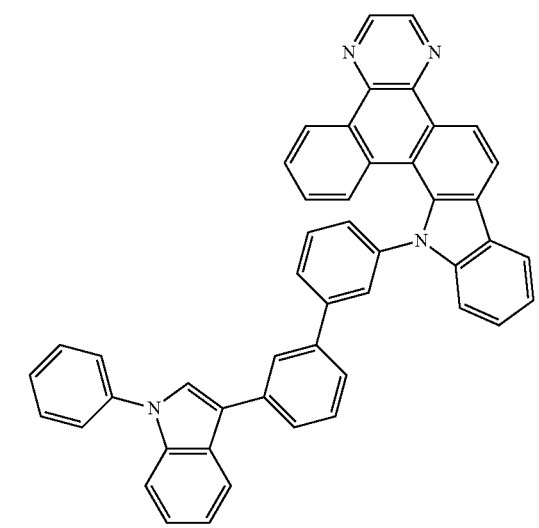
70
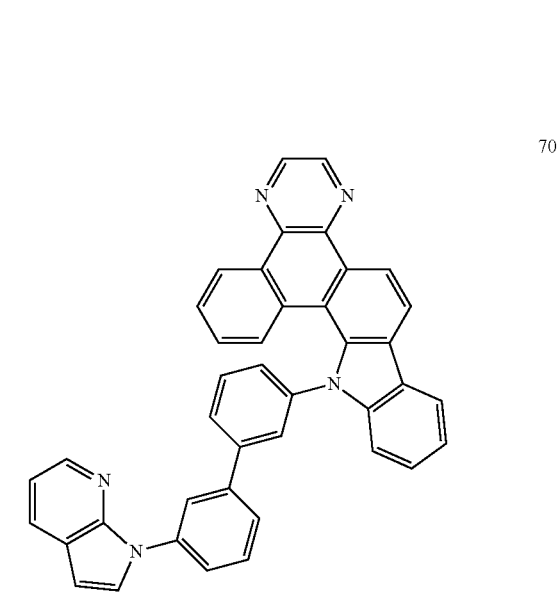

71
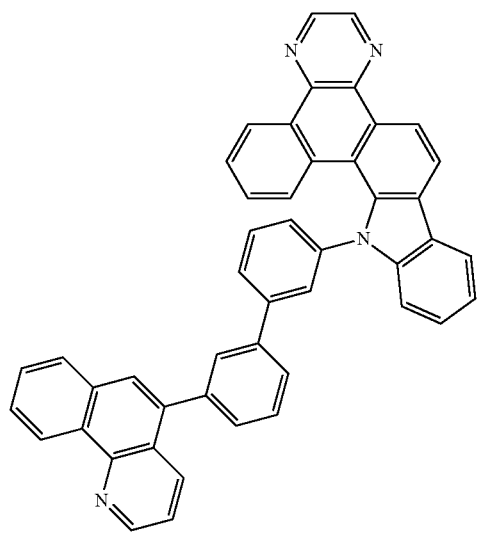
72
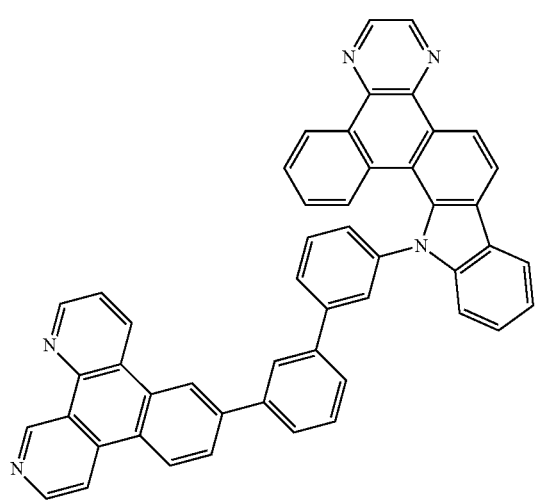
73
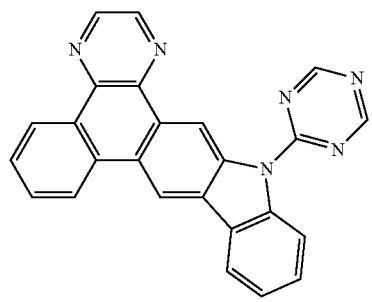
74
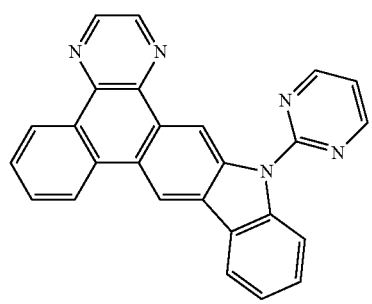
75
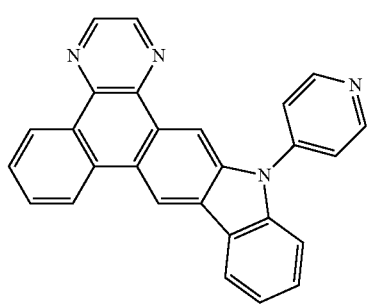
76
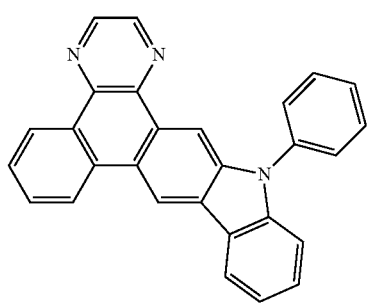
77
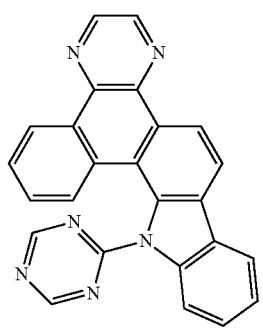
78
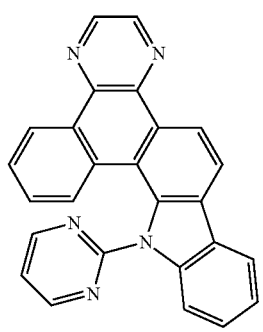
79
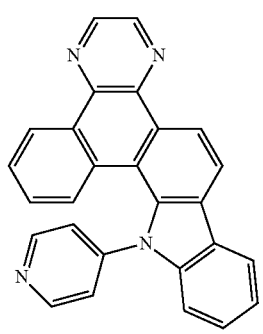

80
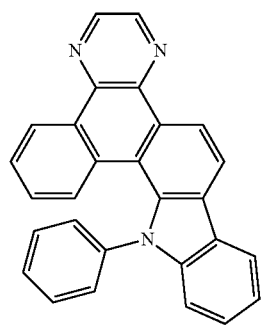
81
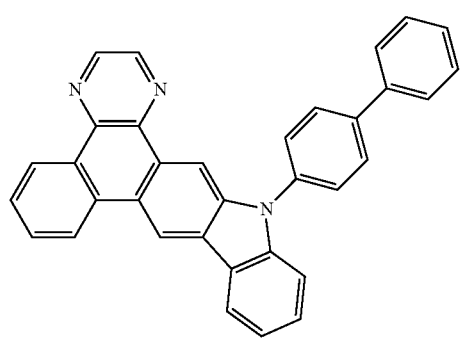
82
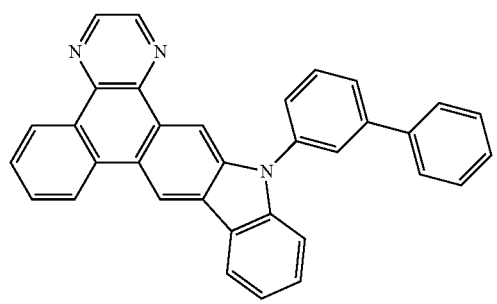
83
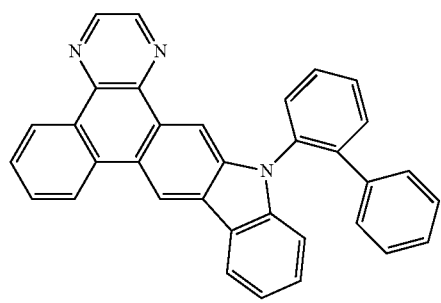
84
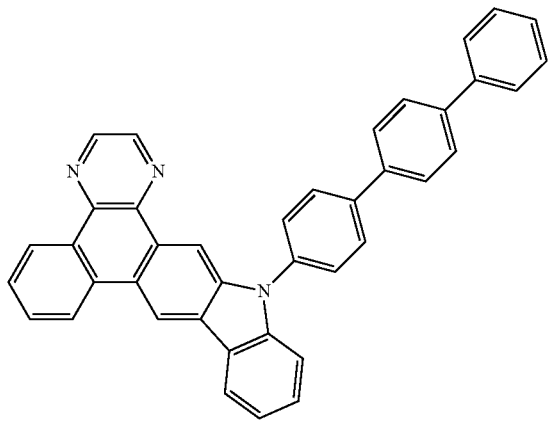
85
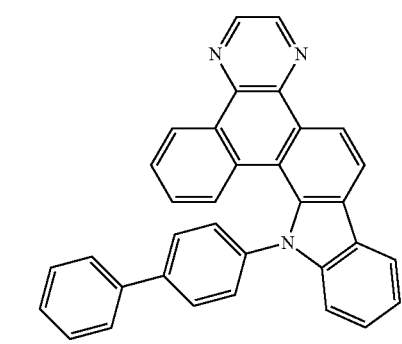
86
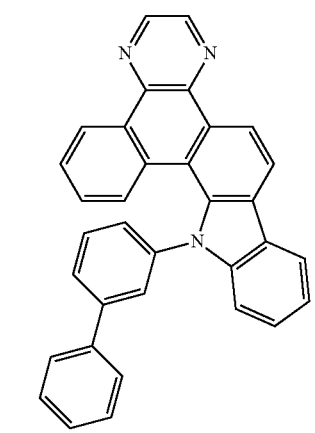
87
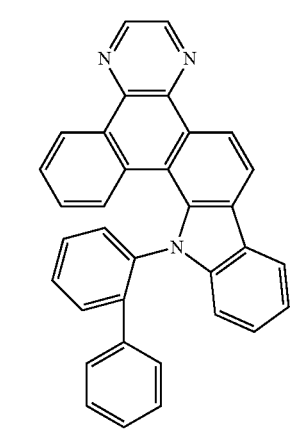

88
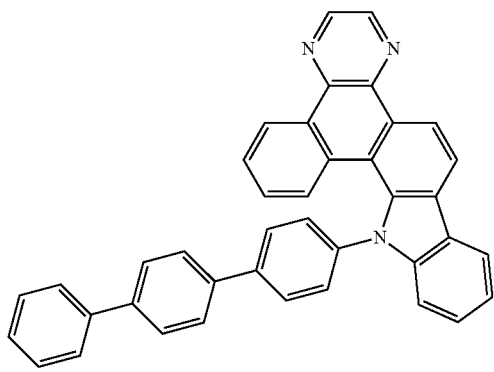
89
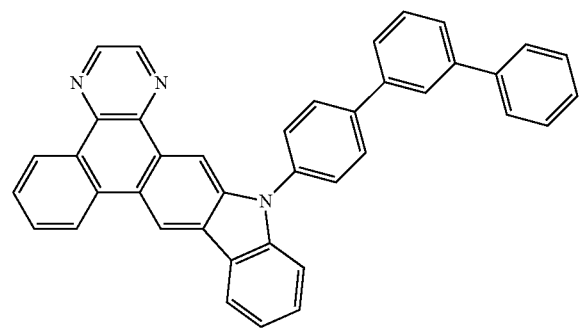
90
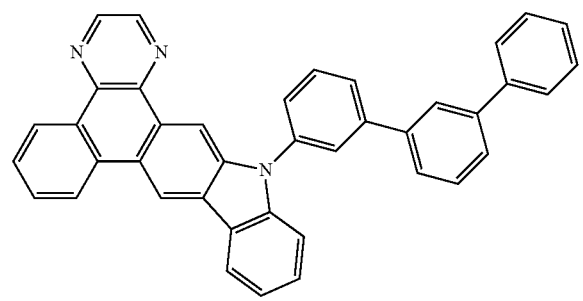
91
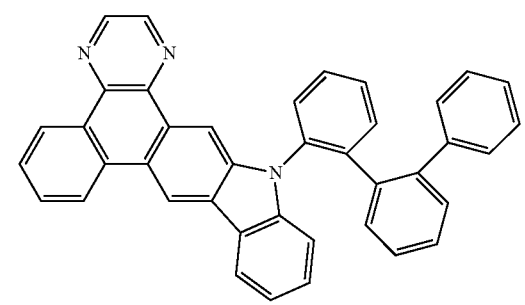
92
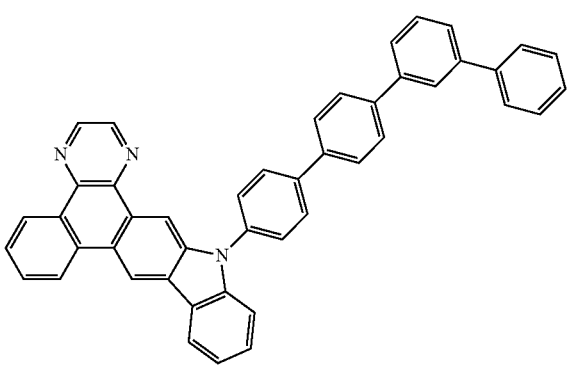
93
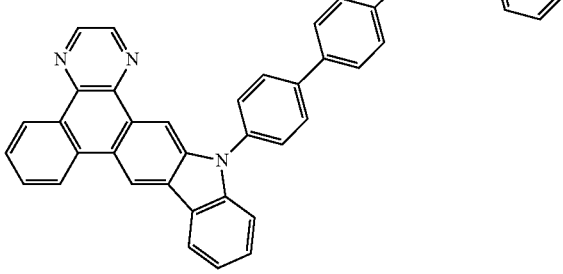
94
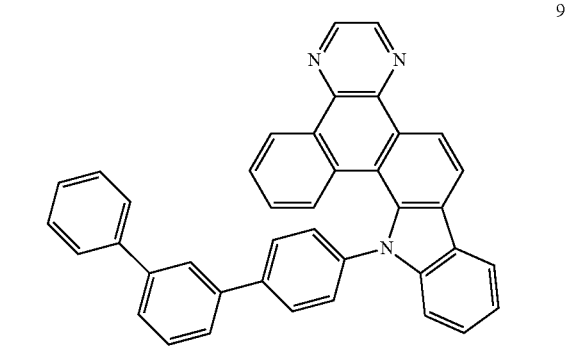
95
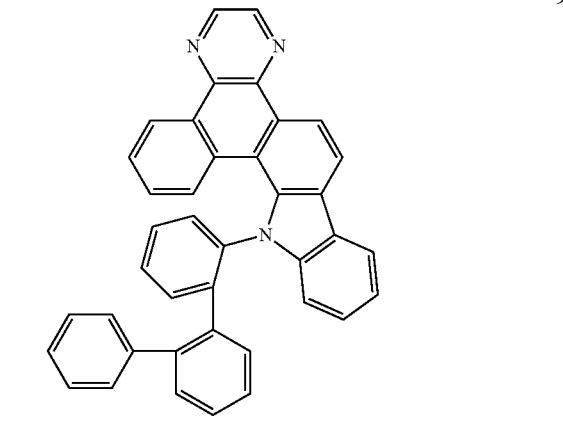

96
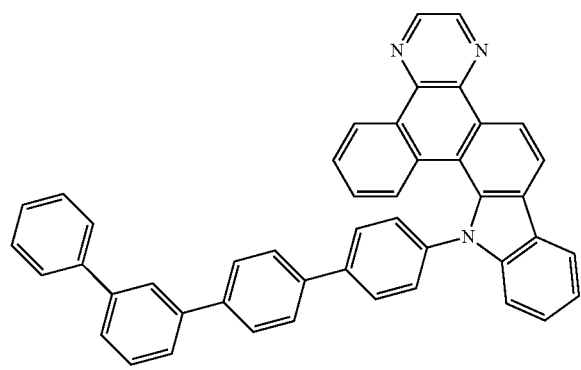
97
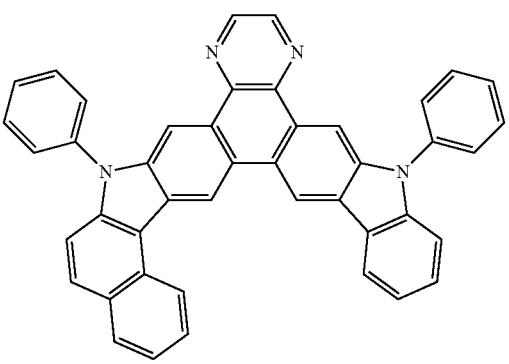
98
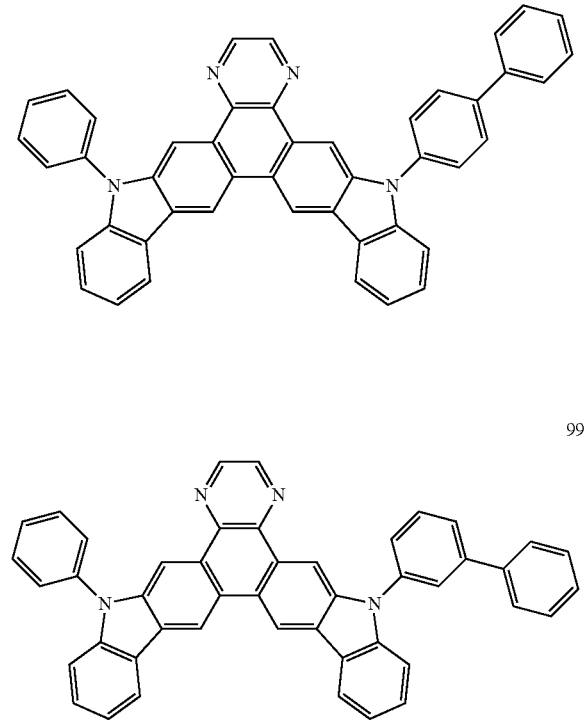
99
100
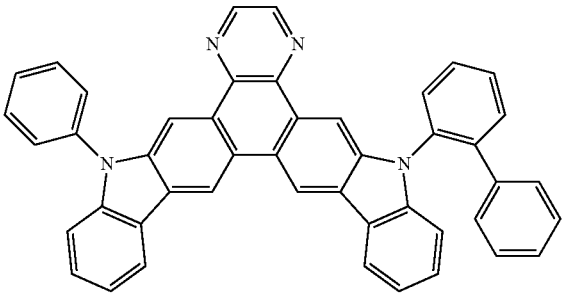
101
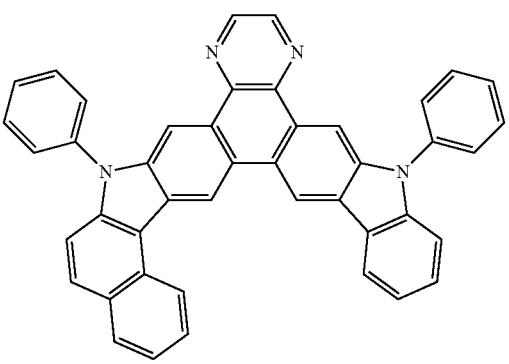
102
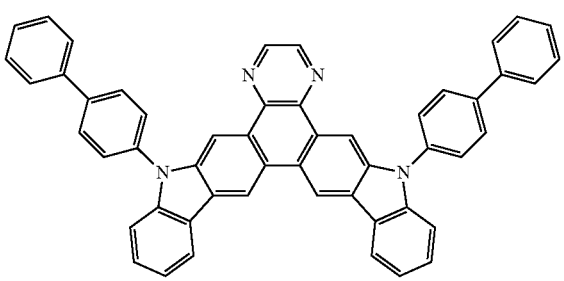
103
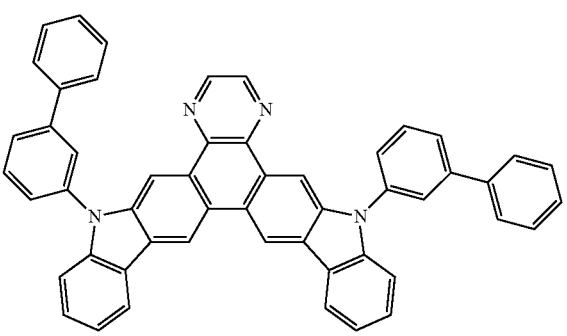
104
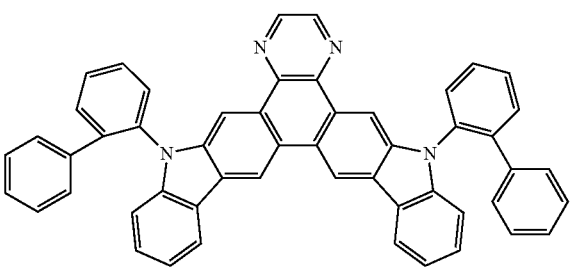

105
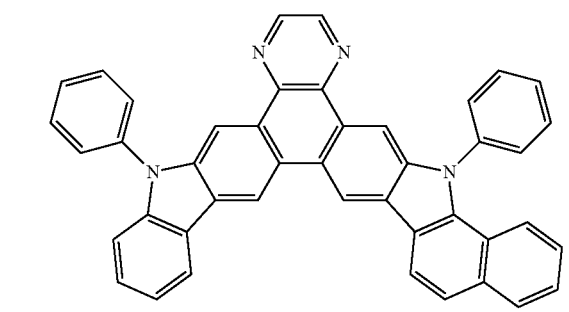
106
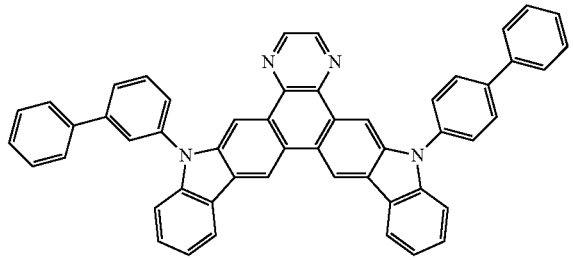
107
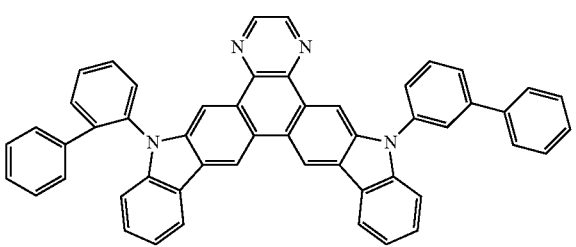
108
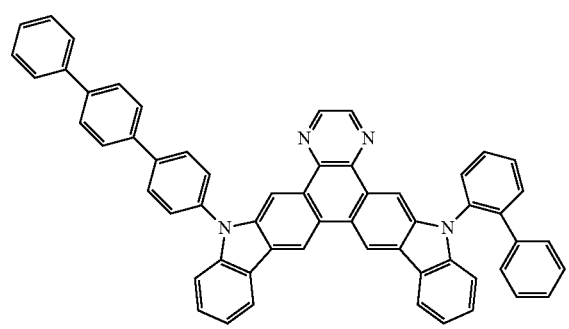
109
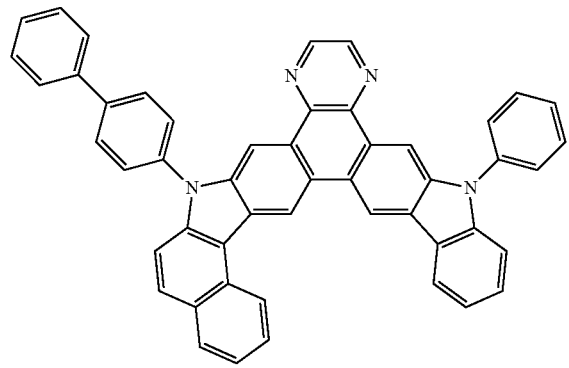
110
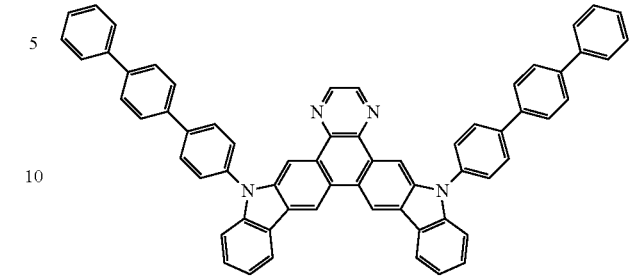
111
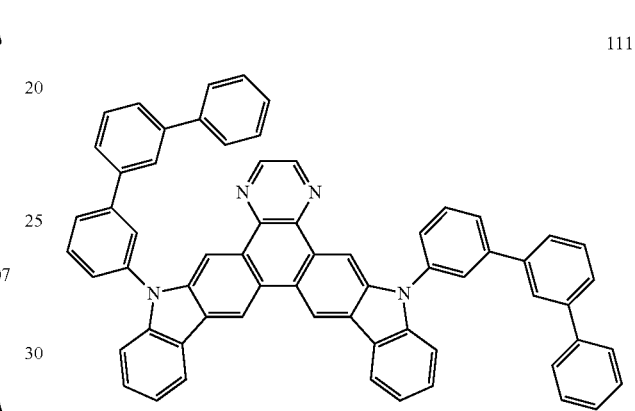
112
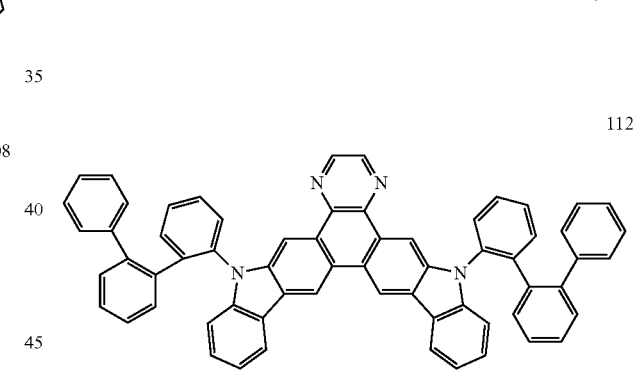
113
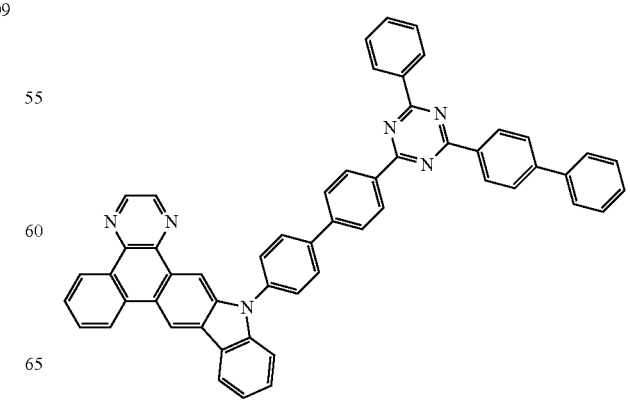

114
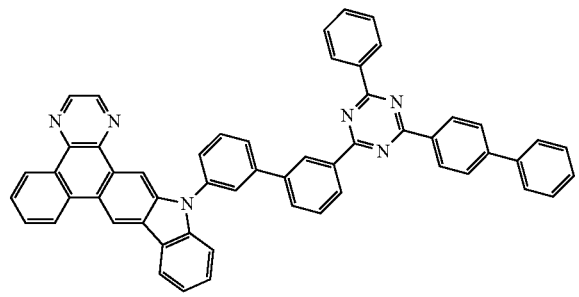
115
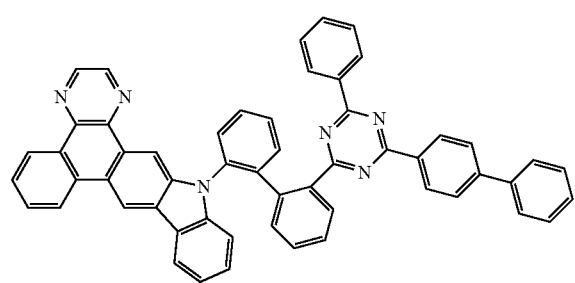
116
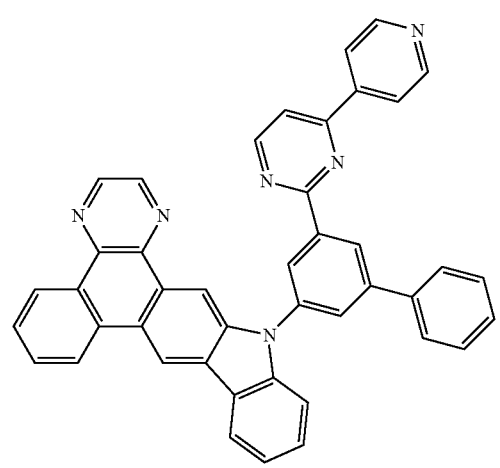
117
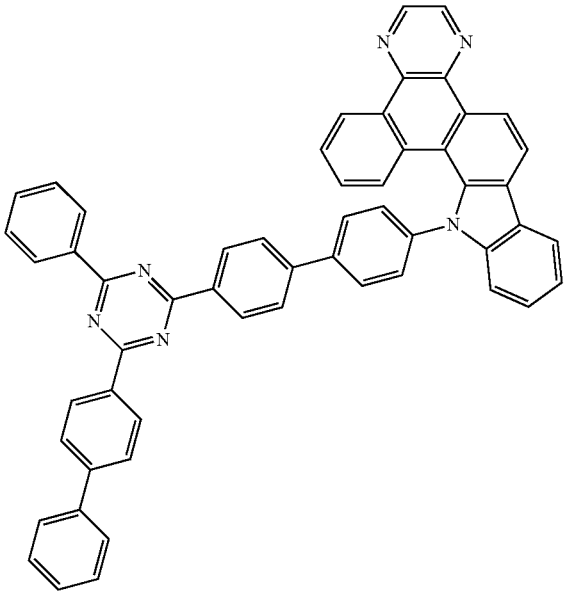
118
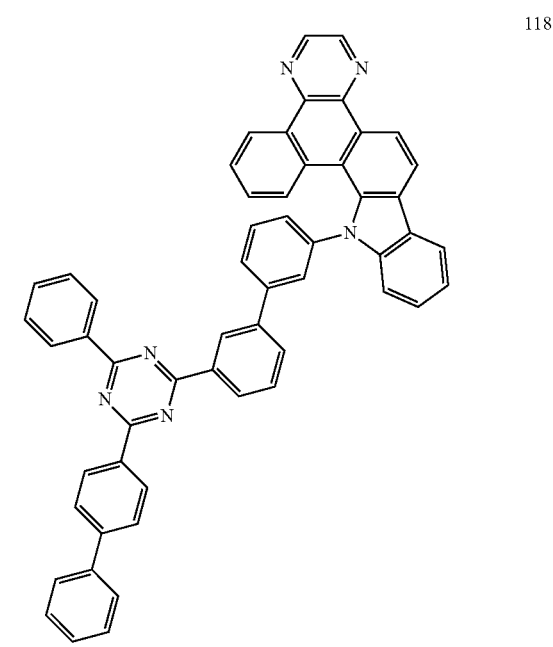

119
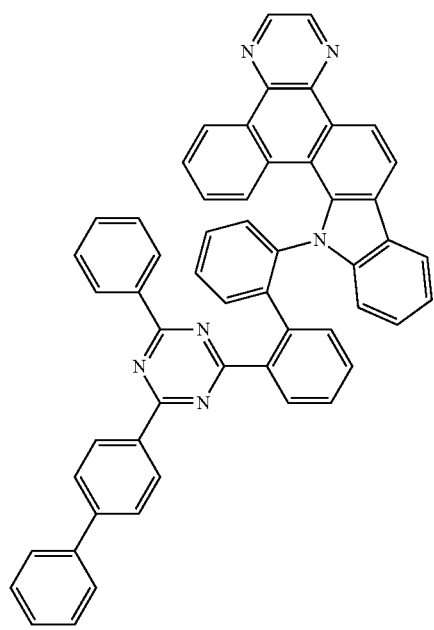
120
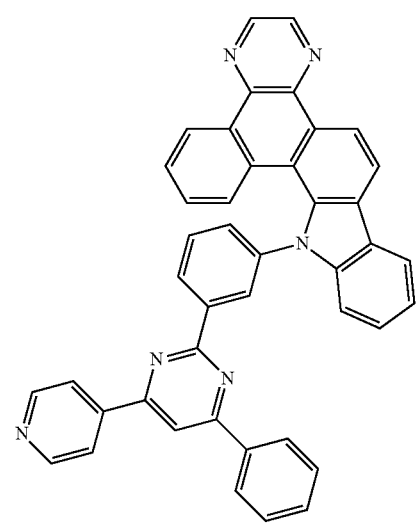
121
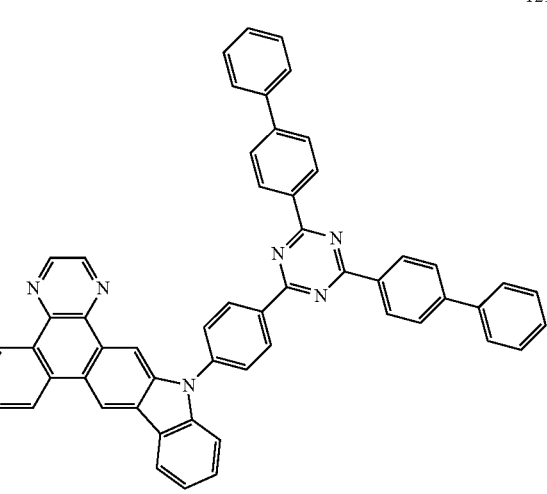
122
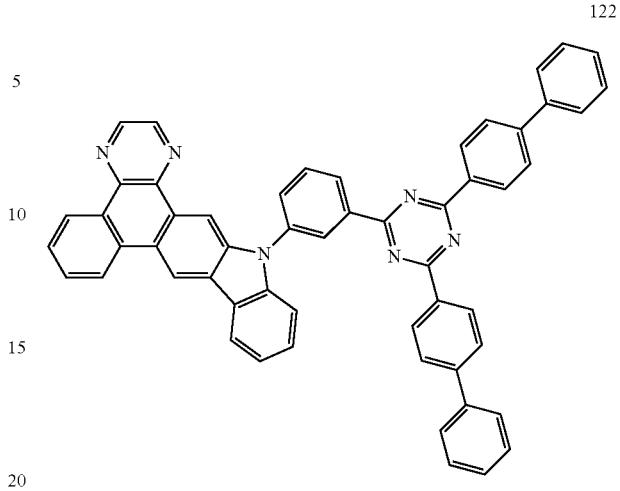
123
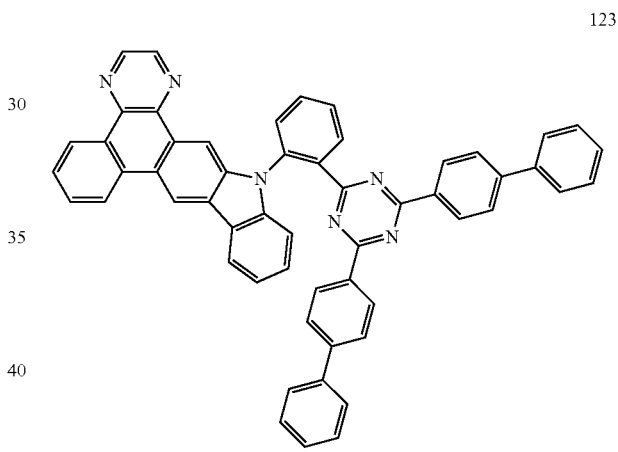
124
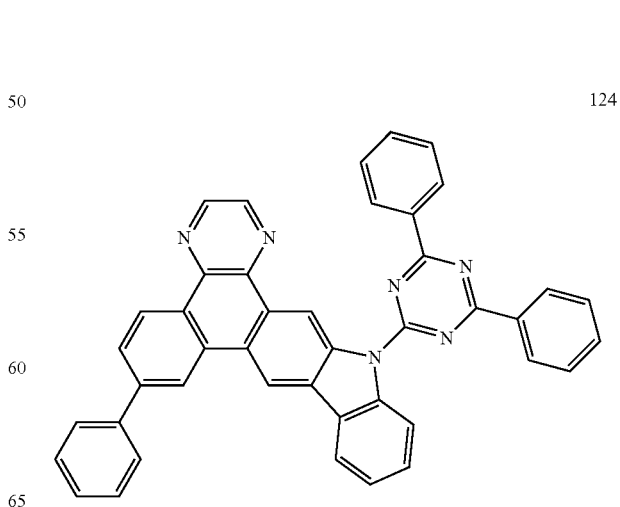

125
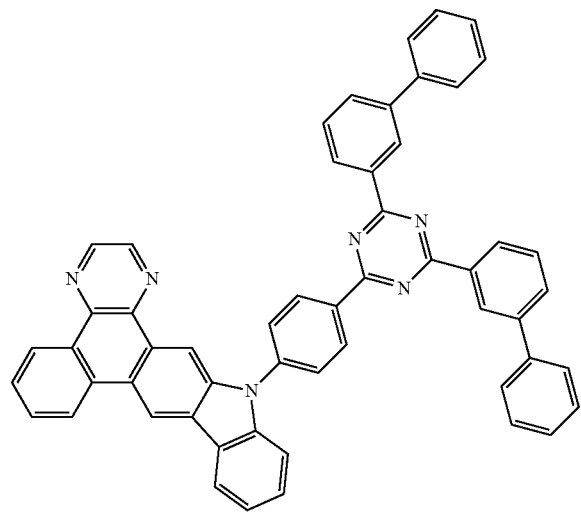
126
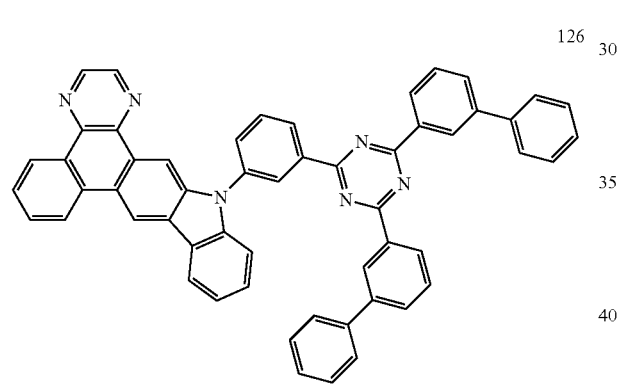
127
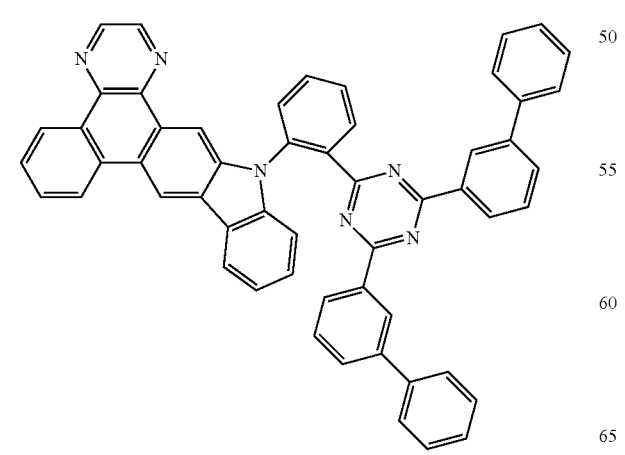
128
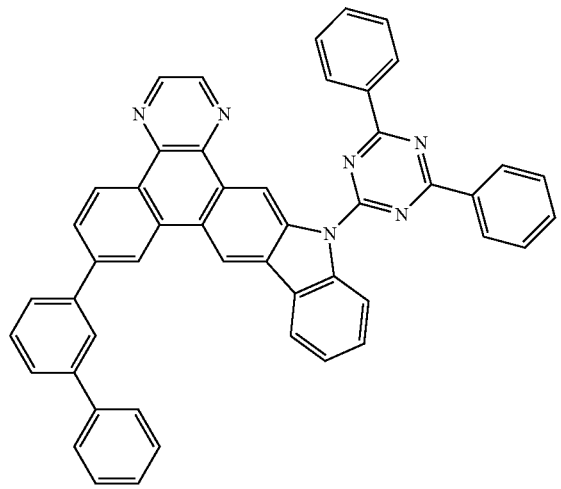
129
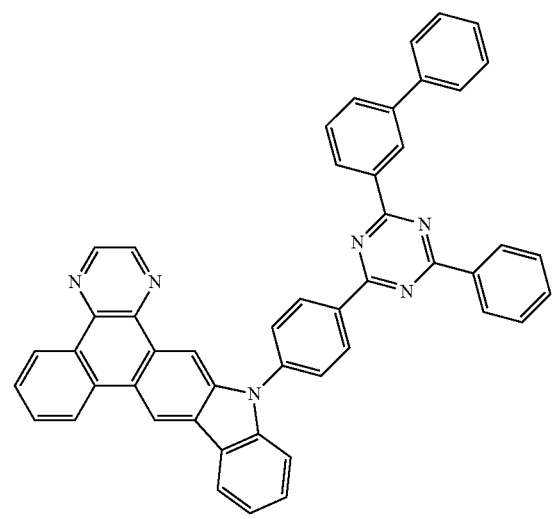
130
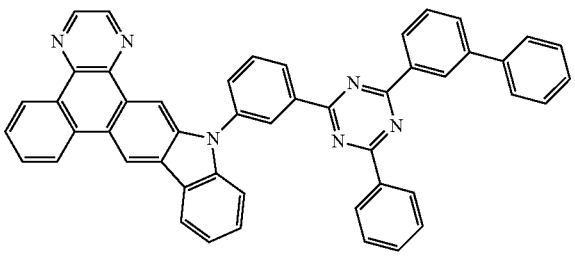

131
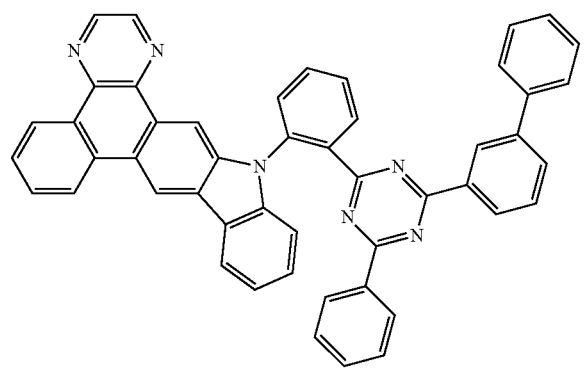
132
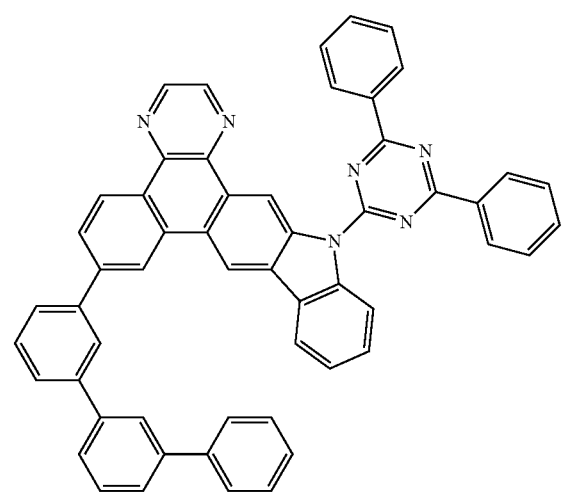
133
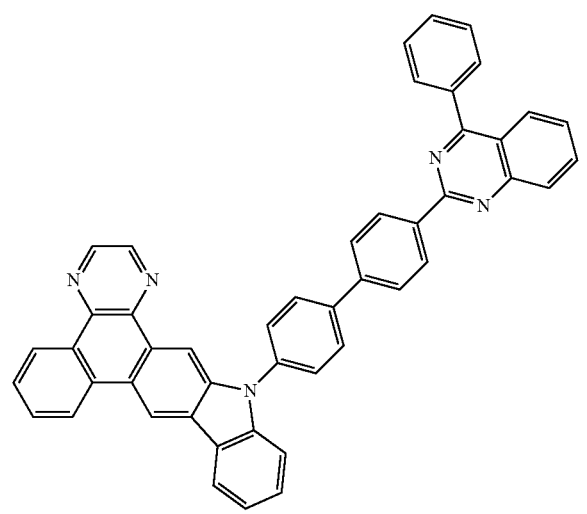
134
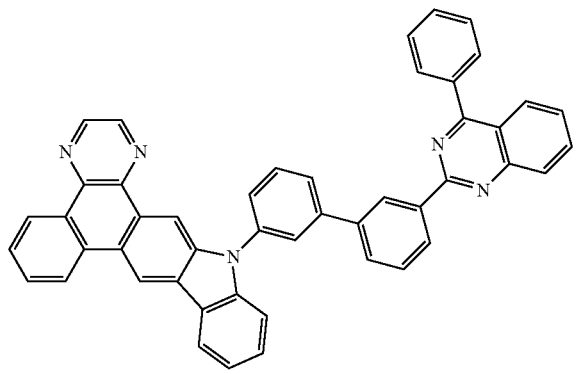
135
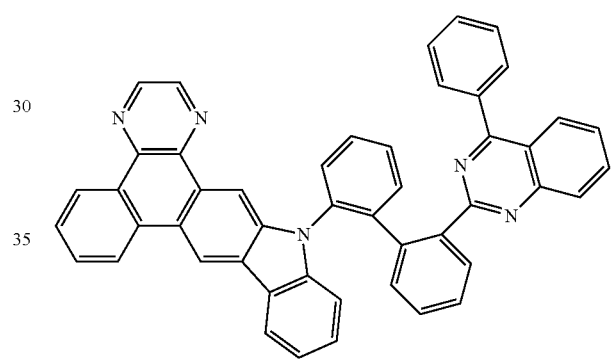
136
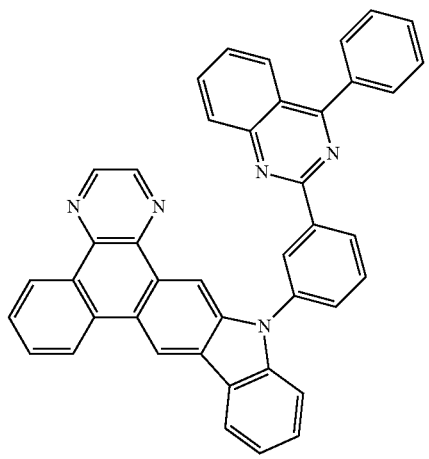

137
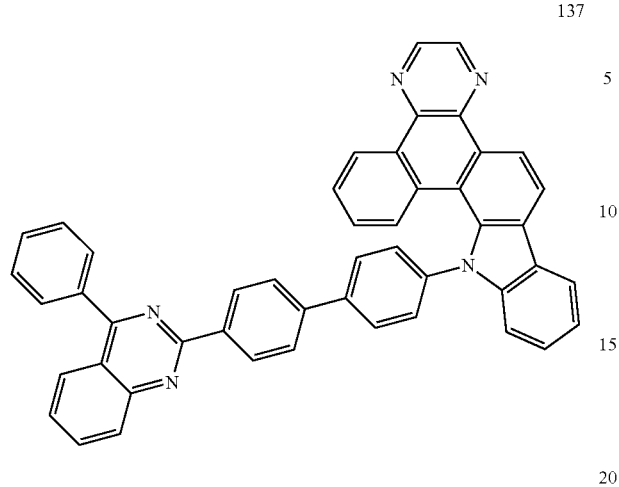
140
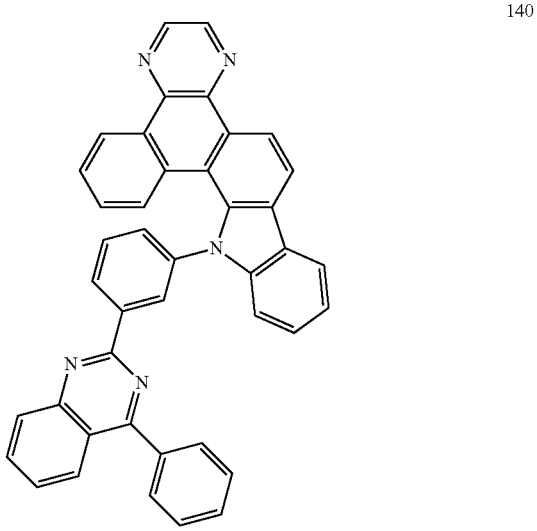
138
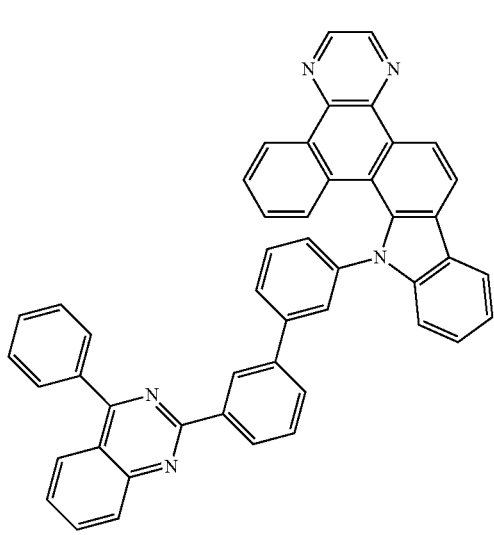
141
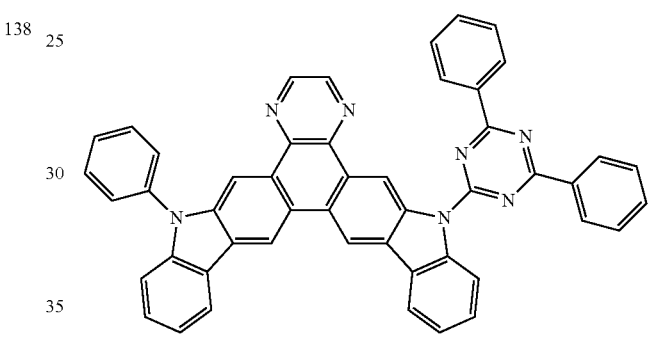
142
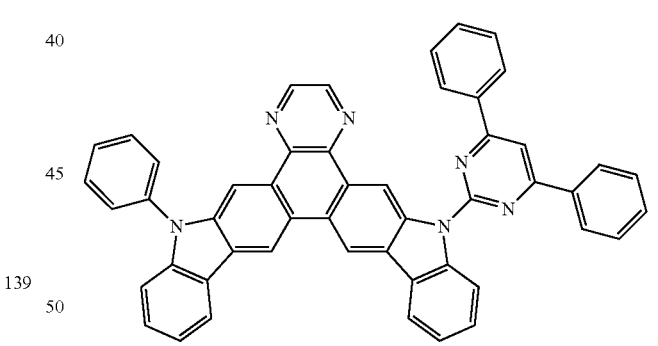
139
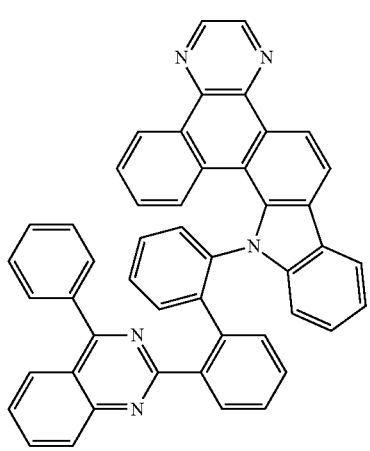
143
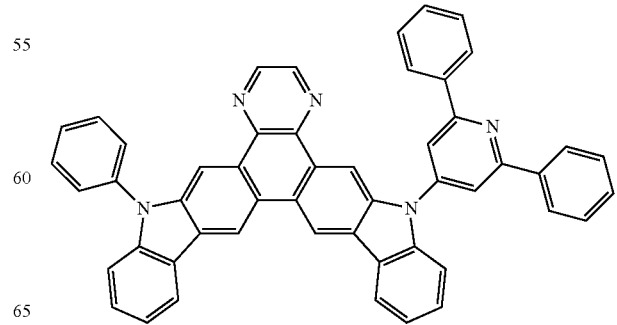

144

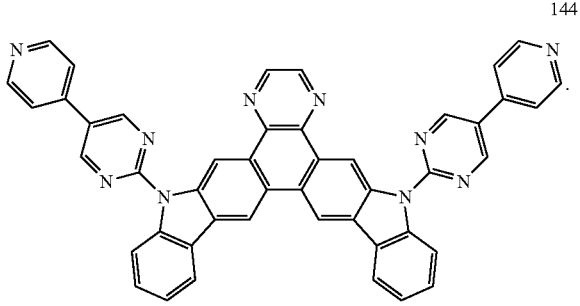

Hereinafter, an organic optoelectric device including the compound for an organic optoelectric device is described.

The organic optoelectric device may be any device to convert electrical energy into photoenergy and vice versa without particular limitation, and may be, for example an organic photoelectric device, an organic light emitting diode, an organic solar cell, and an organic photo-conductor drum.

The organic optoelectric device may include an anode and a cathode facing each other, and at least one organic layer between the anode and the cathode, wherein the organic layer includes the compound for an organic optoelectric device.

Herein, an organic light emitting diode as one example of an organic optoelectric device is described referring to drawings.

Figure 2:
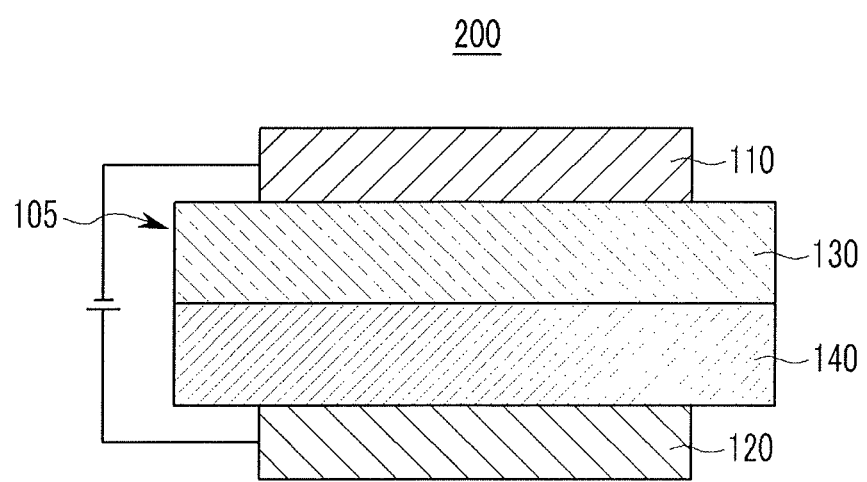

FIGS. 1 and 2 are cross-sectional views showing organic light emitting diodes according to embodiments.

Referring to FIG. 1, an organic light emitting diode 100 according to an embodiment includes an anode 120 and a cathode 110 facing each other and an organic layer 105 between the anode 120 and the cathode 110.

The anode 120 may be made of a conductor having a large work function to help hole injection, and may be for example metal, metal oxide and/or a conductive polymer. The anode 120 may be, for example a metal nickel, platinum, vanadium, chromium, copper, zinc, gold, and the like or an alloy thereof; metal oxide such as zinc oxide, indium oxide, indium tin oxide (ITO), indium zinc oxide (IZO), and the like; a combination of metal and oxide such as ZnO and Al or $SnO_2$ and Sb; a conductive polymer such as poly(3-methylthiophene), poly(3,4-(ethylene-1,2-dioxy)thiophene) (PEDT), polypyrrole, and polyaniline, but is not limited thereto.

The cathode 110 may be made of a conductor having a small work function to help electron injection, and may be for example metal, metal oxide and/or a conductive polymer. The cathode 110 may be for example a metal or an alloy thereof such as magnesium, calcium, sodium, potassium, titanium, indium, yttrium, lithium, gadolinium, aluminum silver, tin, lead, cesium, barium, and the like; a multi-layer structure material such as LiF/Al, $LiO_2$/Al, LiF/Ca, LiF/Al and $BaF_2$/Ca, but is not limited thereto.

The organic layer 105 includes a light-emitting layer 130 including the compound for an organic optoelectric device.

The light-emitting layer 130 may include, for example the compound for an organic optoelectric device alone, or at least two of the compound for an organic optoelectric device.

The compound for an organic optoelectric device according to an embodiment may be, for example included as a host of a light-emitting layer and may be, for example included as a green host.

Referring to FIG. 2, an organic light emitting diode 200 further includes a hole auxiliary layer 140 in addition to the light-emitting layer 130. The hole auxiliary layer 140 may further increase hole injection and/or hole mobility and block electrons between the anode 120 and the light-emitting layer 130. The hole auxiliary layer 140 may be, for example a hole transport layer, a hole injection layer, and/or an electron blocking layer, and may include at least one layer. The compound for an organic optoelectric device may be included in the light-emitting layer 130.

In an embodiment of the present invention, in FIG. 1 or 2, an organic light emitting diode may further an electron transport layer, an electron injection layer, a hole injection layer, and the like as an organic layer 105.

The organic light emitting diodes 100 and 200 may be manufactured by forming an anode or a cathode on a substrate, forming an organic layer using a dry film formation method such as a vacuum deposition method (evaporation), sputtering, plasma plating, and ion plating, and forming a cathode or an anode thereon.

The organic light emitting diode may be applied to an organic light emitting display device.

Hereinafter, the embodiments are illustrated in more detail with reference to examples. These examples, however, are not in any sense to be interpreted as limiting the scope of the invention (Synthesis of Compound for Organic Optoelectric Device)

Hereinafter, starting materials and reactants used in Examples and Synthesis Examples were purchased from Sigma-Aldrich Co. Ltd. or TCI Inc. as far as there in no particular comment.

Synthesis Example 1: Synthesis of Intermediate I-1

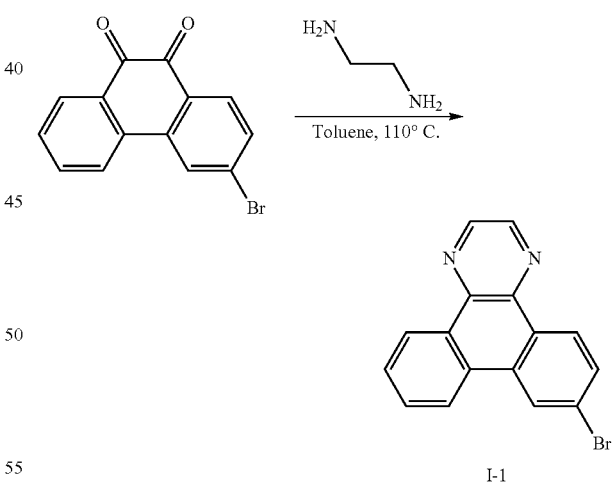

I-1

An intermediate, 3-bromophenanthrene-9,10-dione (50 g, 174 mmol) purchased from Chemirex Co., Ltd. (http://chemirex.com/) was dissolved in 0.5 L of toluene under a nitrogen environment, ethylene diamine (12.6 g, 209 mmol) was added thereto, and the mixture was heated and refluxed for 5 hours. After the reaction was complete, water was added to the reaction solution, the mixture was extracted with dichloromethane (DCM) and treated with anhydrous $MgSO_4$ to remove moisture, and the resultant was filtered and concentrated under a reduced pressure. The obtained residue was separated and purified through flash column chromatography to obtain Intermediate I-1 (40.3 g, 75%).

HRMS (70 eV, EI+): m/z calcd for C16H9BrN2: 307.9949, found: 308.

Elemental Analysis: C, 62%; H, 3%

Synthesis Example 2: Synthesis of Intermediate I-2

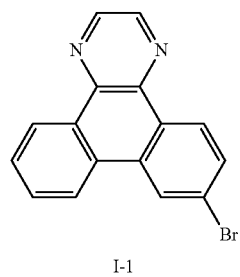

I-1

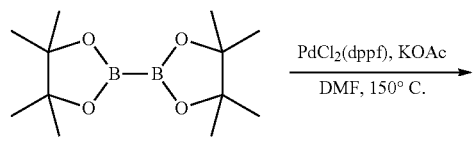

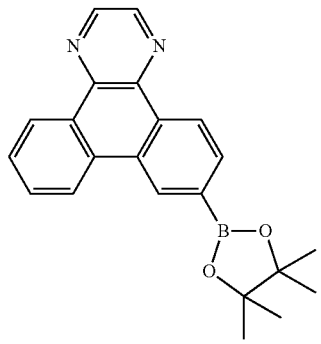

I-2

Intermediate I-1 (35 g, 113 mmol) was dissolved in dimethylforamide (DMF, 0.35 L) under a nitrogen environment, bis(pinacolato)diboron (34.5 g, 136 mmol), (1,1'-bis(diphenylphosphine)ferrocene)dichloropalladium (II) (0.92 g, 1.13 mmol), and potassium acetate (33.3 g, 339 mmol) were added thereto, and the mixture was heated and refluxed at 150° C. for 12 hours. When the reaction was complete, water was added to the reaction solution, and the mixture was filtered, and dried in a vacuum oven. The obtained residue was separated and purified through flash column chromatography to obtain Intermediate I-2 (27.8 g, 69%).

HRMS (70 eV, EI+): m/z calcd for C22H21BN2O2: 356.1696, found: 356.

Elemental Analysis: C, 74%; H, 6%

Synthesis Example 3: Synthesis of Intermediate I-3

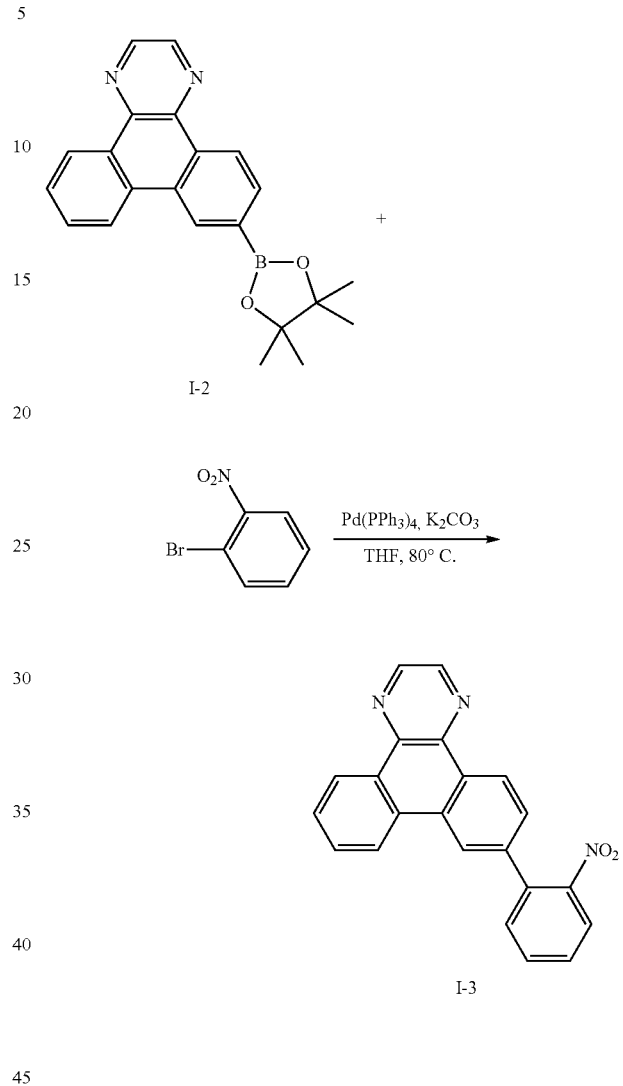

Intermediate I-2 (25 g, 70.2 mmol) was dissolved in tetrahydrofuran (THF, 0.2 L) under a nitrogen environment, 1-bromo-2-nitrobenzene (14.2 g, 70.2 mmol) purchased from Tokyo Chemical Industry Co., Ltd., tetrakis(triphenylphosphine)palladium (0.81 g, 0.70 mmol), and potassium carbonate saturated in water (24.3 g, 176 mmol) were added thereto, and the mixture is heated and refluxed at 80° C. for 13 hours. After the reaction was complete, water was added to the reaction solution, the mixture was extracted with dichloromethane (DCM) and treated with anhydrous MgSO4 to remove moisture, and the resultant was filtered and concentrated under a reduced pressure. The obtained residue was separated and purified through flash column chromatography to obtain Intermediate I-3 (20.0 g, 81%).

HRMS (70 eV, EI+): m/z calcd for C22H13N3O2: 351.1008, found: 351.

Elemental Analysis: C, 75%; H, 4%

Synthesis Example 4: Synthesis of Intermediate I-4

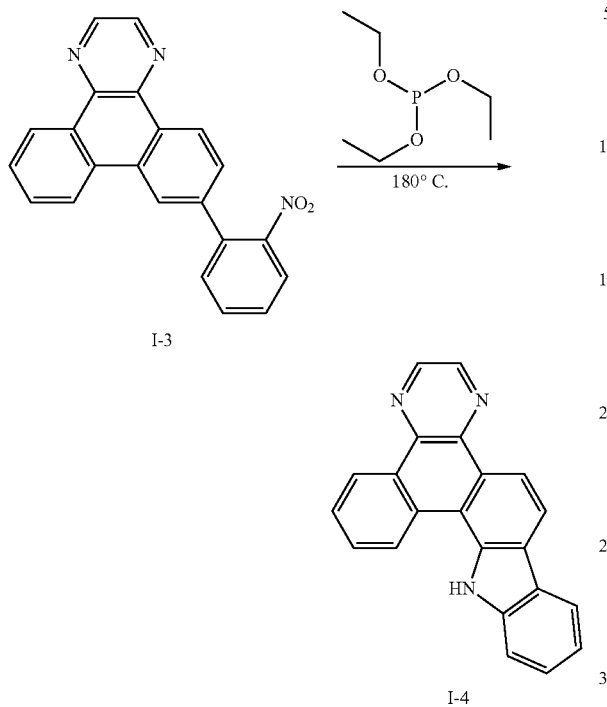

Intermediate I-3 (15 g, 42.7 mmol) was dissolved in triethylphosphite (0.1 L) purchased from Sigma Aldrich Co., Ltd. under a nitrogen environment and then, heated and refluxed at 180° C. for 3 hours. After the reaction was complete, water was added to the reaction solution, the mixture was extracted with dichloromethane (DCM) and treated with anhydrous MgSO$_4$ to remove moisture, and the resultant was filtered and concentrated under a reduced pressure. The obtained residue was separated and purified through flash column chromatography to obtain Intermediate I-4 (8.45 g, 62%).

HRMS (70 eV, EI+): m/z calcd for C22H13N3: 319.1109, found: 319.

Elemental Analysis: C, 83%; H, 4%

Synthesis Example 5: Synthesis of Intermediate I-5

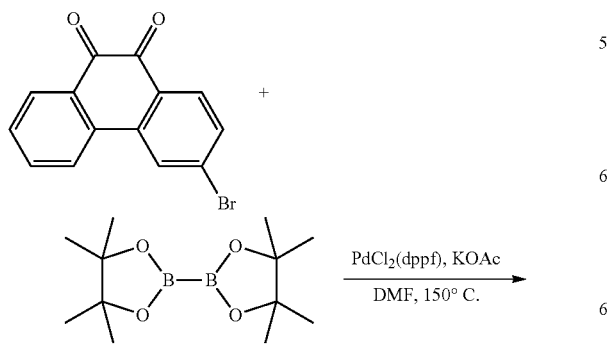

An intermediate, 3-bromophenanthrene-9,10-dione (100 g, 299 mmol) purchased from Chemirex Co., Ltd. was dissolved in dimethylforamide (DMF, 1.0 L) under a nitrogen environment, bis(pinacolato)diboron (91.2 g, 359 mmol), (1,1'-bis(diphenylphosphine)ferrocene)dichloropalladium (II) (2.44 g, 2.99 mmol), and potassium acetate (88.0 g, 897 mmol) were added thereto, and the mixture was heated and refluxed at 150° C. for 11 hours. When the reaction was complete, water was added to the reaction solution, and the mixture was filtered, and dried in a vacuum oven. The obtained residue was separated and purified through flash column chromatography to obtain Intermediate I-5 (82.9 g, 83%).

HRMS (70 eV, EI+): m/z calcd for C20H19BO4: 334.1376, found: 334.

Elemental Analysis: C, 72%; H, 6%

Synthesis Example 6: Synthesis of Intermediate I-6

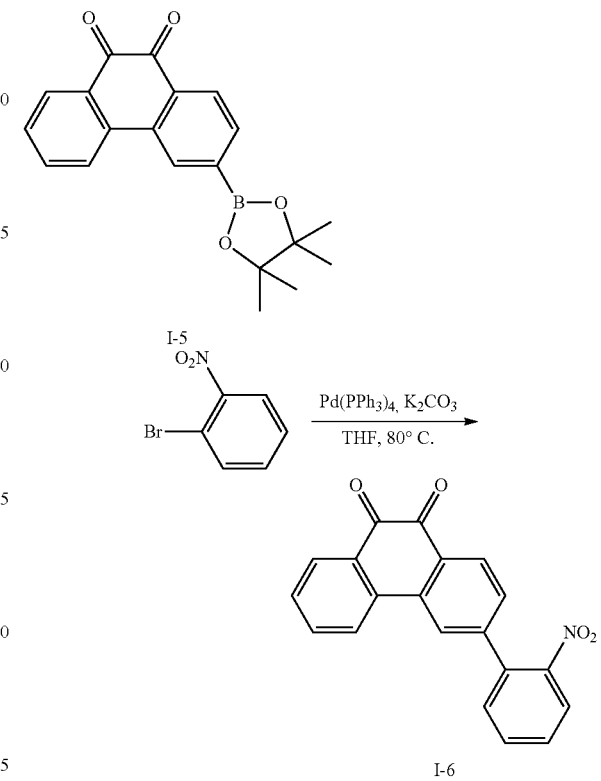

Intermediate I-5 (80 g, 239 mmol) was dissolved in tetrahydrofuran (THF, 0.4 L) under a nitrogen environment, 1-bromo-2-nitrobenzene (48.4 g, 239 mmol) purchased from Tokyo Chemical Industry Co., Ltd., tetrakis(triphenylphosphine)palladium (2.76 g, 2.39 mmol), and potassium carbonate saturated in water (82.6 g, 598 mmol) were added thereto, and the mixture was heated and refluxed at 80° C. for 19 hours. After the reaction was complete, water was added to the reaction solution, the mixture was extracted with dichloromethane (DCM) and treated with anhydrous MgSO₄ to remove moisture, and the resultant was filtered and concentrated under a reduced pressure. The obtained residue was separated and purified through flash column chromatography to obtain Intermediate I-6 (23.6 g, 30%).

HRMS (70 eV, EI+): m/z calcd for C20H11NO4: 329.0688, found: 329.

Elemental Analysis: C, 73%; H, 3%

Synthesis Example 7: Synthesis of Intermediate I-7

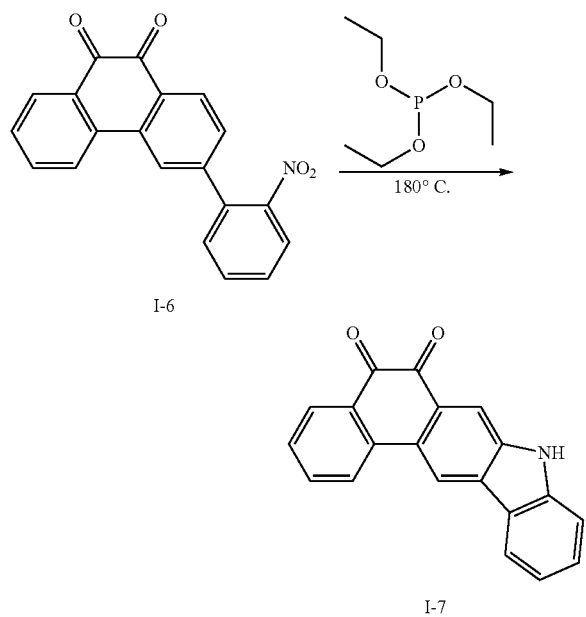

Intermediate I-6 (21 g, 63.8 mmol) was dissolved in triethylphosphite (0.1 L) purchased from Sigma Aldrich Co., Ltd. under a nitrogen environment and then, heated and refluxed at 180° C. for 3 hours. After the reaction was complete, water was added to the reaction solution, the mixture was extracted with dichloromethane (DCM) and treated with anhydrous MgSO₄ to remove moisture, and the resultant was filtered and concentrated under a reduced pressure. The obtained residue was separated and purified through flash column chromatography to obtain Intermediate I-7 (9.10 g, 48%).

HRMS (70 eV, EI+): m/z calcd for C20H11NO2: 297.0790, found: 297.

Elemental Analysis: C, 81%; H, 4%

Synthesis Example 8: Synthesis of Intermediate I-8

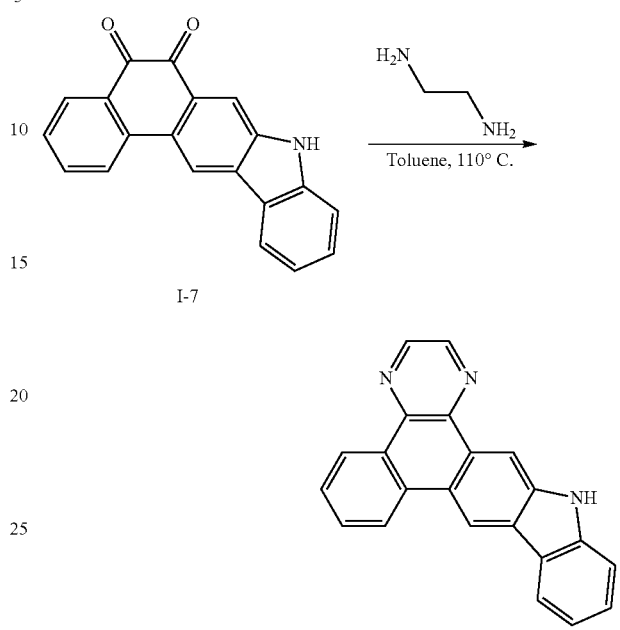

Intermediate I-7 (8 g, 26.9 mmol) was dissolved in toluene (0.08 L) under a nitrogen environment, ethylene diamine (2.43 g, 40.4 mmol) was added thereto, and the mixture was heated and refluxed for 5 hours. After the reaction was complete, water was added to the reaction solution, the mixture was extracted with dichloromethane (DCM) and treated with anhydrous MgSO₄ to remove moisture, and the resultant was filtered and concentrated under a reduced pressure. The obtained residue was separated an purified through flash column chromatography to obtain Intermediate I-8 (6.01 g, 70%).

HRMS (70 eV, EI+): m/z calcd for C22H13N3: 319.1109, found: 319.

Elemental Analysis: C, 83%; H, 4%

Synthesis Example 9: Synthesis of Intermediate I-9

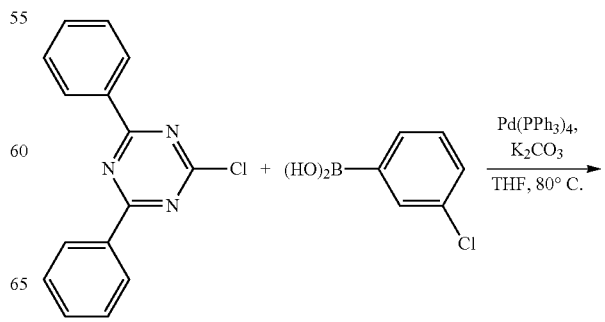

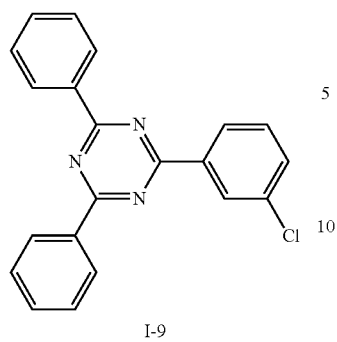

I-9

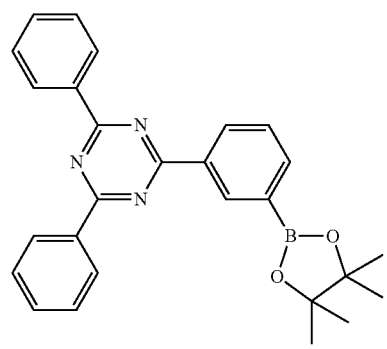

I-10

2-chloro-4,6-diphenyl-1,3,5-triazine (100 g, 374 mmol) purchased from Tokyo Chemical Industry Co., Ltd. was dissolved in tetrahydrofuran (THF, 0.8 L) under a nitrogen environment, 3-chlorophenylboronic acid (64.3 g, 411 mmol) purchased from Tokyo Chemical Industry Co., Ltd., tetrakis(triphenylphosphine)palladium (4.32 g, 3.74 mmol), and potassium carbonate saturated in water (129 g, 935 mmol) were added thereto, and the mixture was heated and refluxed at 80° C. for 8 hours. After the reaction was complete, water was added to the reaction solution, the mixture was extracted with dichloromethane (DCM) and treated with anhydrous MgSO₄ to remove moisture, and the resultant was filtered and concentrated under a reduced pressure. The obtained residue was separated and purified through flash column chromatography to obtain Intermediate I-9 (116 g, 90%).

HRMS (70 eV, EI+): m/z calcd for C21H14ClN3: 343.0876, found: 343.

Elemental Analysis: C, 73%; H, 4%

Intermediate I-9 (110 g, 320 mmol) was dissolved in dimethylforamide (DMF, 1.0 L) under a nitrogen environment, bis(pinacolato)diboron (97.5 g, 384 mmol), (1,1'-bis (diphenylphosphine)ferrocene)dichloropalladium (II) (2.61 g, 3.20 mmol), and potassium acetate (94.2 g, 960 mmol) were added thereto, and the mixture was heated and refluxed at 150° C. for 24 hours. When the reaction was complete, water was added to the reaction solution, and the mixture was filtered, and dried in a vacuum oven. The obtained residue was separated and purified through flash column chromatography to obtain Intermediate I-10 (97.5 g, 70%).

HRMS (70 eV, EI+): m/z calcd for C27H26BN3O2: 435.2118, found: 435.

Elemental Analysis: C, 74%; H, 6%

Synthesis Example 10: Synthesis of Intermediate I-10

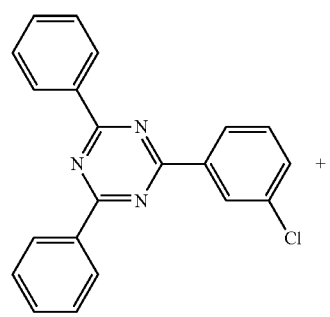

I-9

Synthesis Example 11: Synthesis of Intermediate I-11

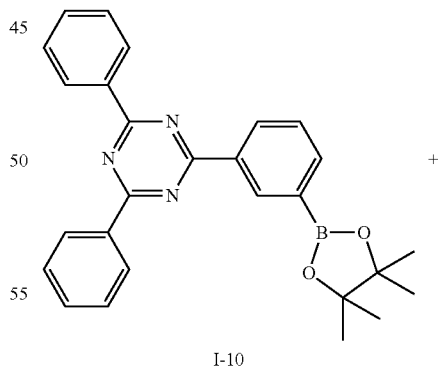

I-10

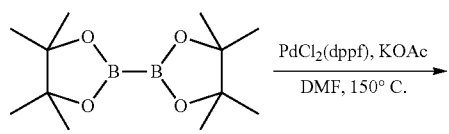

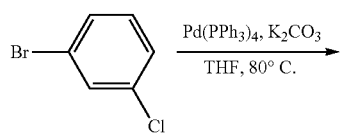

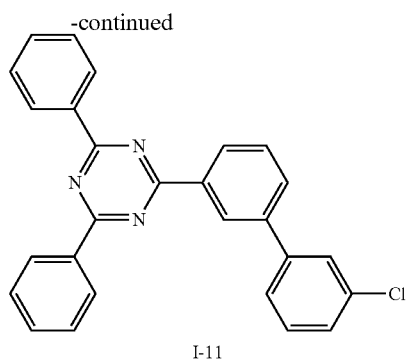

I-11

Intermediate I-10 (95 g, 218 mmol) was dissolved in tetrahydrofuran (THF, 0.7 L) under a nitrogen environment, 1-bromo-3-chlorobenzene (41.8 g, 218 mmol) purchased from Tokyo Chemical Industry Co., Ltd., tetrakis(triphenylphosphine)palladium (2.52 g, 2.18 mmol), and potassium carbonate saturated in water (75.3 g, 545 mmol) were added thereto, and the mixture was heated and refluxed at 80° C. for 10 hours. After the reaction was complete, water was added to the reaction solution, the mixture was extracted with dichloromethane (DCM) and treated with anhydrous MgSO$_4$ to remove moisture, and the resultant was filtered and concentrated under a reduced pressure. The obtained residue was separated and purified through flash column chromatography to obtain Intermediate I-11 (77.8 g, 85%).

HRMS (70 eV, EI+): m/z calcd for C27H18ClN3: 419.1189, found: 419.

Elemental Analysis: C, 77%; H, 4%

Synthesis Example 12: Synthesis of Intermediate I-12

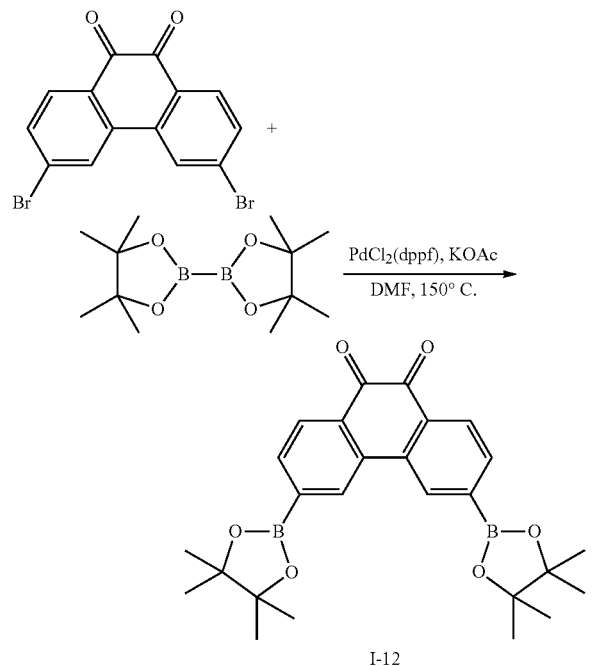

I-12

3,6-dibromophenanthrene-9,10-dione (100 g, 273 mmol) purchased from Chemirex Co., Ltd. was dissolved in dimethylforamide (DMF, 1.4 L) under a nitrogen environment, bis(pinacolato)diboron (173 g, 683 mmol), (1,1'-bis(diphenylphosphine)ferrocene)dichloropalladium (II) (4.46 g, 5.46 mmol), and potassium acetate (134 g, 1,365 mmol) were added thereto, and the mixture was heated and refluxed at 150° C. for 10 hours. When the reaction was complete, water was added to the reaction solution, and the mixture was filtered, and dried in a vacuum oven. The obtained residue was separated and purified through flash column chromatography to obtain Intermediate I-12 (113 g, 90%).

HRMS (70 eV, EI+): m/z calcd for C26H30B2O6: 460.2228, found: 460.

Elemental Analysis: C, 68%; H, 7%

Synthesis Example 13: Synthesis of Intermediate I-13

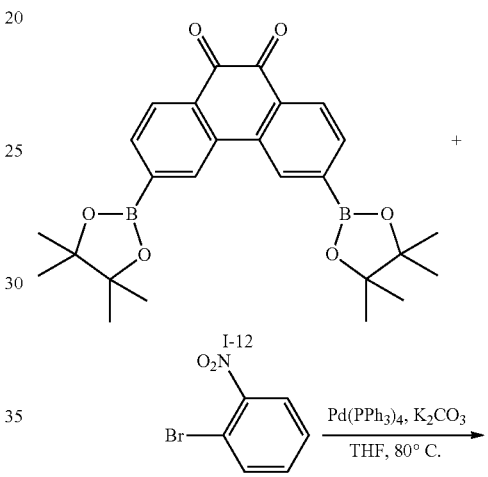

I-13

Intermediate I-12 (110 g, 239 mmol) was dissolved in tetrahydrofuran (THF, 1.1 L) under a nitrogen environment, 1-bromo-2-nitrobenzene (105 g, 526 mmol) purchased from Tokyo Chemical Industry Co., Ltd., tetrakis(triphenylphosphine)palladium (5.52 g, 4.78 mmol), and potassium carbonate saturated in water (165 g, 1,195 mmol) were added thereto, and the mixture was heated and refluxed at 80° C. for 25 hours. After the reaction was complete, water was added to the reaction solution, the mixture was extracted with dichloromethane (DCM) and treated with anhydrous MgSO$_4$ to remove moisture, and the resultant was filtered and concentrated under a reduced pressure. The obtained residue was separated and purified through flash column chromatography to obtain Intermediate I-13 (38.8 g, 36%).

HRMS (70 eV, EI+): m/z calcd for C26H14N2O6: 450.0852, found: 450.

Elemental Analysis: C, 69%; H, 3%

Synthesis Example 14: Synthesis of Intermediate I-14

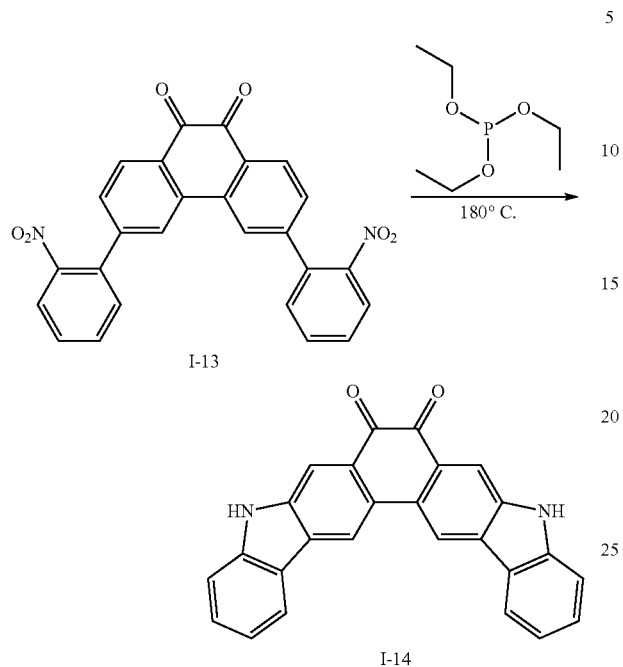

Intermediate I-13 (35 g, 15.8 mmol) was dissolved in triethylphosphite (0.2 L) purchased from Sigma Aldrich Co., Ltd. under a nitrogen environment and then, heated and refluxed at 180° C. for 3 hours. After the reaction was complete, water was added to the reaction solution, the mixture was extracted with dichloromethane (DCM) and treated with anhydrous MgSO₄ to remove moisture, and the resultant was filtered and concentrated under a reduced pressure. The obtained residue was separated and purified through flash column chromatography to obtain Intermediate I-14 (9.10 g, 48%).

HRMS (70 eV, EI+): m/z calcd for $C_{26}H_{14}N_2O_2$: 386.1055, found: 386.

Elemental Analysis: C, 81%; H, 4%

Synthesis Example 15: Synthesis of Intermediate I-15

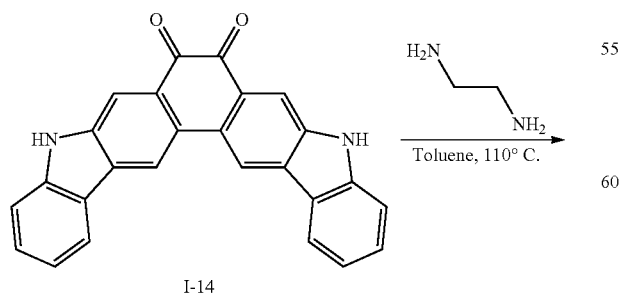

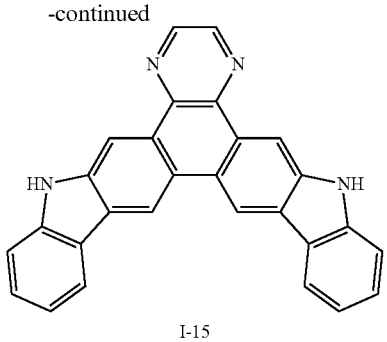

Intermediate I-14 (8 g, 20.7 mmol) was dissolved in toluene (0.08 L) under a nitrogen environment, ethylene diamine (1.87 g, 31.1 mmol) was added thereto, and the mixture was heated and refluxed for 5 hours. After the reaction was complete, water was added to the reaction solution, the mixture was extracted with dichloromethane (DCM) and treated with anhydrous MgSO₄ to remove moisture, and the resultant was filtered and concentrated under a reduced pressure. The obtained residue was separated and purified through flash column chromatography to obtain Intermediate I-15 (6.34 g, 75%).

HRMS (70 eV, EI+): m/z calcd for $C_{28}H_{16}N_4$: 408.1375, found: 408.

Elemental Analysis: C, 82%; H, 4%

Synthesis Example 16: Synthesis of Intermediate I-16

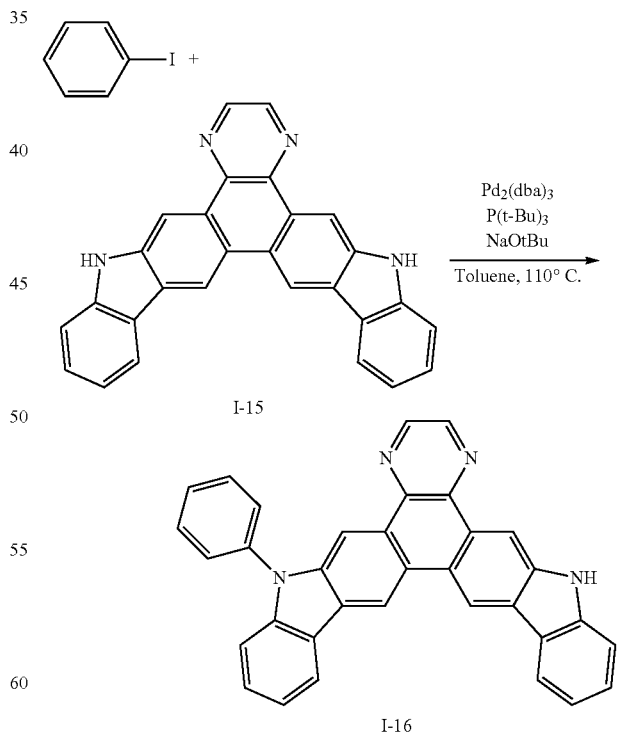

Iodobenzene (9.08 g, 44.5 mmol) purchased from Tokyo Chemical Industry Co., Ltd. was dissolved in toluene (0.15 L) under a nitrogen environment, Intermediate I-15 (20 g, 49.0 mmol), tris(diphenylideneacetone)dipalladium (0)

(0.41 g, 0.45 mmol), tris-tert butylphosphine (0.45 g, 2.23 mmol), and sodium tert-butoxide (5.13 g, 53.4 mmol) were sequentially added thereto, and the mixture was heated and refluxed at 110° C. for 12 hours. After the reaction was complete, water was added to the reaction solution, the mixture was extracted with dichloromethane (DCM) and treated with anhydrous MgSO₄ to remove moisture, and the resultant was filtered and concentrated under a reduced pressure. The obtained residue was separated and purified through flash column chromatography to obtain Intermediate I-16 (19.4 g, 90%).

HRMS (70 eV, EI+): m/z calcd for C34H20N4: 484.1688, found: 484.

Elemental Analysis: C, 84%; H, 4%

Synthesis Example 17: Synthesis of Compound 1

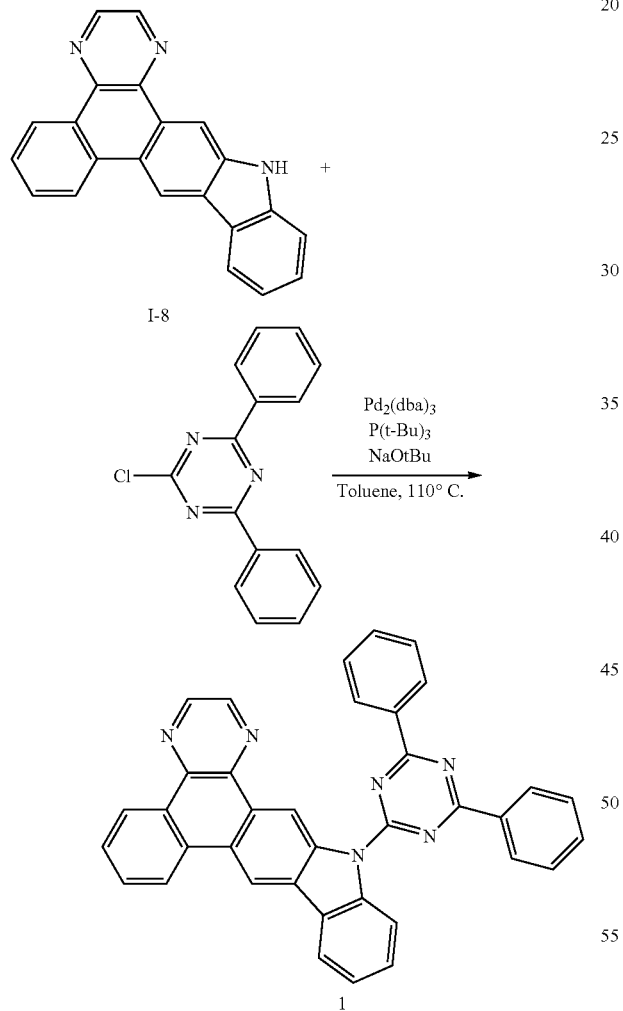

Intermediate I-8 (10 g, 31.3 mmol) was dissolved in toluene (0.1 L) under a nitrogen environment, 2-chloro-4,6-diphenyl-1,3,5-triazine (8.38 g, 31.3 mmol) purchased from Tokyo Chemical Industry Co., Ltd., tris(diphenylideneacetone)dipalladium(0) (0.28 g, 0.31 mmol), tris-tert butylphosphine (0.32 g, 1.57 mmol), and sodium tert-butoxide (3.61 g, 37.6 mmol) were sequentially added thereto, and the mixture was heated and refluxed at 110° C. for 13 hours. After the reaction was complete, water was added to the reaction solution, the mixture was extracted with dichloromethane (DCM) and treated with anhydrous MgSO₄ to remove moisture, and the resultant was filtered and concentrated under a reduced pressure. The obtained residue was separated and purified through flash column chromatography to obtain Compound 1 (15.2 g, 88%).

HRMS (70 eV, EI+): m/z calcd for C37H22N6: 550.1906, found: 550.

Elemental Analysis: C, 81%; H, 4%

Synthesis Example 18: Synthesis of Compound 5

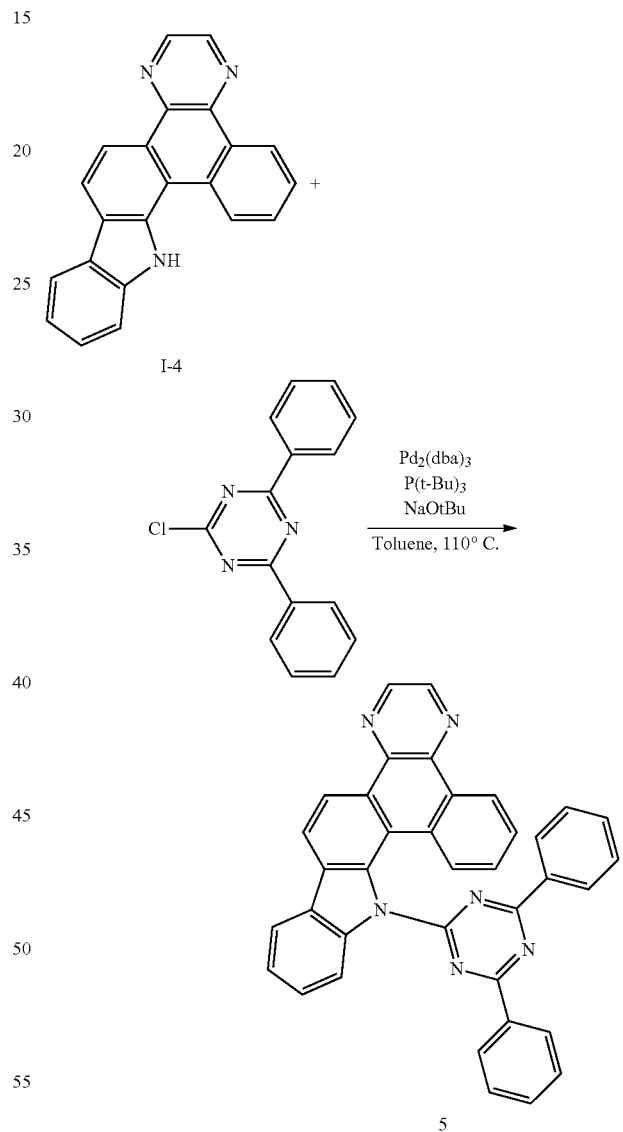

Intermediate I-4 (10 g, 31.3 mmol) was dissolved in toluene (0.1 L) under a nitrogen environment, 2-chloro-4,6-diphenyl-1,3,5-triazine (8.38 g, 31.3 mmol) purchased from Tokyo Chemical Industry Co., Ltd., tris(diphenylideneacetone)dipalladium(0) (0.28 g, 0.31 mmol), tris-tert butylphosphine (0.32 g, 1.57 mmol), and sodium tert-butoxide (3.61 g, 37.6 mmol) were sequentially added thereto, and the mixture was heated and refluxed at 110° C. for 25 hours. After the reaction was complete, water was added to the reaction solution, the mixture was extracted with dichloromethane (DCM) and treated with anhydrous MgSO₄ to remove moisture, and the resultant was filtered and concentrated under a reduced pressure. The obtained residue was separated and purified through flash column chromatography to obtain Compound 5 (5.51 g, 32%).

HRMS (70 eV, EI+): m/z calcd for C37H22N6: 550.1906, found: 550.

Elemental Analysis: C, 81%; H, 4%

Synthesis Example 19: Synthesis of Compound 18

HRMS (70 eV, EI+): m/z calcd for C49H30N6: 702.2532, found: 702.

Elemental Analysis: C, 84%; H, 4%

Synthesis Example 20: Synthesis of Compound 22

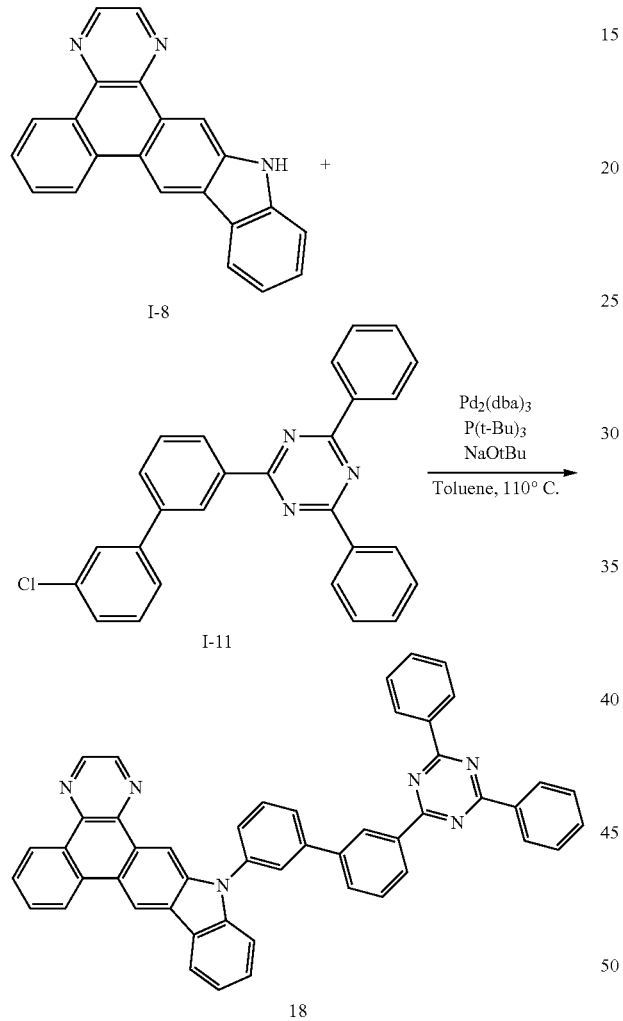

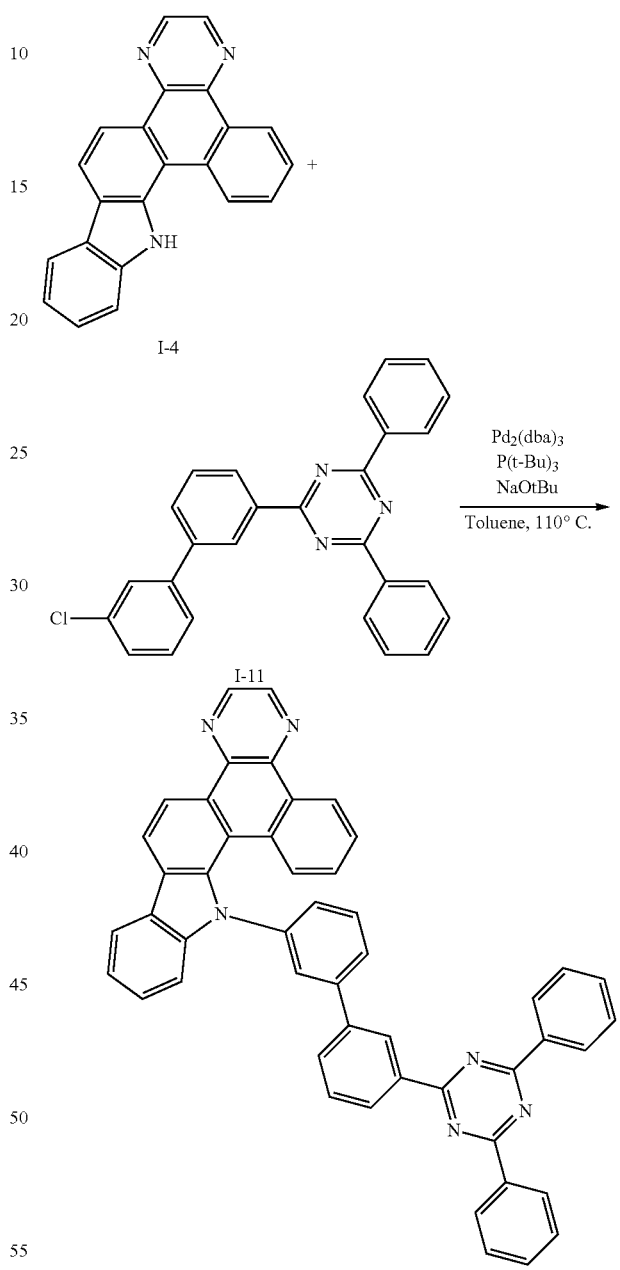

Intermediate I-8 (10 g, 31.3 mmol) was dissolved in toluene (0.1 L) under a nitrogen environment, intermediate I-11 (13.1 g, 31.3 mmol), tris(diphenylideneacetone)dipalladium(0) (0.28 g, 0.31 mmol), tris-tert butylphosphine (0.32 g, 1.57 mmol), and sodium tert-butoxide (3.61 g, 37.6 mmol) were sequentially added thereto, and the mixture was heated and refluxed at 110° C. for 10 hours. After the reaction was complete, water was added to the reaction solution, the mixture was extracted with dichloromethane (DCM) and treated with anhydrous MgSO₄ to remove moisture, and the resultant was filtered and concentrated under a reduced pressure. The obtained residue was separated and purified through flash column chromatography to obtain Compound 18 (20.5 g, 93%).

Intermediate I-4 (10 g, 31.3 mmol) was dissolved in toluene (0.1 L) under a nitrogen environment, intermediate I-11 (13.1 g, 31.3 mmol), tris(diphenylideneacetone)dipalladium(0) (0.28 g, 0.31 mmol), tris-tert butylphosphine (0.32 g, 1.57 mmol), and sodium tert-butoxide (3.61 g, 37.6 mmol) were sequentially added thereto, and the mixture was heated and refluxed at 110° C. for 30 hours. After the reaction was complete, water was added to the reaction solution, the mixture was extracted with dichloromethane (DCM) and treated with anhydrous MgSO₄ to remove moisture, and the resultant was filtered and concentrated under a reduced pressure. The obtained residue was separated and purified through flash column chromatography to obtain Compound 22 (4.40 g, 20%).

HRMS (70 eV, EI+): m/z calcd for C49H30N6: 702.2532, found: 702.

Elemental Analysis: C, 84%; H, 4%

Synthesis Example 21: Synthesis of Compound 97

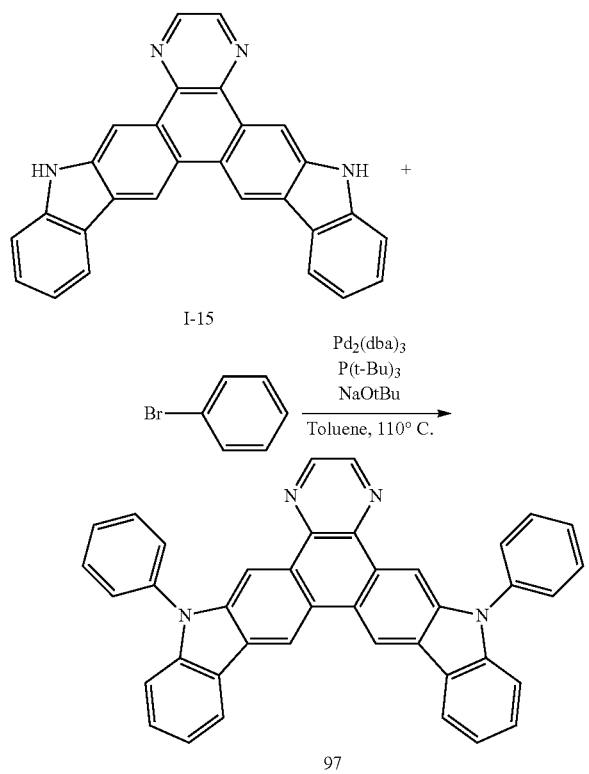

Intermediate I-15 (10 g, 24.5 mmol) was dissolved in toluene (0.1 L) under a nitrogen environment, bromobenzene (8.46 g, 53.9 mmol) purchased from Tokyo Chemical Industry Co., Ltd., tris(diphenylideneacetone)dipalladium (0) (0.45 g, 0.49 mmol), tris-tert butylphosphine (0.50 g, 2.45 mmol), and sodium tert-butoxide (4.71 g, 49.0 mmol) were sequentially added thereto, and the mixture was heated and refluxed at 110° C. for 18 hours. After the reaction was complete, water was added to the reaction solution, the mixture was extracted with dichloromethane (DCM) and treated with anhydrous MgSO₄ to remove moisture, and the resultant was filtered and concentrated under a reduced pressure. The obtained residue was separated and purified through flash column chromatography to obtain Compound 97 (11.7 g, 85%).

HRMS (70 eV, EI+): m/z calcd for C40H24N4: 560.2001, found: 560.

Elemental Analysis: C, 86%; H, 4%

Synthesis Example 22: Synthesis of Compound 141

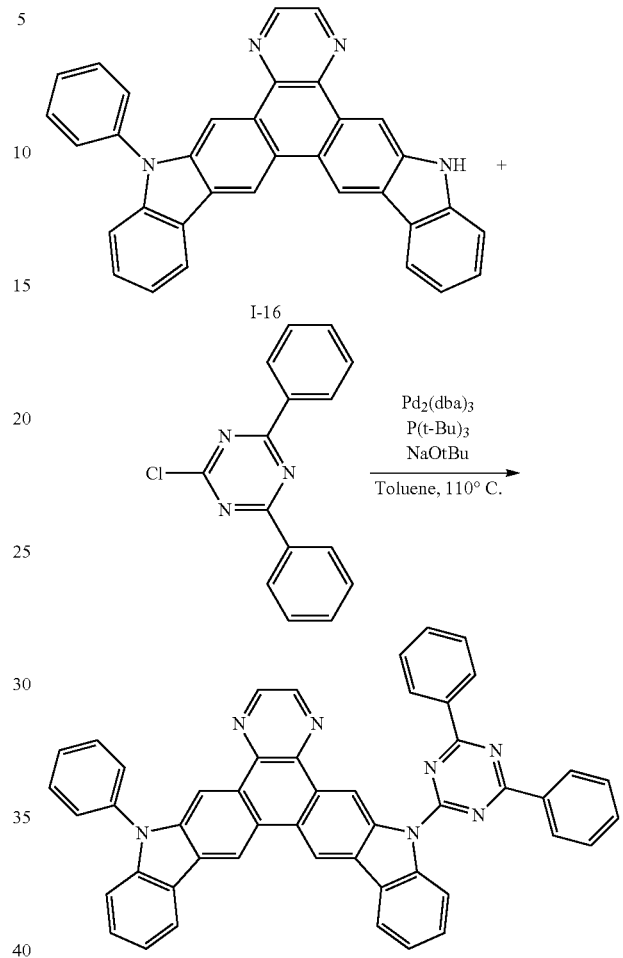

Intermediate I-16 (10 g, 20.6 mmol) was dissolved in toluene (0.1 L) under a nitrogen environment, 2-chloro-4,6-diphenyl-1,3,5-triazine (5.52 g, 20.6 mmol) purchased from Tokyo Chemical Industry Co., Ltd., tris(diphenylideneacetone)dipalladium(0) (0.20 g, 0.21 mmol), tris-tert butylphosphine (0.21 g, 1.03 mmol), and sodium tert-butoxide (2.38 g, 24.7 mmol) were sequentially added thereto, and the mixture was heated and refluxed at 110° C. for 15 hours. After the reaction was complete, water was added to the reaction solution, the mixture was extracted with dichloromethane (DCM) and treated with anhydrous MgSO₄ to remove moisture, and the resultant was filtered and concentrated under a reduced pressure. The obtained residue was separated and purified through flash column chromatography to obtain Compound 141 (13.4 g, 91%).

HRMS (70 eV, EI+): m/z calcd for C49H29N7: 715.2484, found: 715.

Elemental Analysis: C, 82%; H, 4%

Synthesis Example 23: Synthesis of Compound Host 1

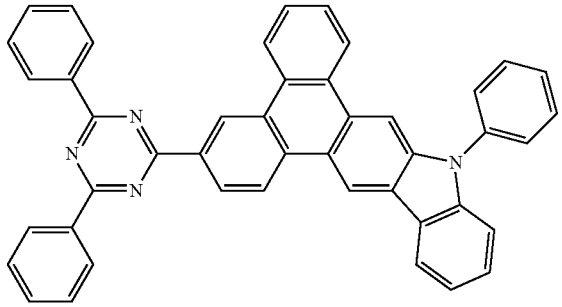

Host 1

Host 1 was synthesized with a reference to Patent KR1196093.

HRMS (70 eV, EI+): m/z calcd for C45H28N4: 624.2314, found: 624.

Elemental Analysis: C, 87%; H, 5%

Synthesis Example 24: Synthesis of Compound Host 2

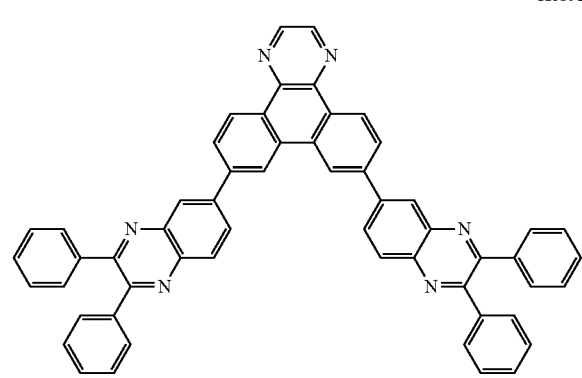

Host 2

Host 2 was synthesized with a reference to KR1486096.

HRMS (70 eV, EI+): m/z calcd for C56H34N6: 790.2845, found: 790.

Elemental Analysis: C, 85%; H, 4%

Synthesis Example 25: Synthesis of Compound Host 3

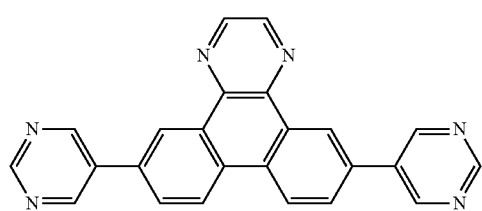

Host 3

Host 3 was synthesized with a reference to KR2011-0042004.

HRMS (70 eV, EI+): m/z calcd for C24H14N6: 386.1280, found: 386.

Elemental Analysis: C, 75%; H, 4%

Manufacture of Organic Light Emitting Diode

Example 1

An organic light emitting diode was manufactured by using Compound 1 according to Synthesis Example 17 as a host and Ir(PPy)₃ as a dopant.

A 1000 Å-thick ITO was used as an anode, and a 1000 Å-thick aluminum (Al) as a cathode. Specifically, the organic light emitting diode was manufactured in a method of cutting an ITO glass substrate having sheet resistance of 15 Ω/cm² into a size of 50 mm×50 mm×0.7 mm, ultrasonic wave-cleaning it in acetone, isopropyl alcohol, and pure water respectively for 15 minutes, and UV ozone-cleaning it for 30 minutes.

On the substrate, an 800 Å-thick hole transport layer was formed by depositing N4,N4'-di(naphthalen-1-yl)-N4,N4'-diphenylbiphenyl-4,4'-diamine (NPB) (80 nm) under a vacuum degree of 650×10⁻⁷ Pa at a deposition rate of 0.1 to 0.3 nm/s. Subsequently, a 300 Å-thick light-emitting layer was formed by using Compound 1 according to Synthesis Example 16 under the same vacuum deposition condition as above, and herein, Ir(PPy)₃ as a phosphorescent dopant was simultaneously deposited. Herein, the phosphorescent dopant was deposited in an amount of 7 wt % based on 100 wt % of the total amount of the light-emitting layer by adjusting a deposition rate.

On the light-emitting layer, a 50 Å-thick hole blocking layer was formed by depositing bis(2-methyl-8-quinolinolate)-4-(phenylphenolato)aluminum (BAlq) under the same vacuum deposition condition as above. Subsequently, a 200 Å-thick electron transport layer was formed by depositing Alq3 under the same vacuum deposition condition as above. On the electron transport layer, LiF and Al were sequentially deposited as a cathode, manufacturing the organic photoelectric device.

The organic photoelectric device had a structure of ITO/NPB (80 nm)/EML (Compound 1 (93 wt %)+Ir(PPy)3 (7 wt %), 30 nm)/Balq (5 nm)/Alq3 (20 nm)/LiF (1 nm)/Al (100 nm).

Examples 2 to 6

Organic light emitting diodes were manufactured according to the same method as Example 1 by respectively using Compound 5, Compound 18, Compound 22, Compound 97 and Compound 141 of Synthesis Example 18 to Synthesis Example 22 instead of Compound 1 of Synthesis Example 17.

Comparative Example 1

An organic light emitting diode was manufactured according to the same method as Example 1 except for using CBP instead of Compound 1 of Synthesis Example 17.

Comparative Examples 2 to 4

Organic light emitting diodes were manufactured according to the same method as Example 1 by respectively using Host 1, Host 2, and Host 3 of Synthesis Examples 23 to 25 instead of Compound 1 of Synthesis Example 17.

NPB, BAlq, CBP, and Ir(PPy)3 used in the organic light emitting diodes respectively have the following structures.

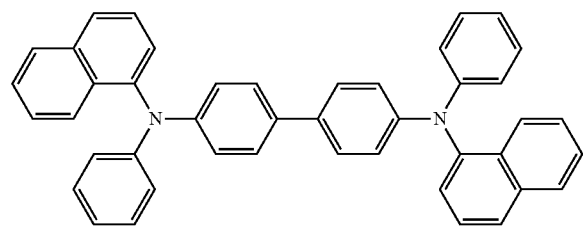

[NPB]

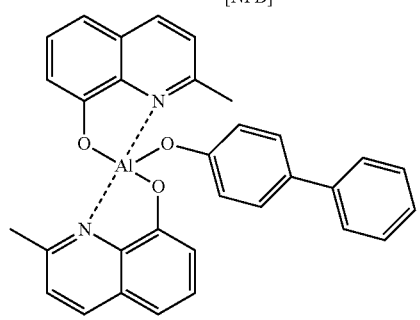

[BAlq]

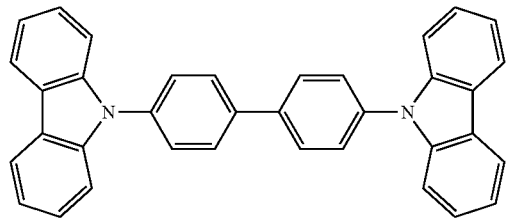

[CBP]

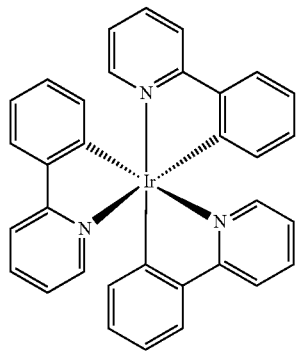

[Ir(PPy)3]

Evaluation

A current density change, a luminance change, and luminous efficiency of each organic light emitting diode according to Examples 1 to 6 and Comparative Examples 1 to 4 were measured.

Specific measurement methods are as follows, and the results are shown in Table 1.

(1) Measurement of Current Density Change Depending on Voltage Change

The obtained organic light emitting diodes were measured regarding a current value flowing in the unit device, while increasing the voltage from 0 V to 10 V using a current-voltage meter (Keithley 2400), and the measured current value was divided by area to provide the results.

(2) Measurement of Luminance Change Depending on Voltage Change

Luminance was measured by using a luminance meter (Minolta Cs-1000A), while the voltage of the organic light emitting diodes was increased from 0 V to 10 V.

(3) Measurement of Luminous Efficiency

Current efficiency (cd/A) at the same current density (10 mA/cm$^2$) were calculated by using the luminance, current density, and voltages (V) from the items (1) and (2).

TABLE 1

| Nos. | Compounds | Driving voltage (V) | Color (EL color) | Efficiency (cd/A) |
|---|---|---|---|---|
| Example 1 | 1 | 3.68 | Green | 52.6 |
| Example 2 | 5 | 3.65 | Green | 50.0 |
| Example 3 | 18 | 3.81 | Green | 56.2 |
| Example 4 | 22 | 3.77 | Green | 55.0 |
| Example 5 | 97 | 4.15 | Green | 58.1 |
| Example 6 | 141 | 3.60 | Green | 53.8 |
| Comparative Example 1 | CBP | 4.80 | Green | 31.4 |
| Comparative Example 2 | Host 1 | 4.55 | Green | 48.3 |
| Comparative Example 3 | Host 2 | 4.21 | Green | 38.9 |
| Comparative Example 4 | Host 3 | 4.60 | Green | 40.5 |

Referring to Table 1, the device results of Example 1 to Example 6 exhibit superbly low driving voltage and high efficiency compared with device results of Comparative Examples 1 to 4.

DESCRIPTION OF SYMBOLS

100, 200: organic light emitting diode
105: organic layer
110: cathode
120: anode
130: light-emitting layer
140: hole auxiliary layer

What is claimed is:
1. A compound for an organic optoelectric device represented by Chemical Formula I:

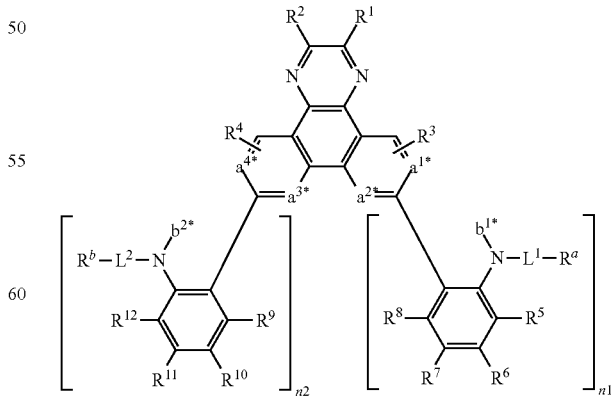

[Chemical Formula I]

wherein, in Chemical Formula I,
$a^1*$ to $a^4*$ are independently C or CR$^c$, a¹* or a²* is linked with b¹*,
a³* or a⁴* is linked with b²*,
$R^1$ to $R^{12}$ and $R^c$ are independently hydrogen, deuterium, a substituted or unsubstituted C1 to C10 alkyl group, a substituted or unsubstituted C6 to C20 aryl group, a substituted or unsubstituted C2 to C30 heteroaryl group, or a combination thereof,
$R^5$ to $R^{12}$ are independently present or $R^5$ and $R^6$, $R^6$ and $R^7$, $R^7$ and $R^8$, $R^9$ and $R^{10}$, $R^{10}$ and $R^{11}$, and $R^{11}$ and $R^{12}$ are optionally fused to form a ring,
$L^1$ and $L^2$ are independently a single bond, a substituted or unsubstituted C6 to C30 arylene group, or a substituted or unsubstituted C2 to C30 heteroarylene group,
$R^a$ and $R^b$ are independently a substituted or unsubstituted C6 to C30 aryl group, a substituted or unsubstituted C2 to C30 heteroaryl group, or a combination thereof,
n1 and n2 are independently an integer of 0 or 1, and $1 \leq n1+n2 \leq 2$,
wherein the "substituted" refers to replacement of at least one hydrogen by deuterium, a C1 to C30 alkyl group, a C6 to C30 aryl group, or a C2 to C30 heteroaryl group.

2. The compound for an organic optoelectric device of claim 1, which is represented by one of Chemical Formulae I-A to I-E:

[Chemical Formula I-A]

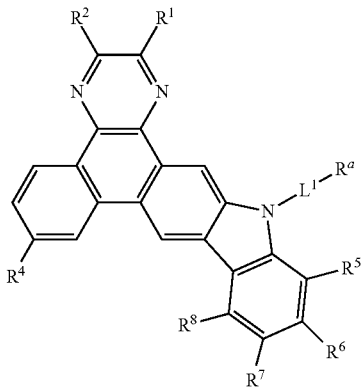

[Chemical Formula I-B]

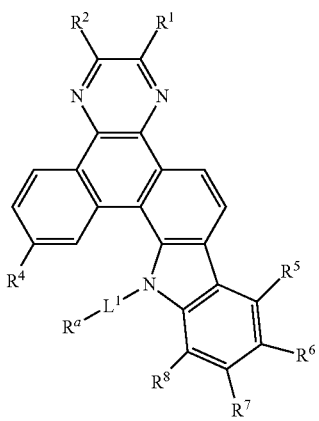

[Chemical Formula I-C]

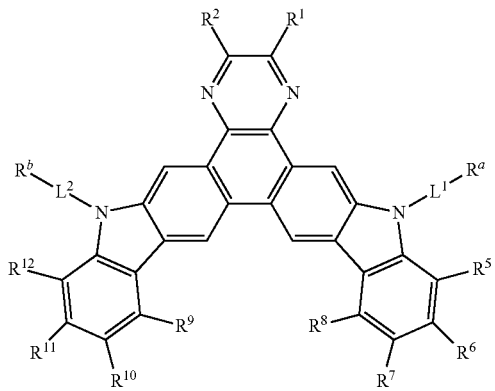

[Chemical Formula I-D]

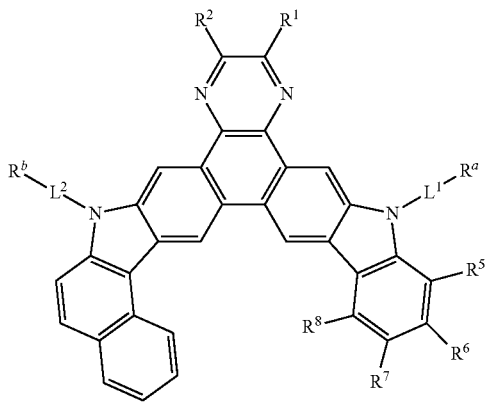

[Chemical Formula I-E]

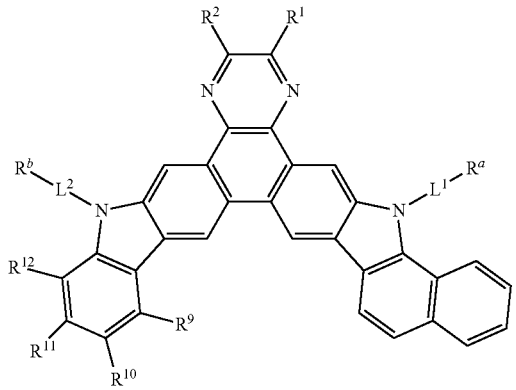

wherein, in Chemical Formulae I-A to I-E,
$R^1$, $R^2$, and $R^4$ to $R^{12}$ are independently hydrogen, deuterium, a substituted or unsubstituted C1 to C10 alkyl group, a substituted or unsubstituted C6 to C20 aryl group, a substituted or unsubstituted C2 to C30 heteroaryl group, or a combination thereof,
$L^1$ and $L^2$ are independently a single bond, a substituted or unsubstituted C6 to C30 arylene group, or a substituted or unsubstituted C2 to C30 heteroarylene group,
$R^a$ and $R^b$ are independently a substituted or unsubstituted C6 to C30 aryl group, a substituted or unsubstituted C2 to C30 heteroaryl group, or a combination thereof, and
the "substituted" refers to replacement of at least one hydrogen by deuterium, a C1 to C30 alkyl group, a C6 to C30 aryl group, or a C2 to C30 heteroaryl group.

3. The compound for an organic optoelectric device of claim 1, wherein $L^1$ and $L^2$ are independently a single bond, a phenylene group, a biphenylene group, a terphenylene group, a quaterphenylene group, or a combination thereof.

4. The compound for an organic optoelectric device of claim 3, wherein $L^1$ and $L^2$ are independently a single bond or selected from linking groups of Group 1:

[Group 1]

-continued

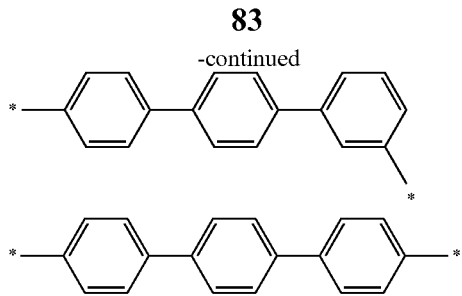

wherein, in Group 1,
* is a linking site with an adjacent atom.

5. The compound for an organic optoelectric device of claim 1, wherein $R^a$ and $R^b$ are independently a substituted or unsubstituted phenyl group, a substituted or unsubstituted biphenyl group, a substituted or unsubstituted terphenyl group, a substituted or unsubstituted quaterphenyl group, a substituted or unsubstituted pyridinyl group, a substituted or unsubstituted pyrimidinyl group, a substituted or unsubstituted triazinyl group, a substituted or unsubstituted quinolinyl group, a substituted or unsubstituted isoquinolinyl group, a substituted or unsubstituted indolyl group, a substituted or unsubstituted azaindolyl group, a substituted or unsubstituted benzoxazolyl group, a substituted or unsubstituted benzthiazolyl group, a substituted or unsubstituted azatriphenylenyl group, a substituted or unsubstituted azaphenanthrenyl group, a substituted or unsubstituted quinazolinyl group, or a combination thereof, and the "substituted" refers to replacement of at least one hydrogen by deuterium, C1 to C30 alkyl group, C6 to C30 aryl group, or C2 to C30 heteroaryl group.

6. The compound for an organic optoelectric device of claim 5, wherein $R^a$ and $R^b$ are independently selected from substituents of Group 2:

[Group 2]

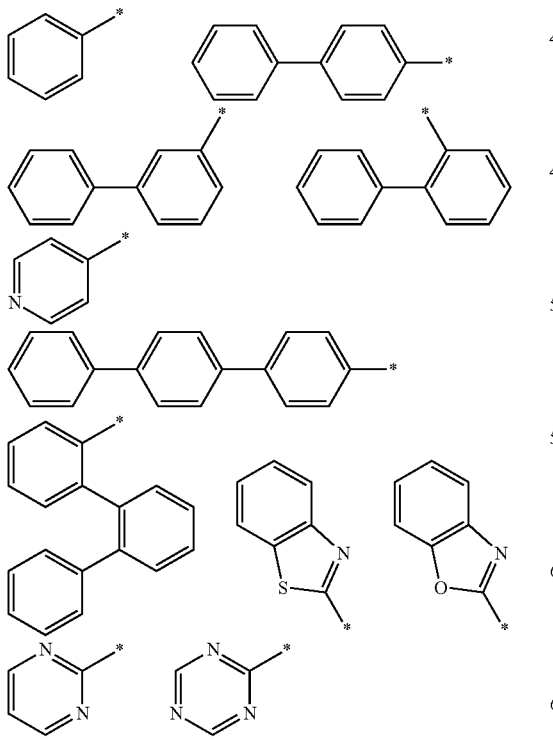

-continued

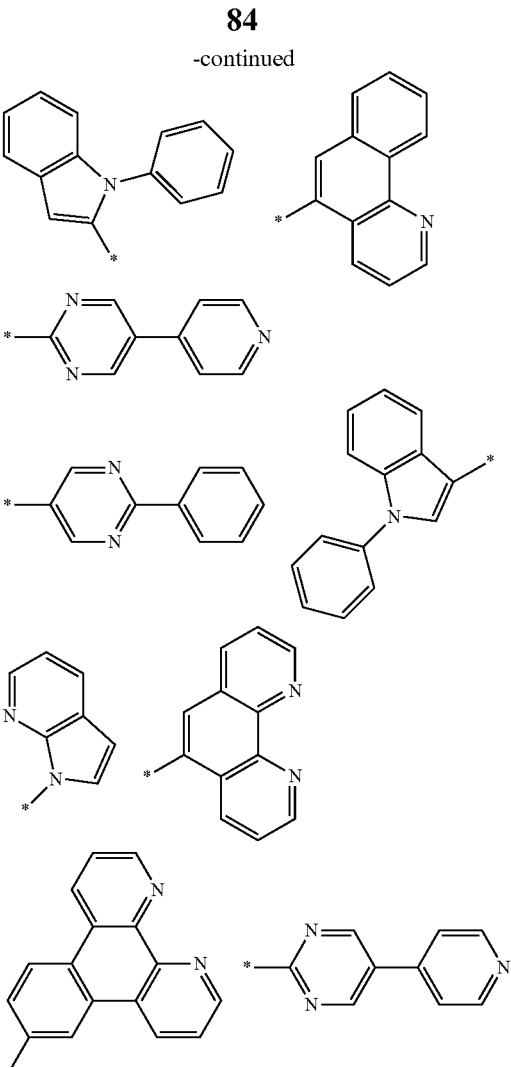

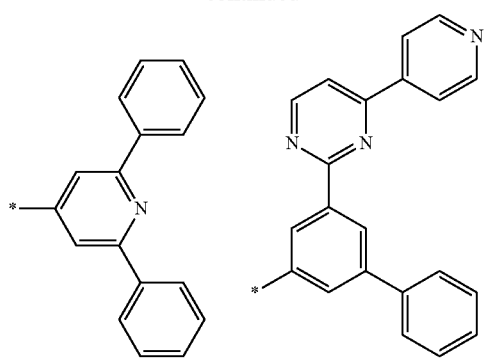
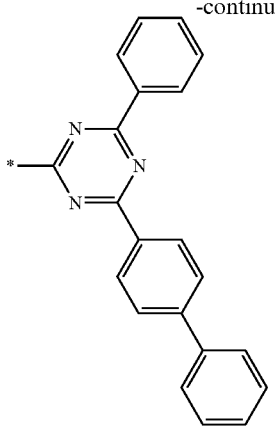
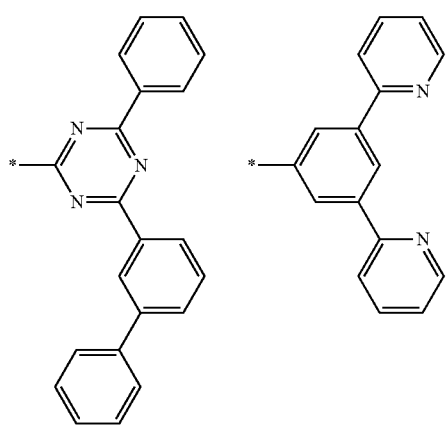
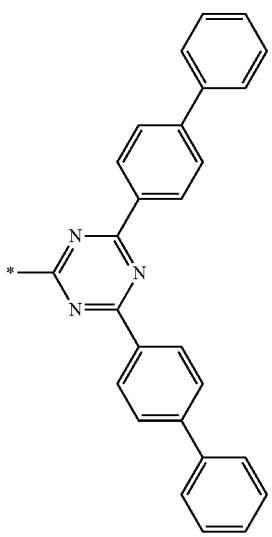
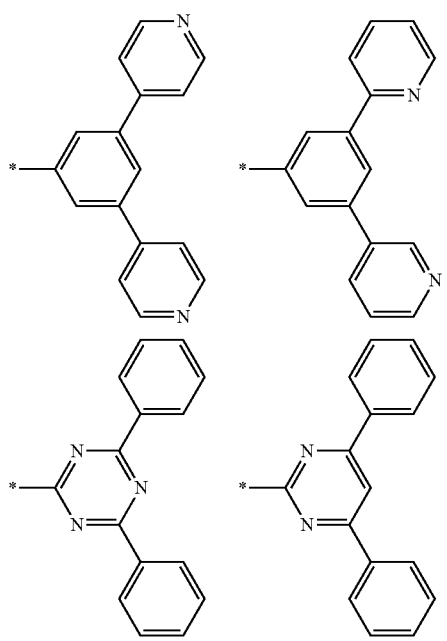
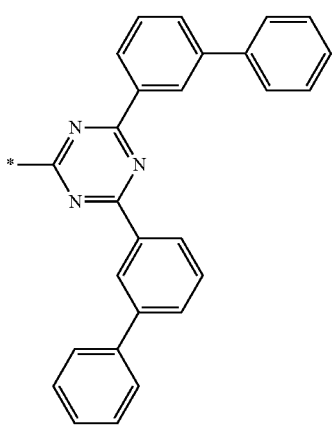
wherein, in Group 2,
* is a linking site with an adjacent atom.
7. The compound for an organic optoelectric device of claim 1, which is selected from compounds of Group 3:

[Group 3]
1
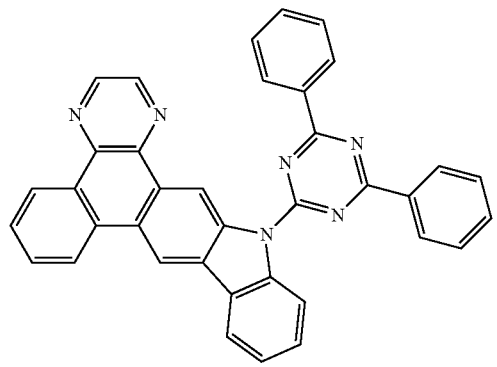
2
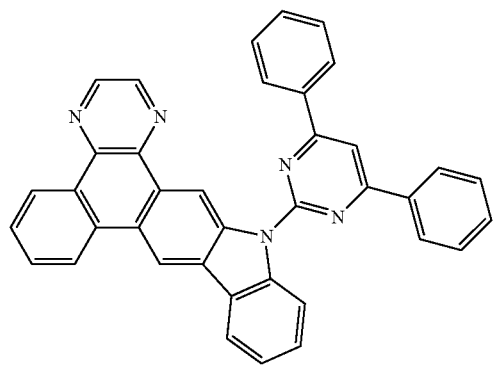
3
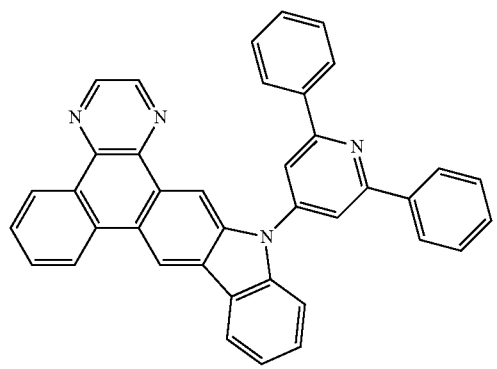
4
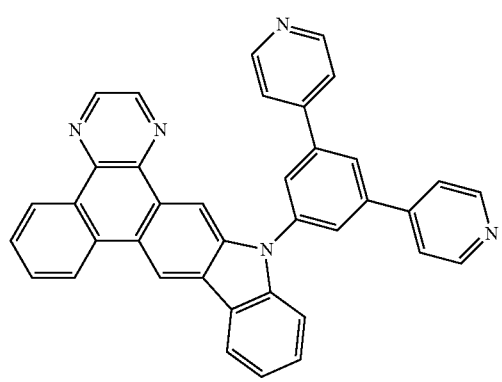
-continued
5
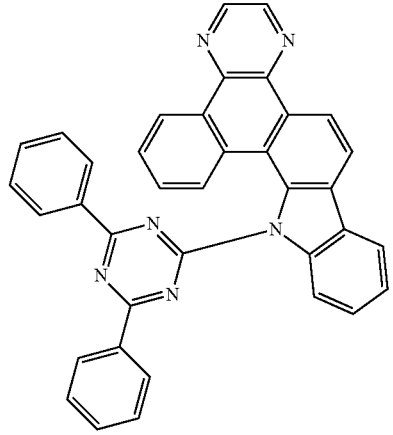
6
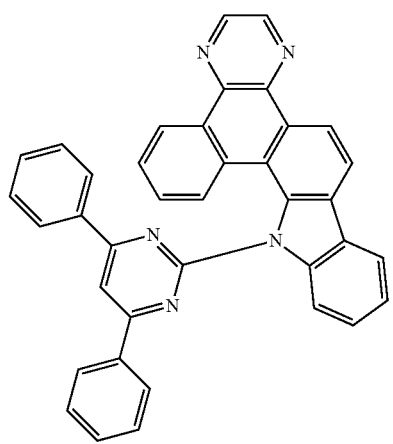
7
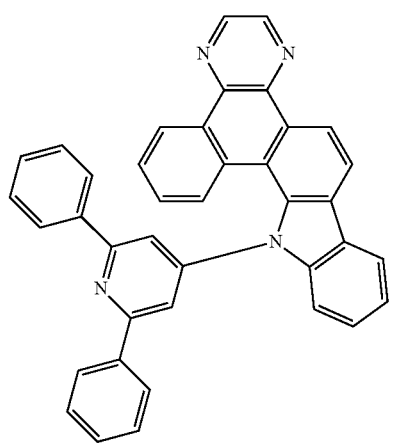

8
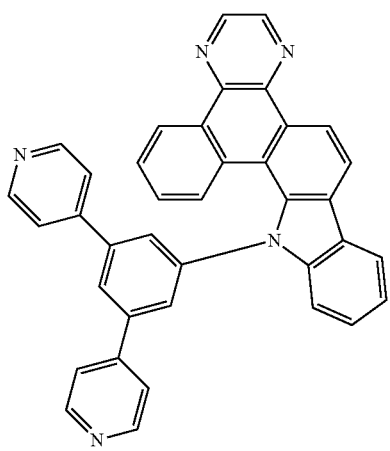
9
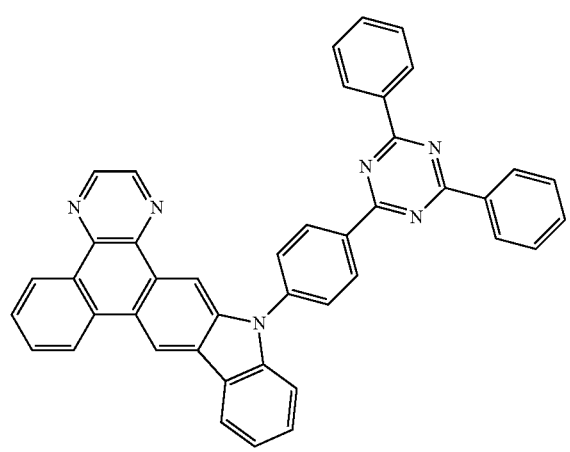
10
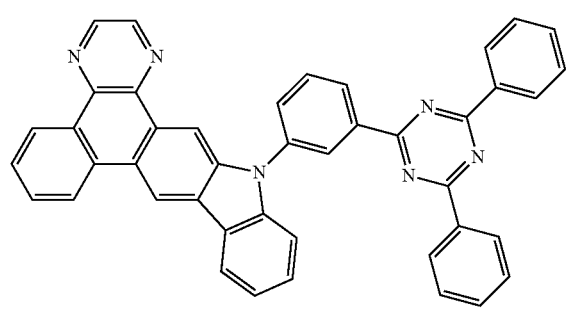
11
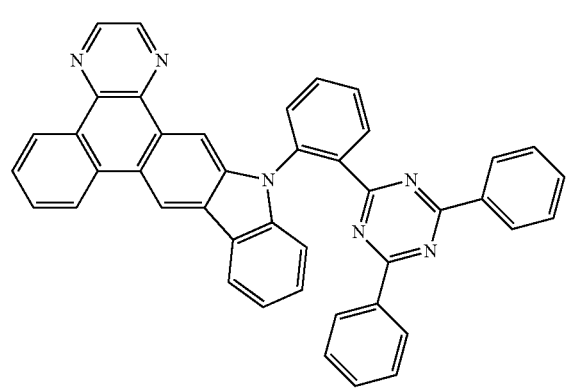
12
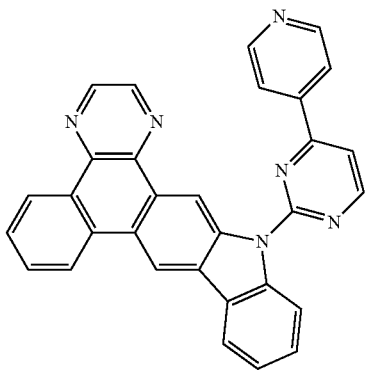
13
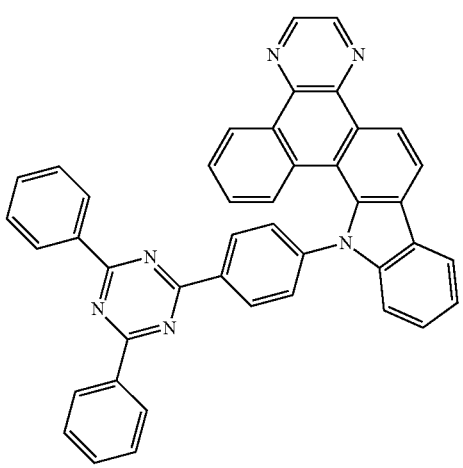
14
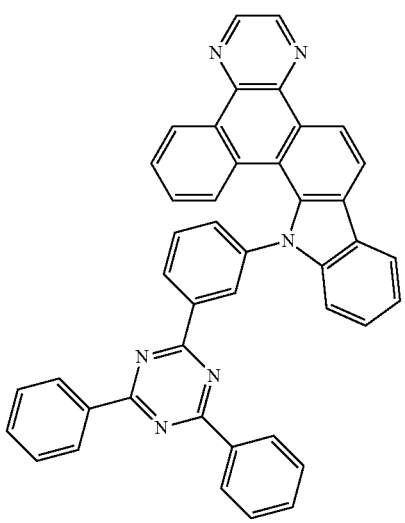

91
-continued
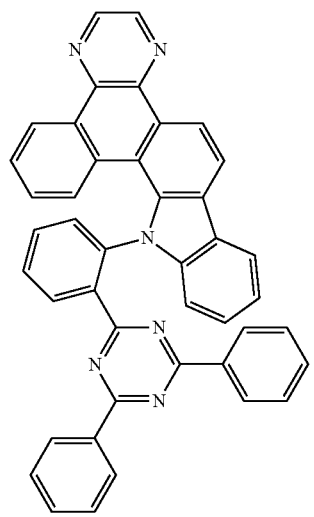
15
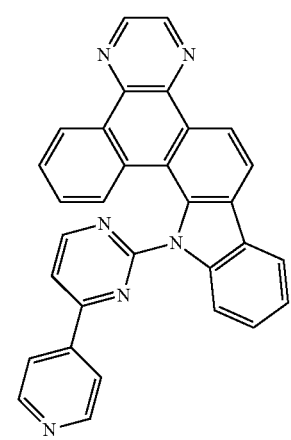
16
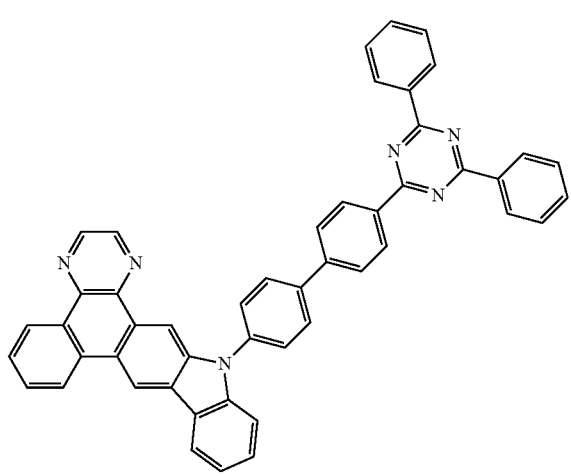
17
92
-continued
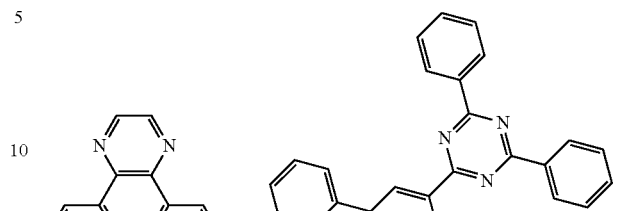
18
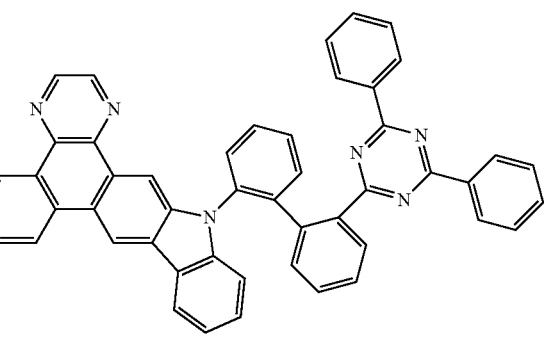
19
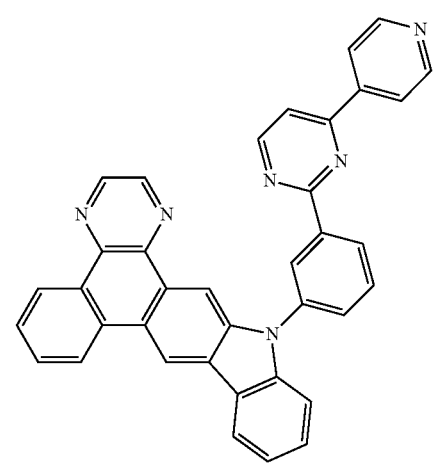
20

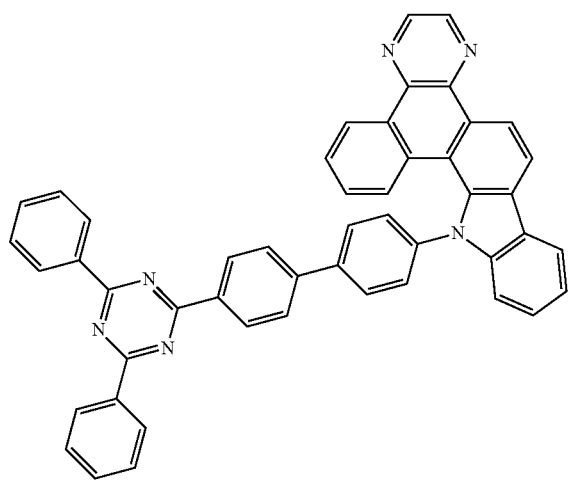
21
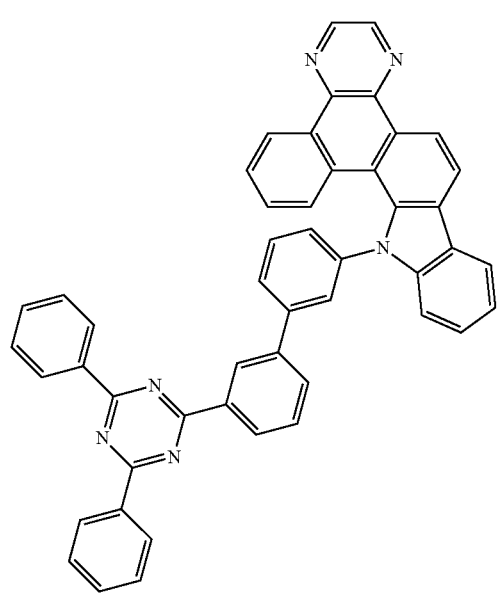
22
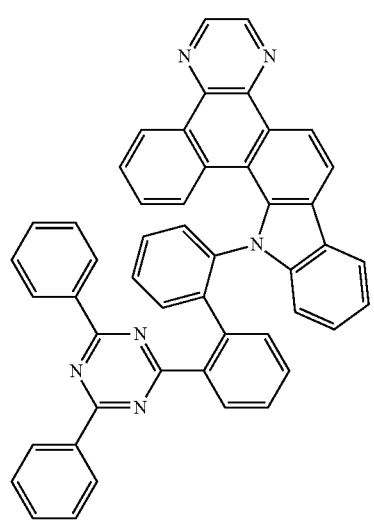
23
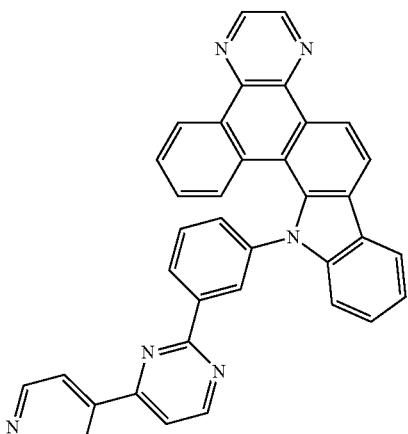
24
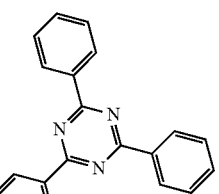
25
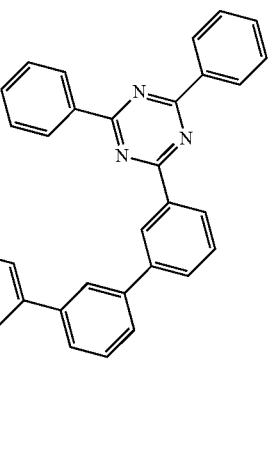
26

27
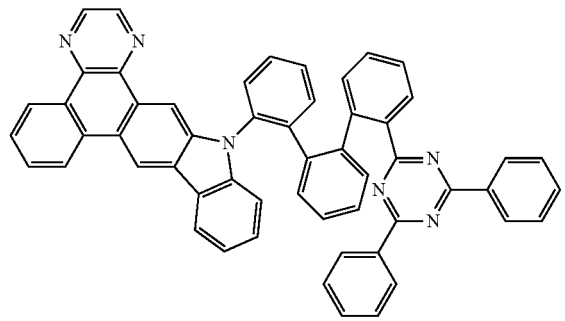
28
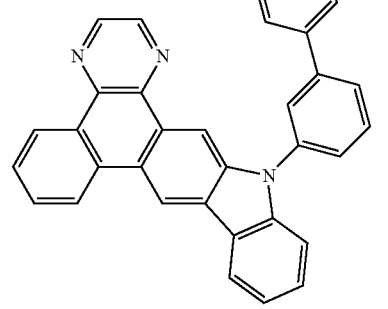
29
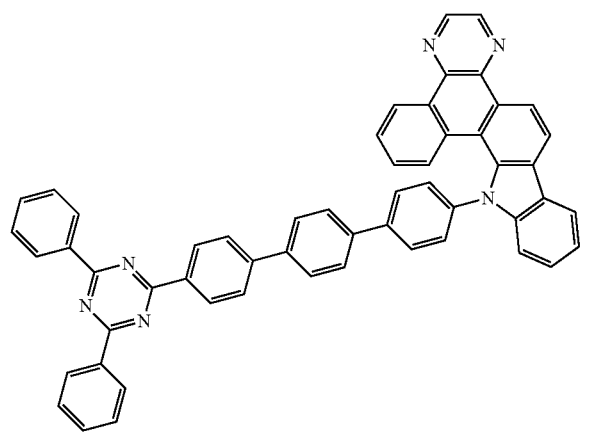
30
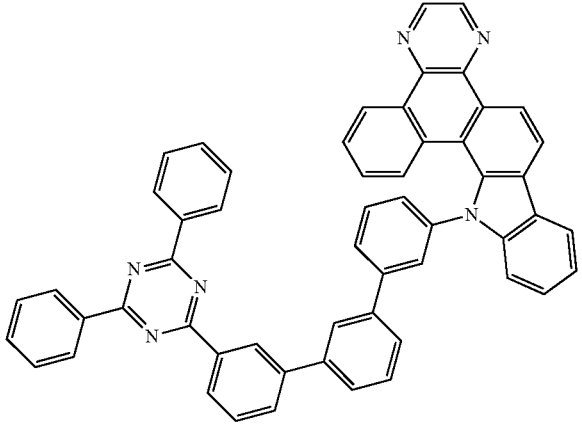
31
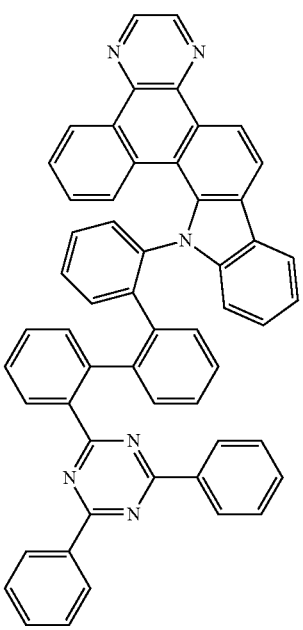
32
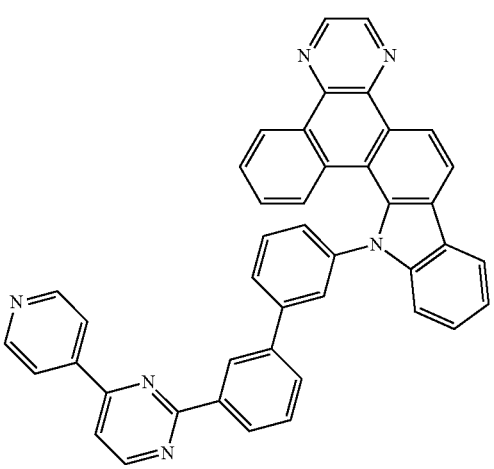

-continued
33
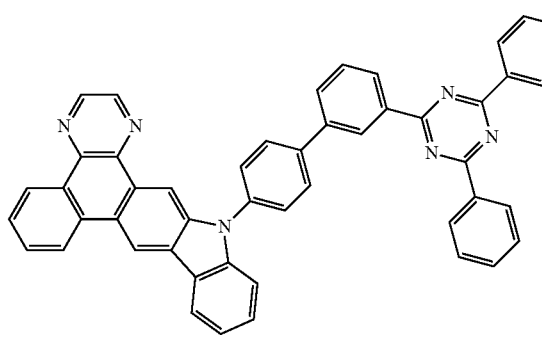
34
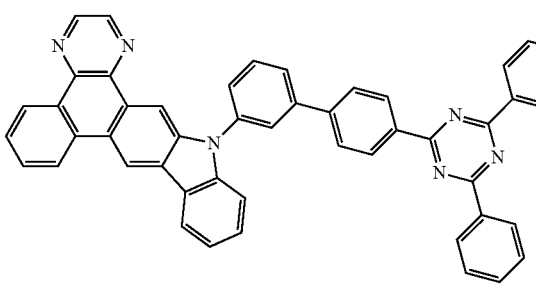
35
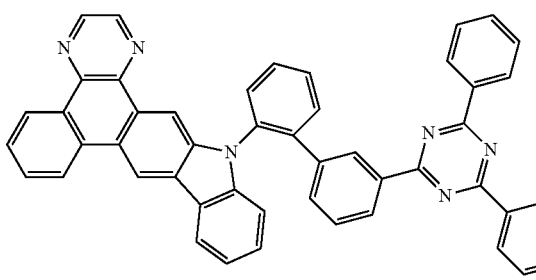
36
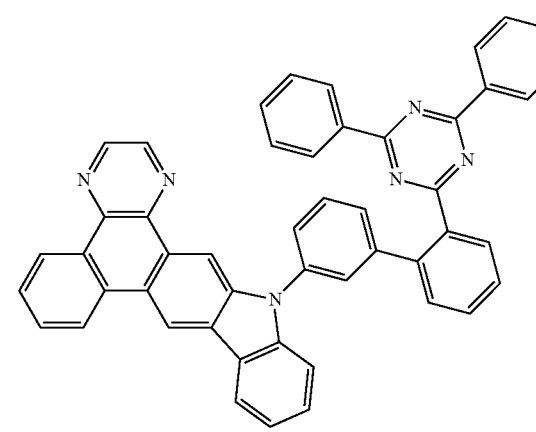
-continued
37
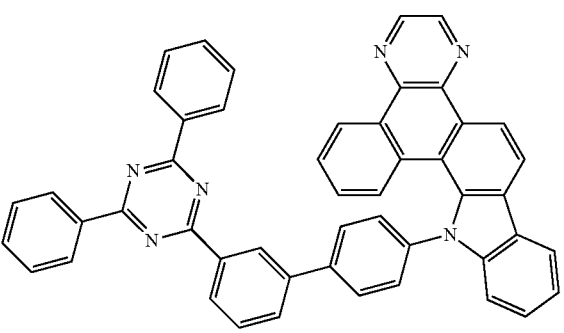
38
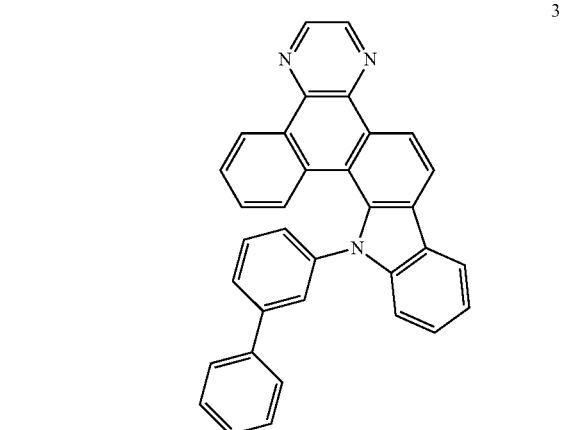
39
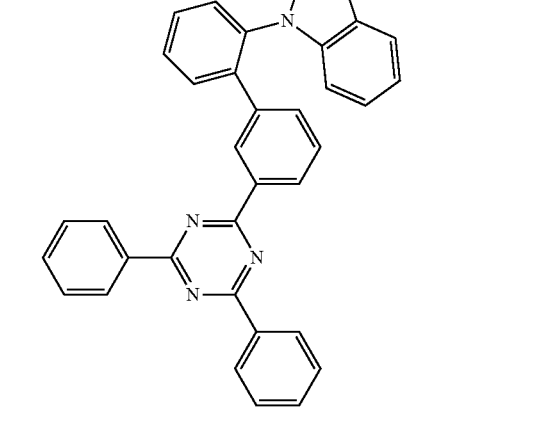

99
-continued
40
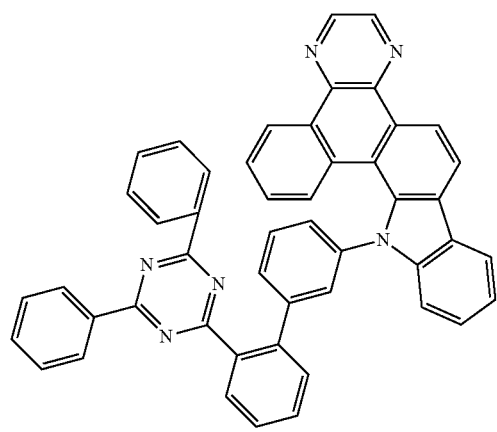
41
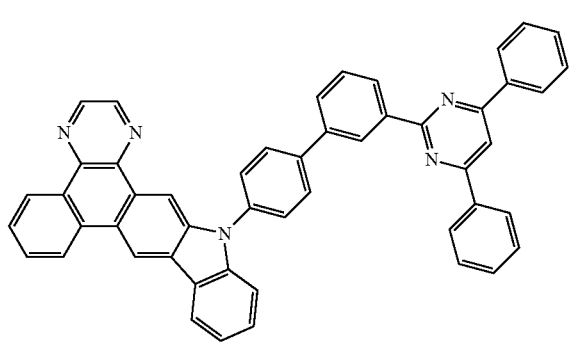
42
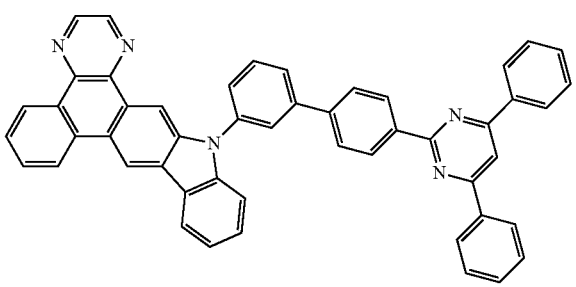
43
100
-continued
44
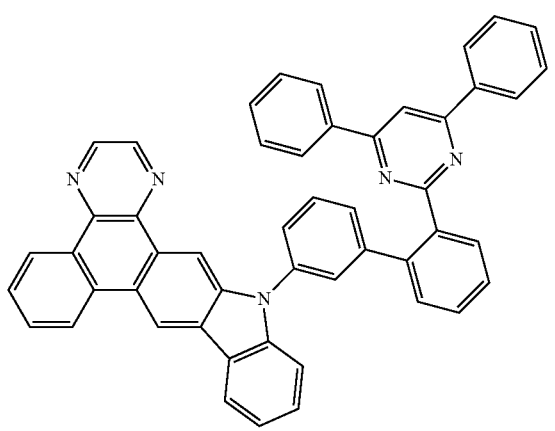
45
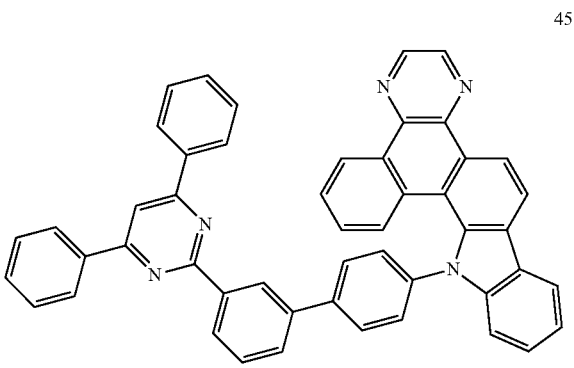
46
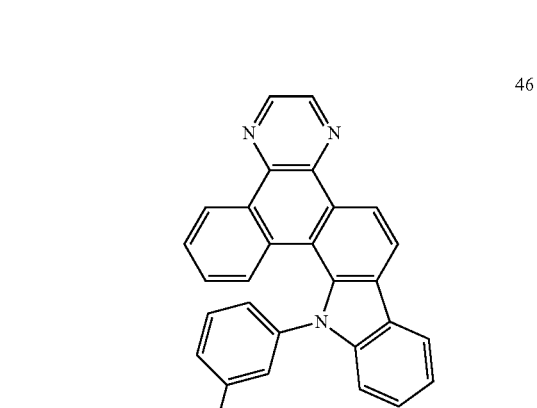
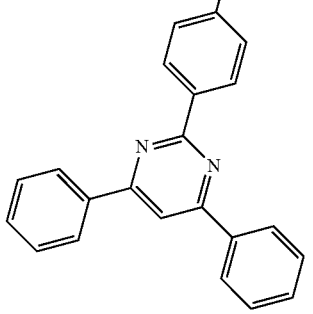

101
-continued
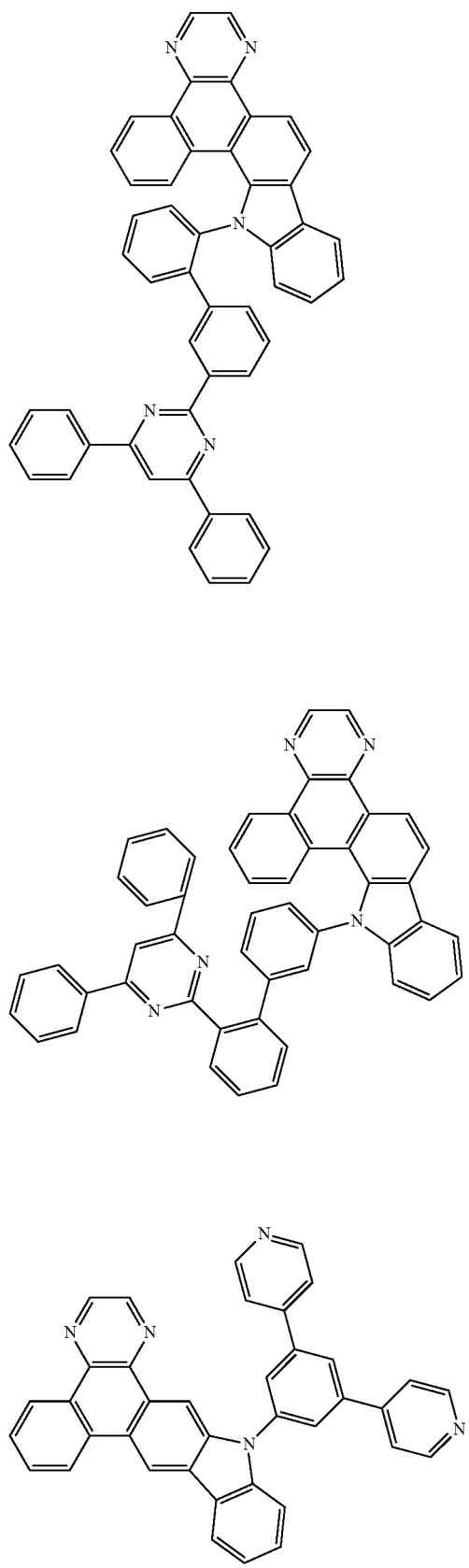
102
-continued
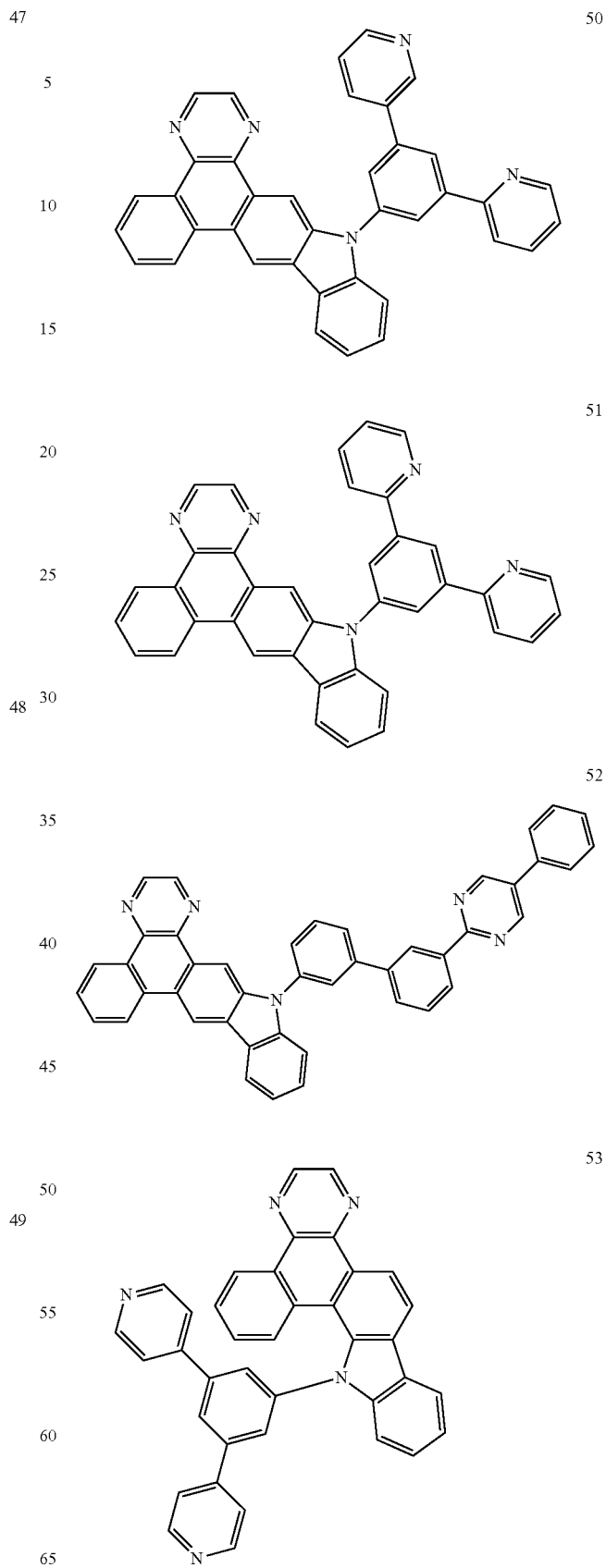

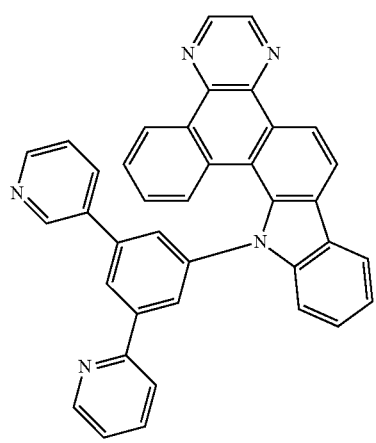
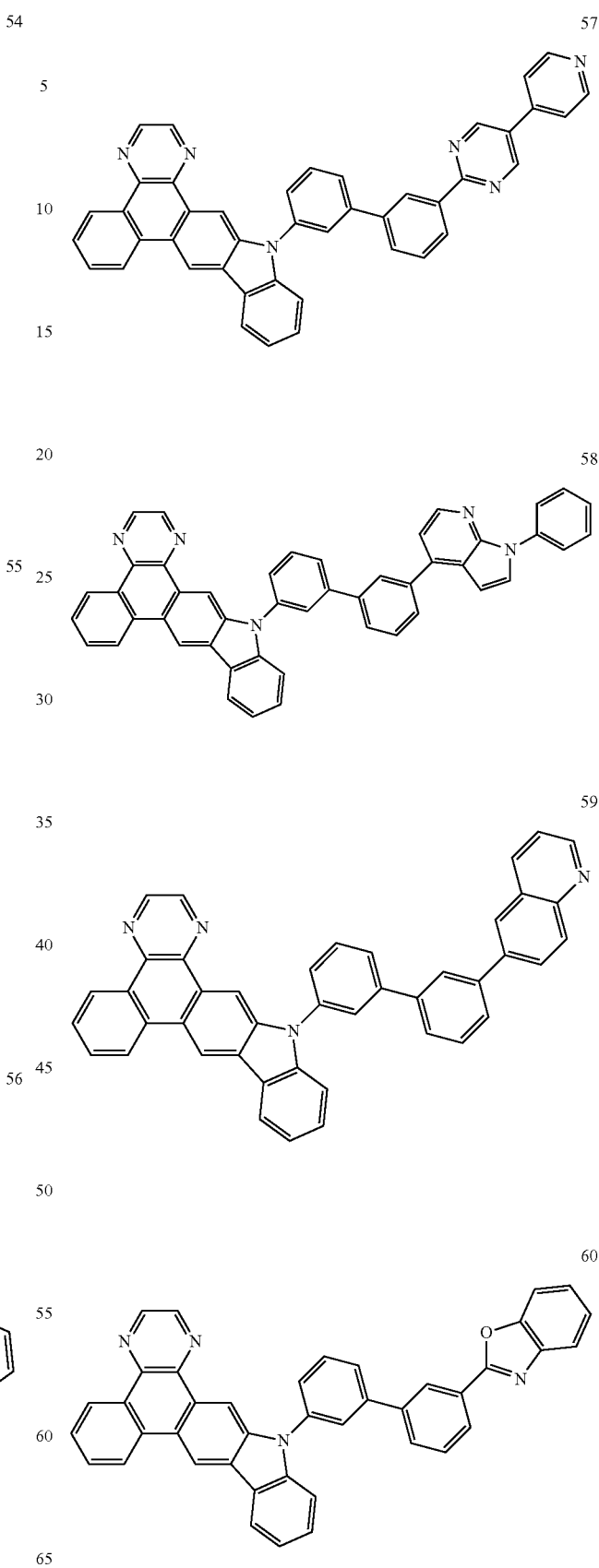

-continued

61

62

63

-continued

64

65

66

67

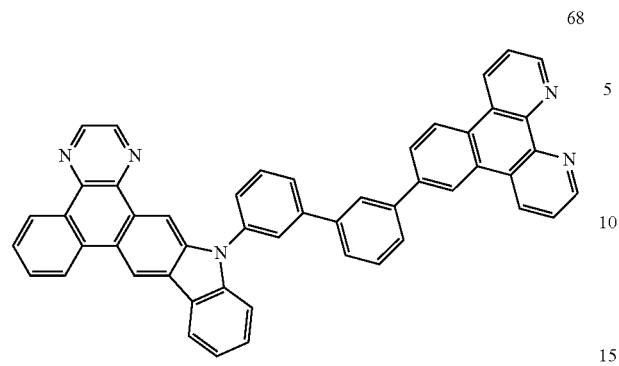
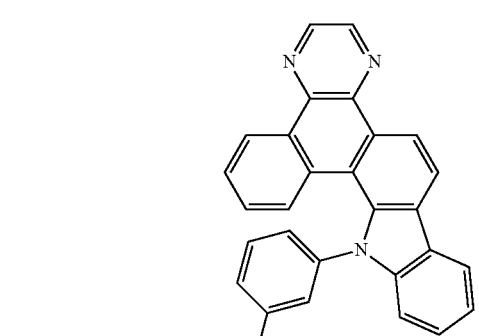
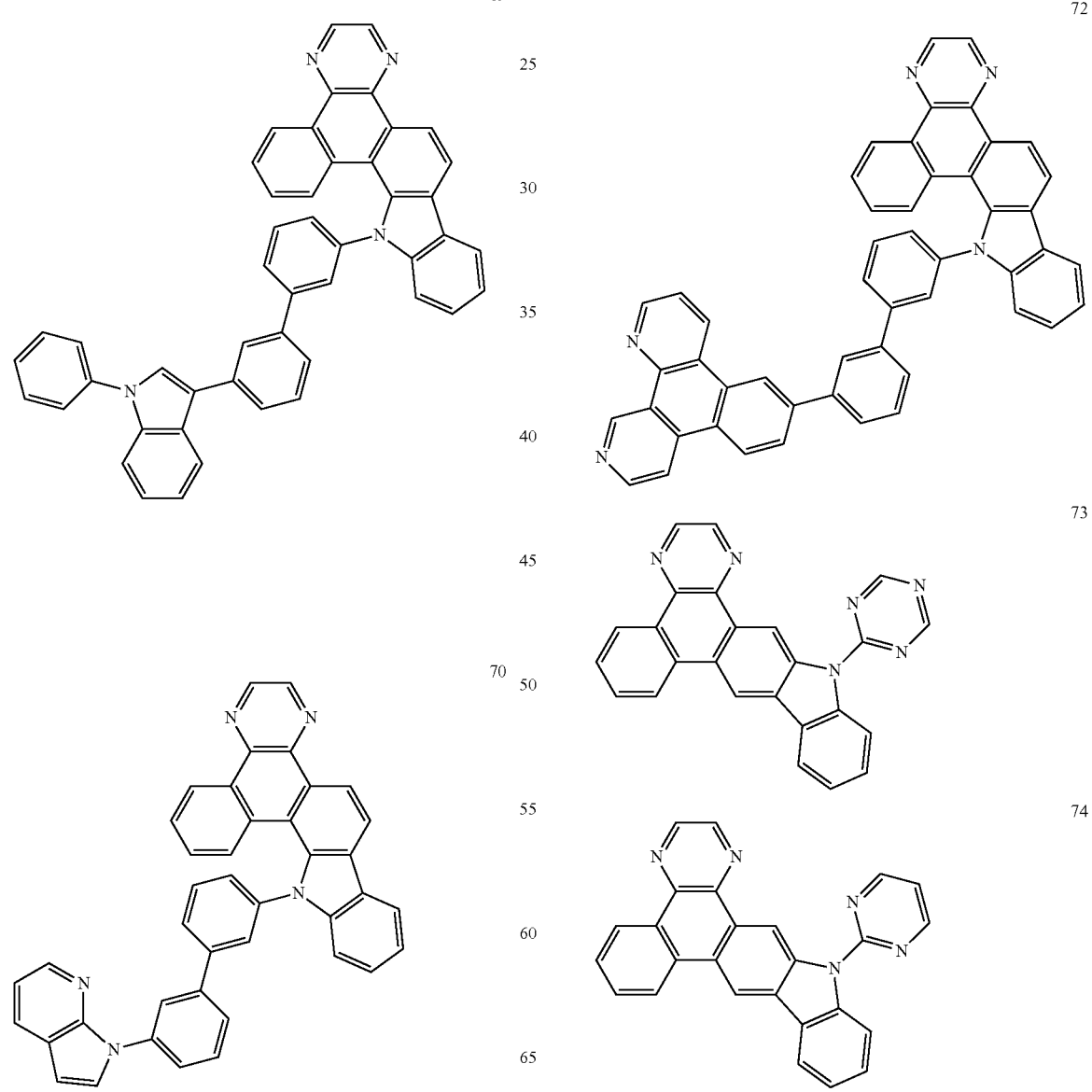

75
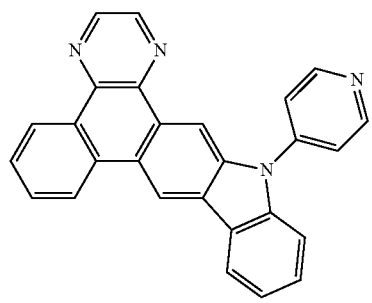
76
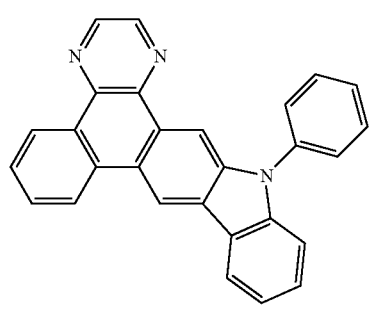
77
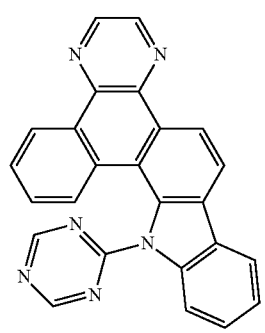
78
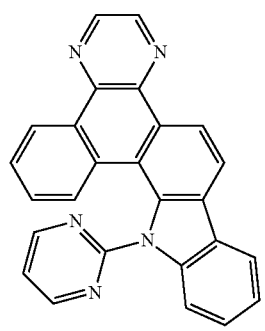
79
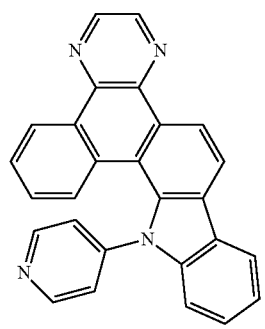
80
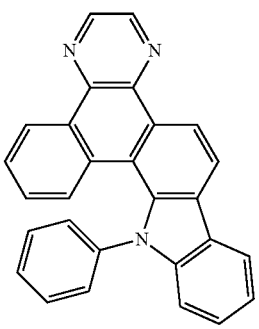
81
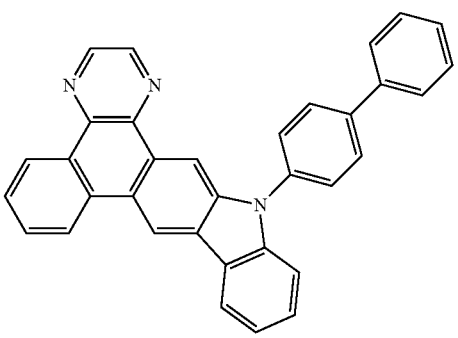
82
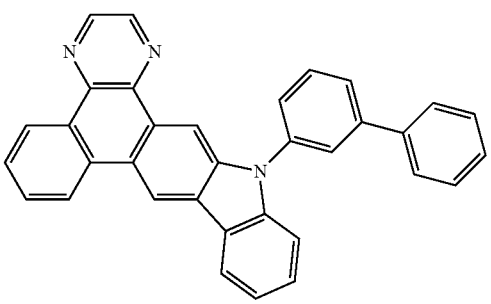
83
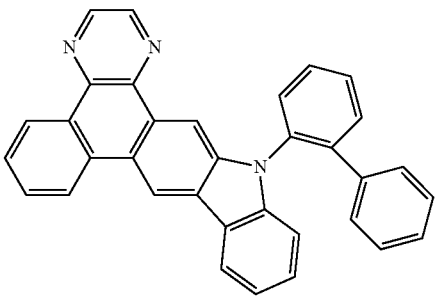

84
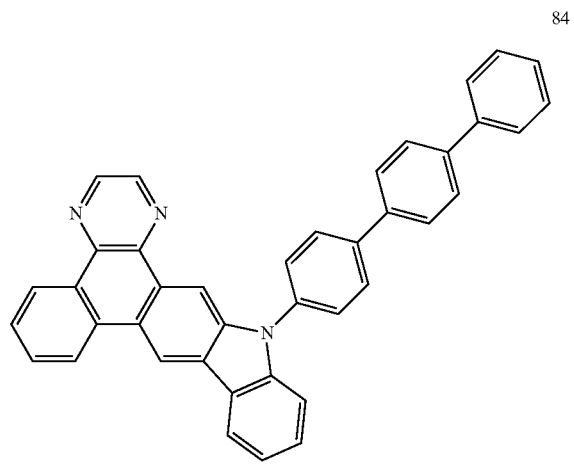
85
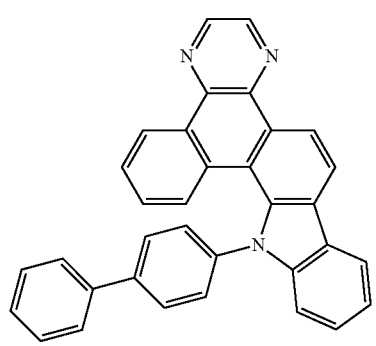
86
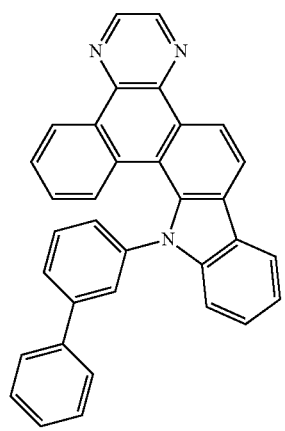
87
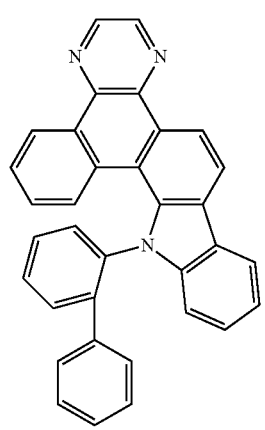
88
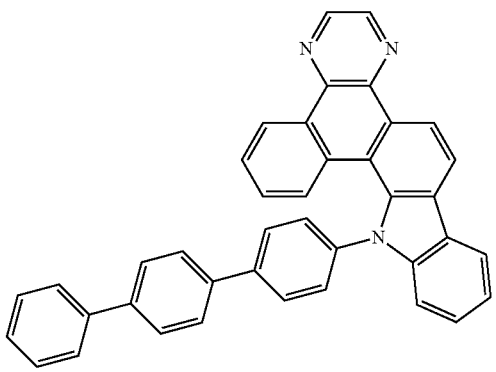
89
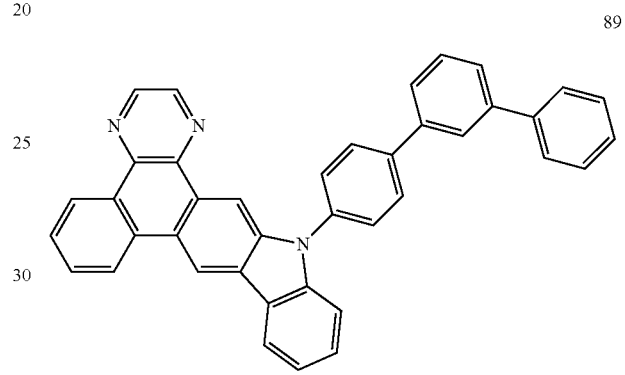
90
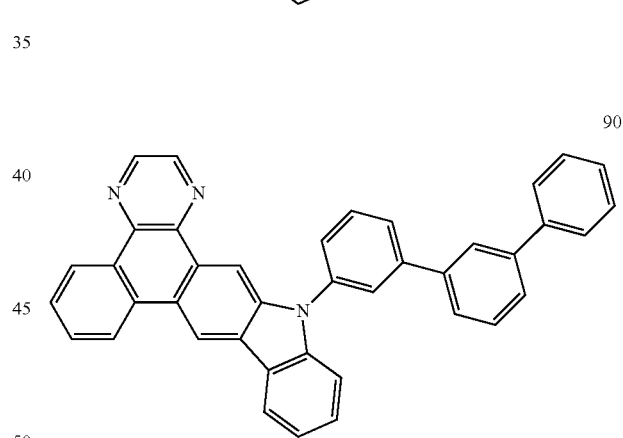
91
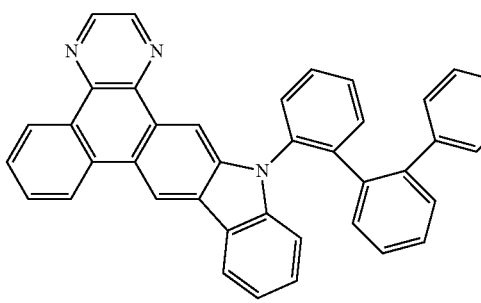

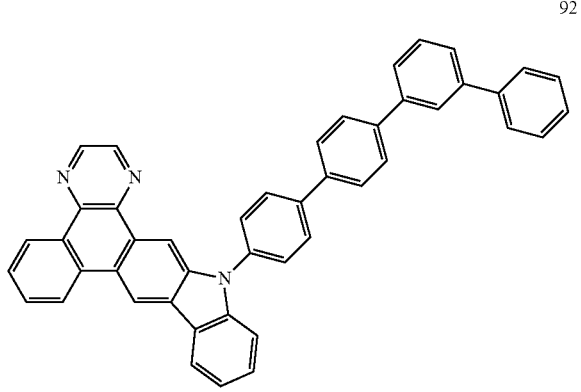
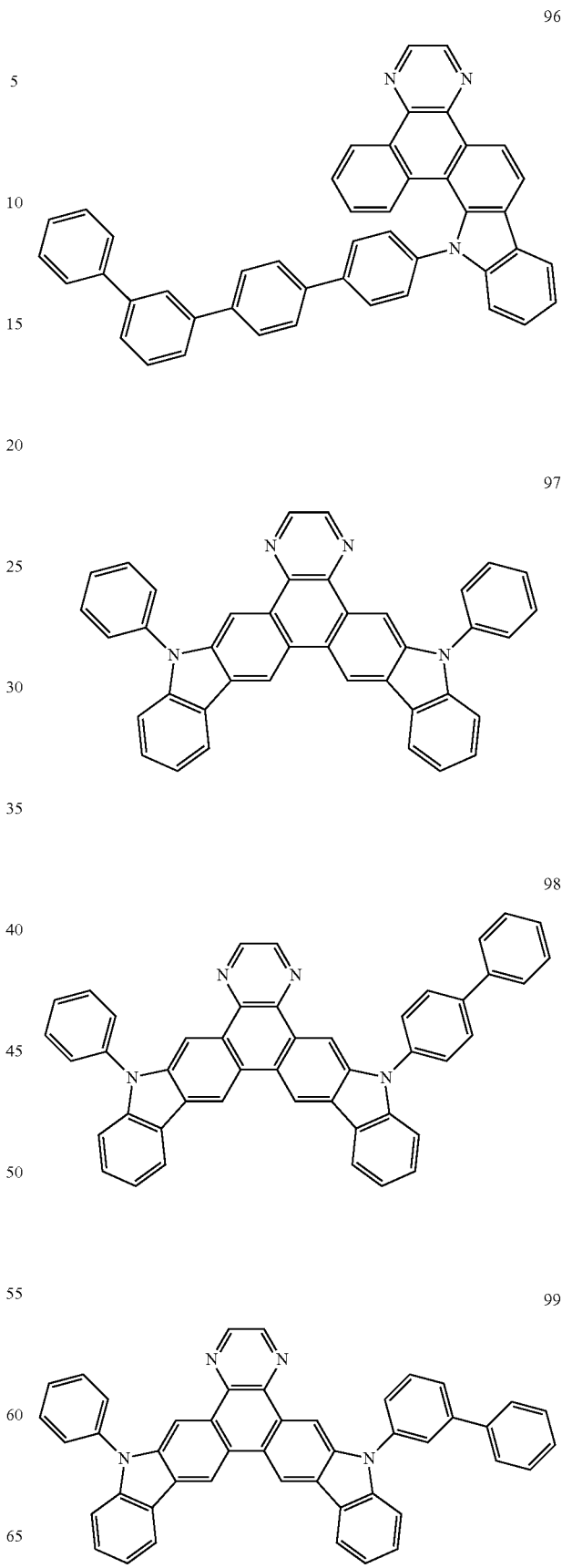

US 10,270,042 B2
115
-continued
100
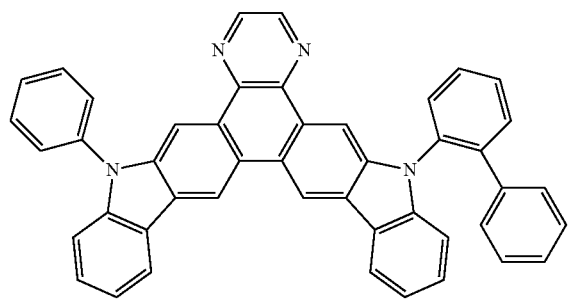
101
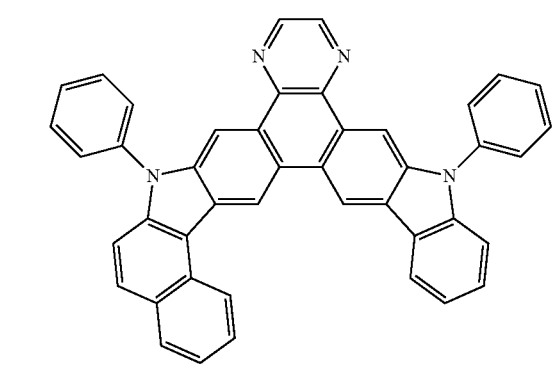
102
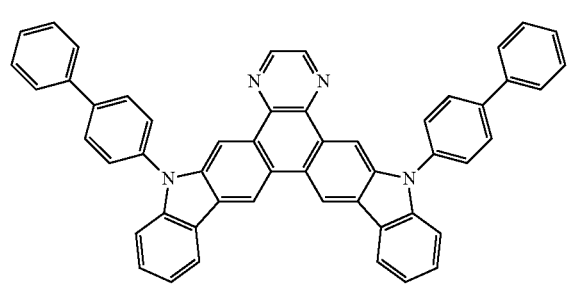
103
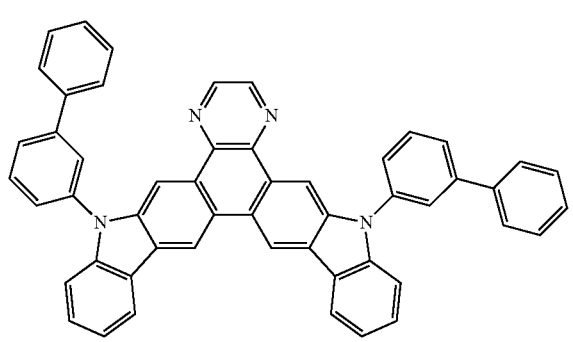
104
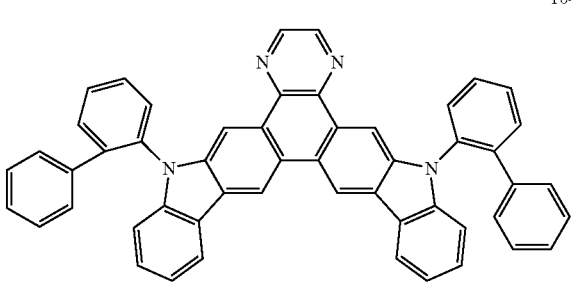
116
-continued
105
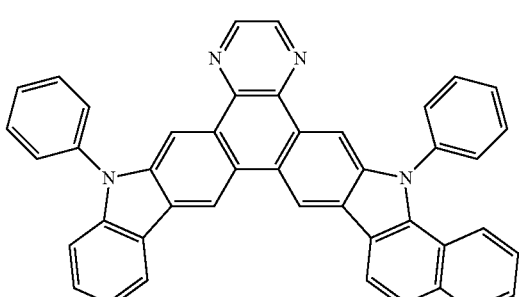
106
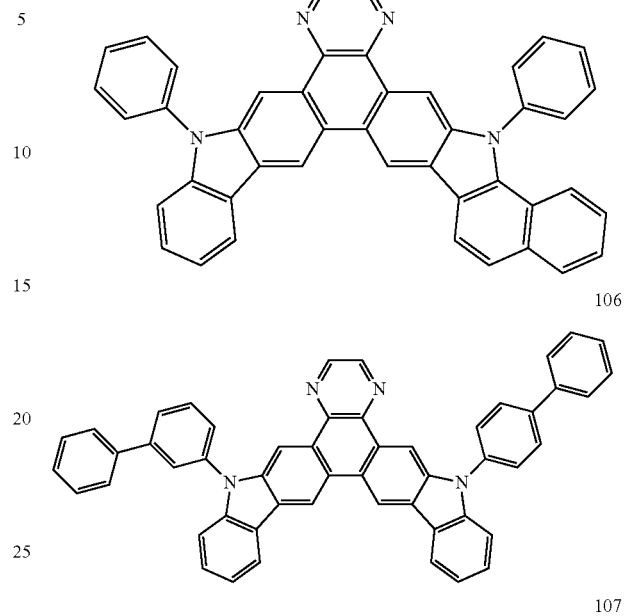
107
108
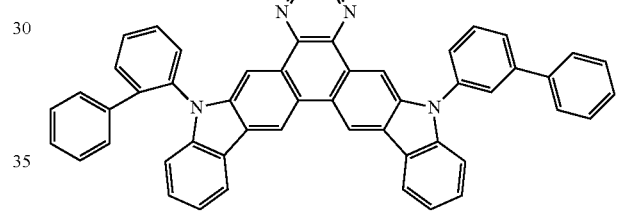
109
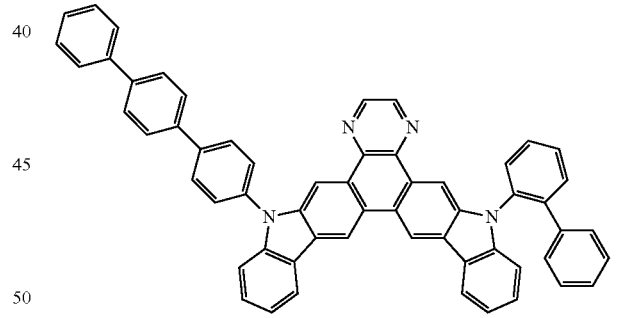
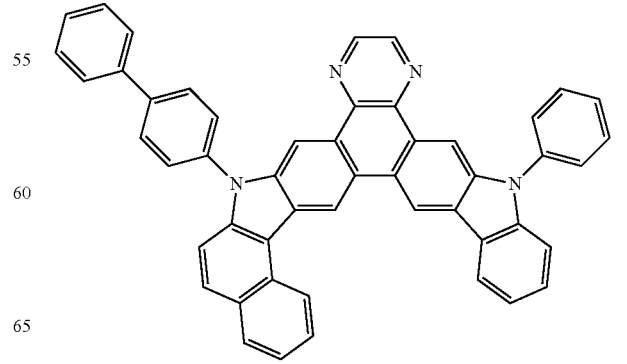

110
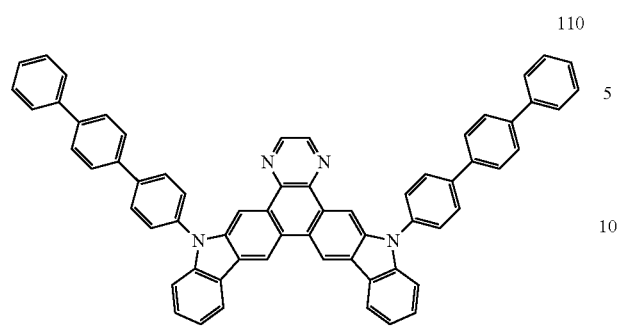
111
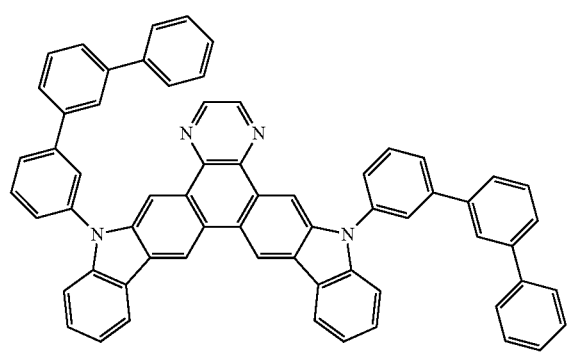
112
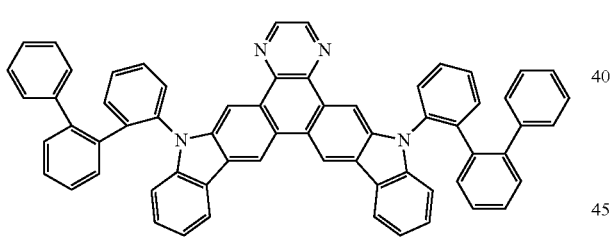
113
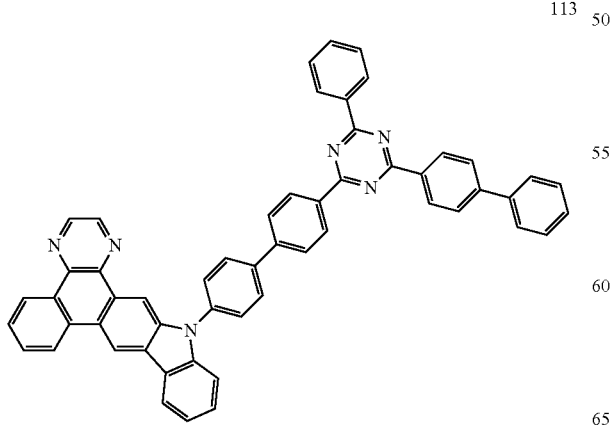
114
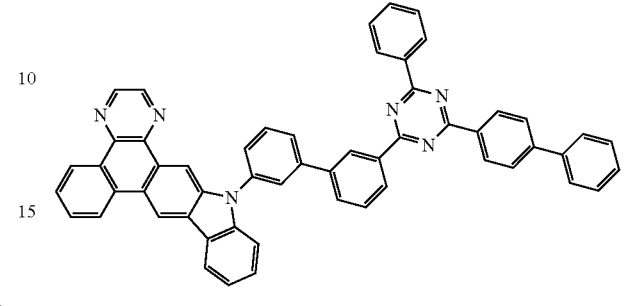
115
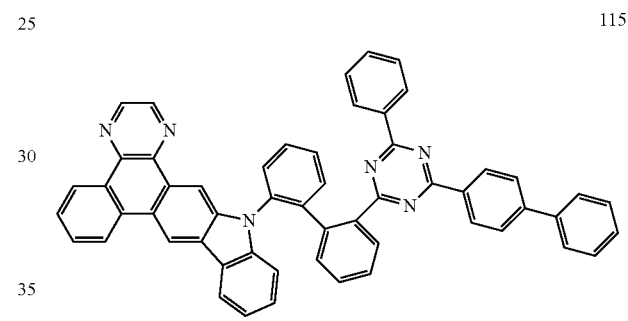
116
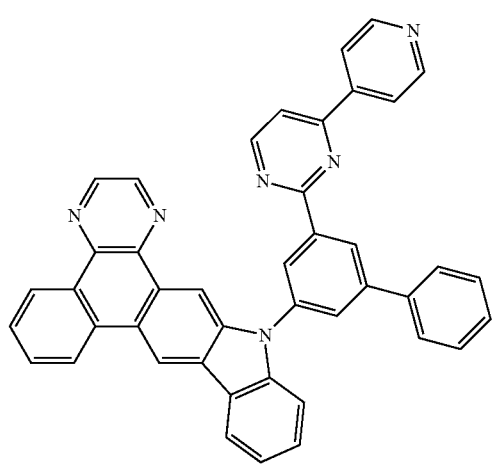

-continued
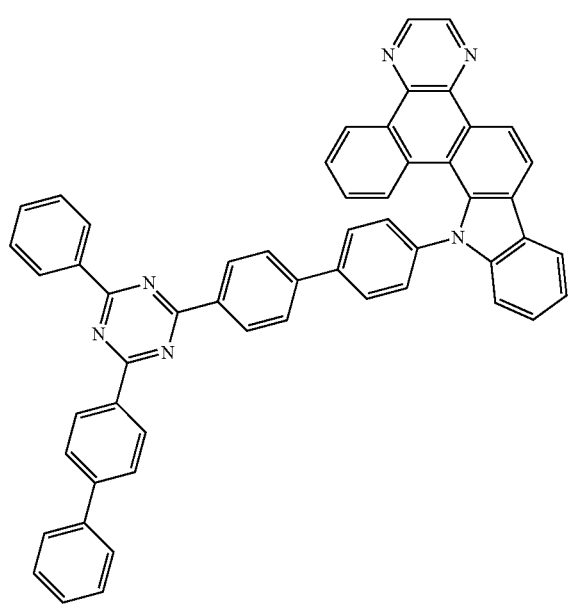
117
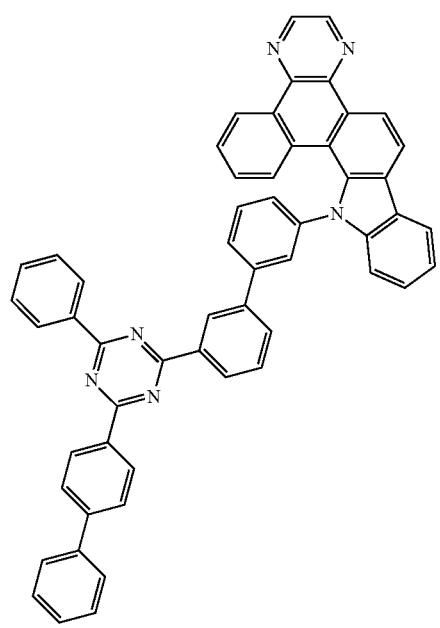
118
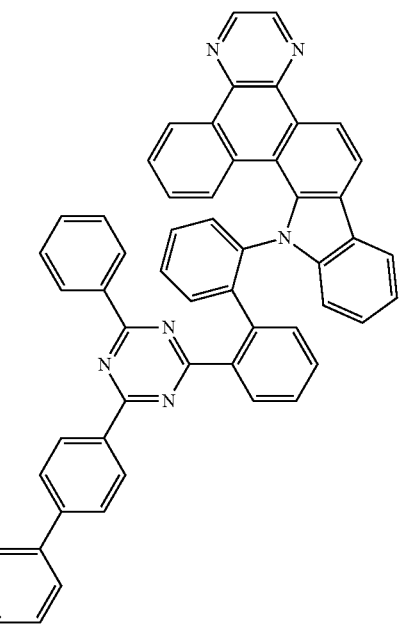
119
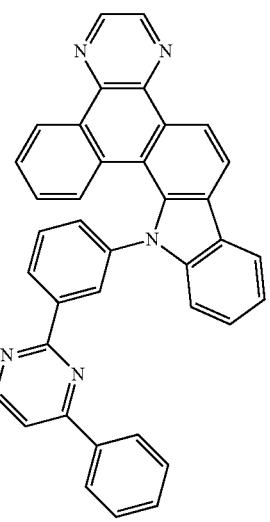
120
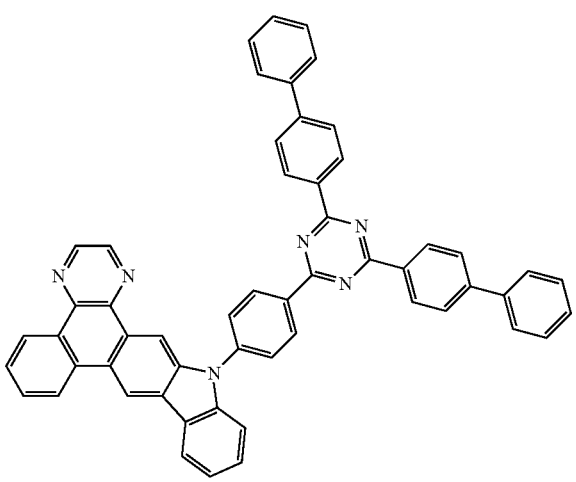
121

122
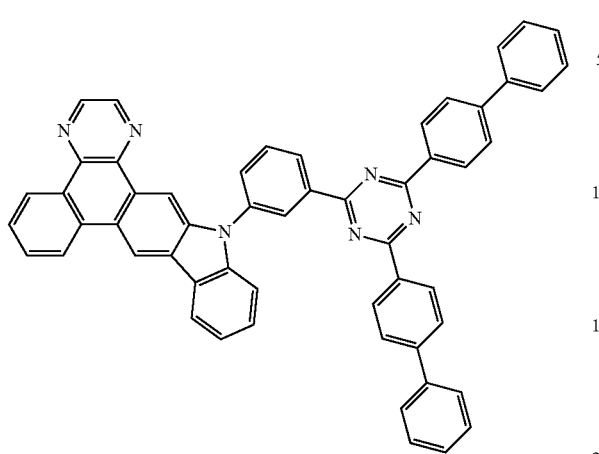
123
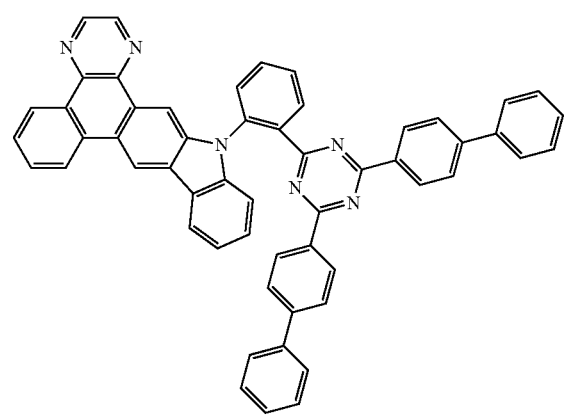
124
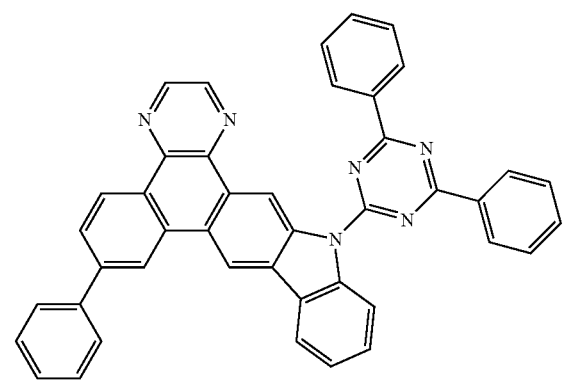
125
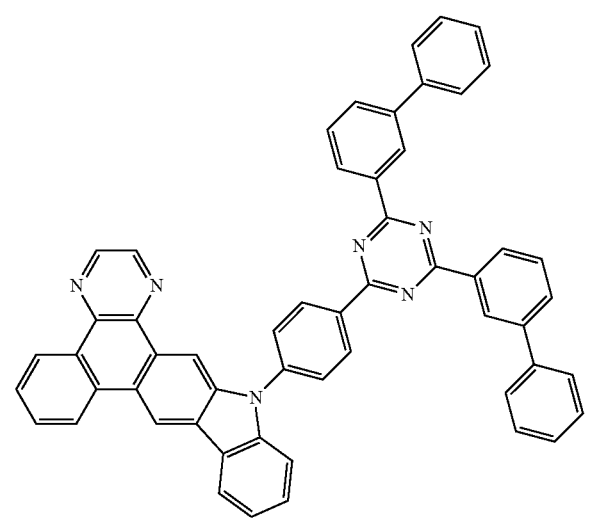
126
126 is shown above
127
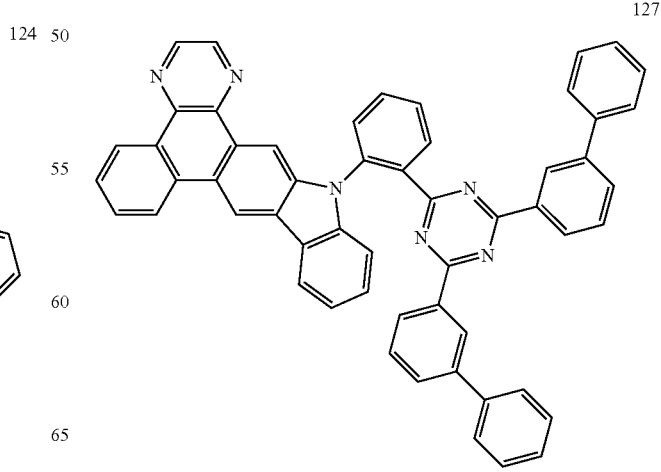

123
-continued
128
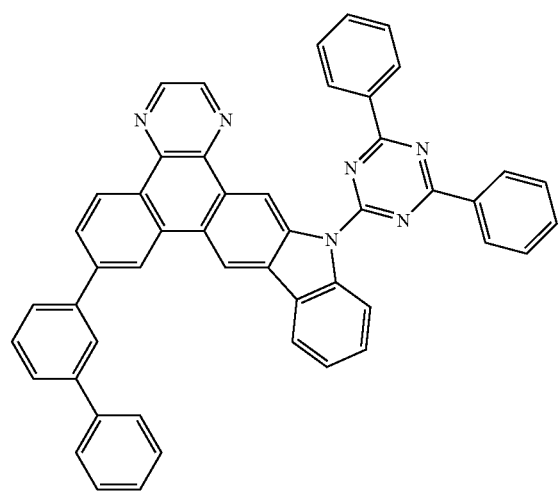
129
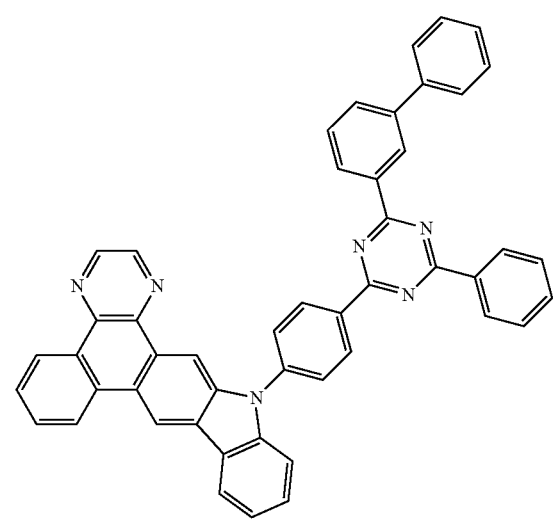
130
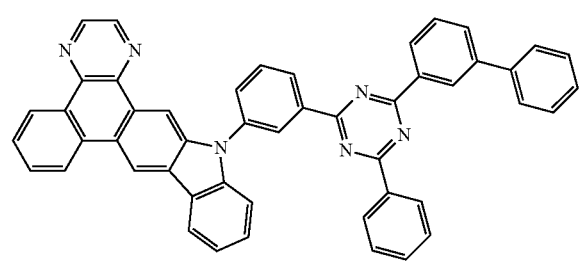
124
-continued
131
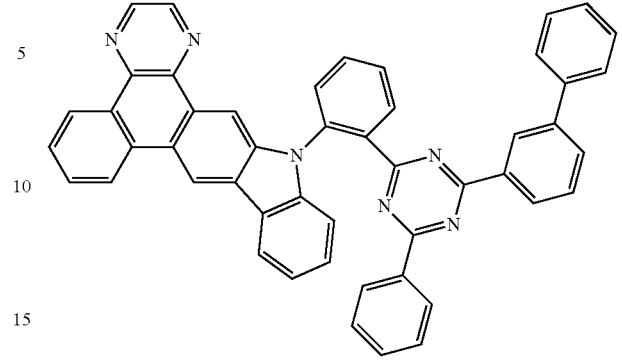
132
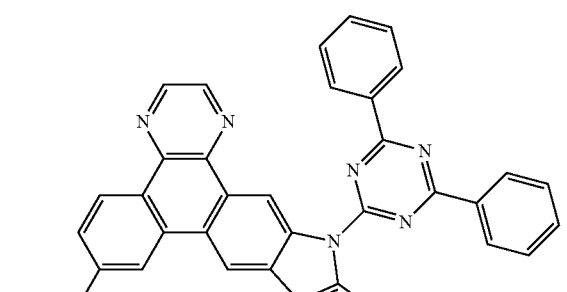
133
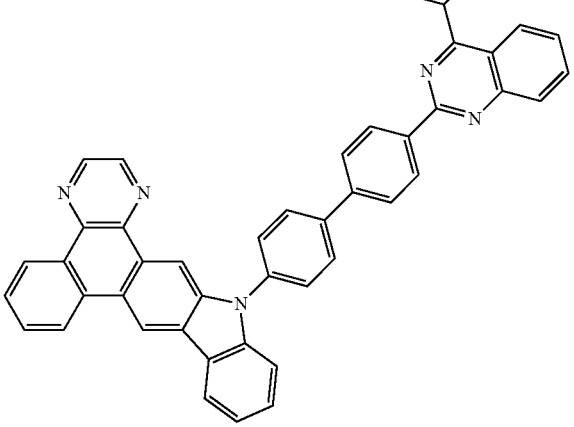

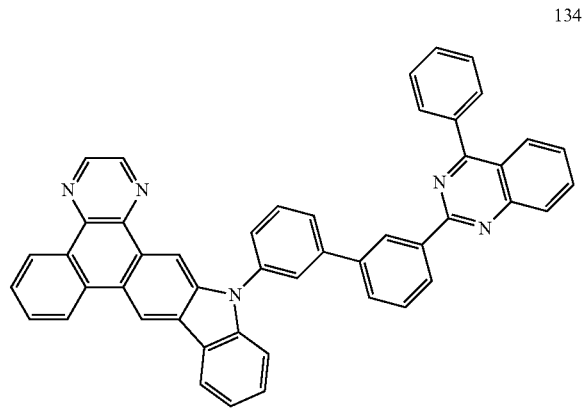
134
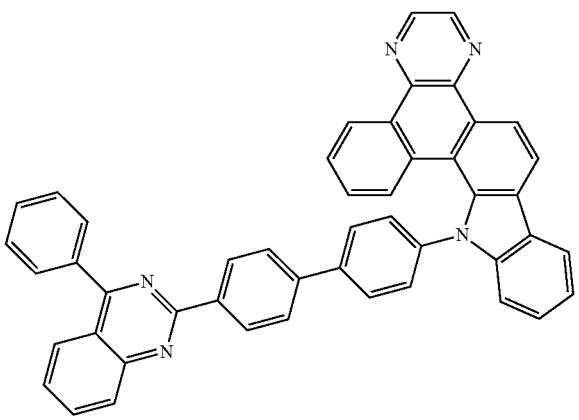
137
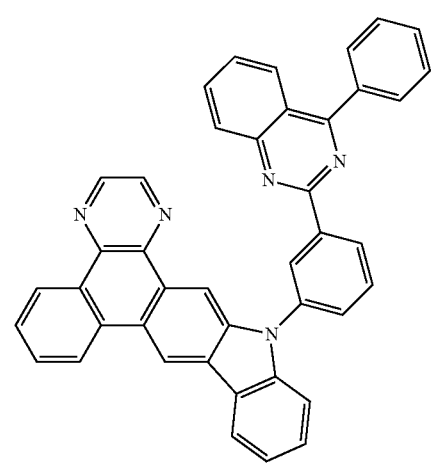
135
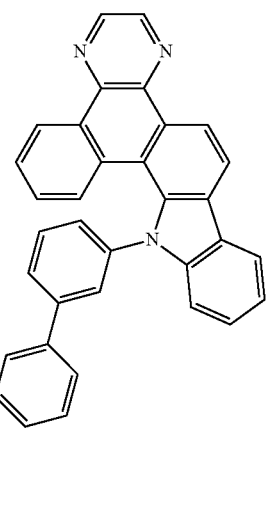
138
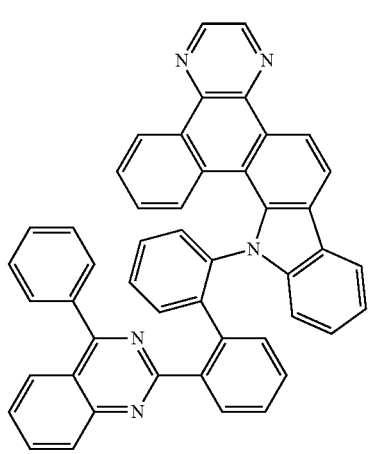
136
139

-continued

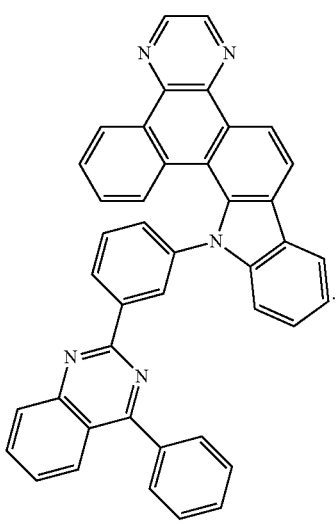

140

8. An organic optoelectric device, comprising
an anode and a cathode facing each other, and
at least one organic layer disposed between the anode and the cathode,
wherein the organic layer includes the compound for an organic optoelectric device of claim 1.

9. The organic optoelectric device of claim 8, wherein the organic layer includes a light-emitting layer, and
the light-emitting layer includes the compound for an organic optoelectric device.

10. The organic optoelectric device of claim 9, wherein the compound for an organic optoelectric device is included as a host of the light-emitting layer.

11. A display device comprising the organic optoelectric device of claim 8.

* * * * *